United States Patent [19]

Robinson et al.

[11] Patent Number: 5,374,395

[45] Date of Patent: Dec. 20, 1994

[54] DIAGNOSTICS INSTRUMENT

[75] Inventors: David Robinson, Folkestone; Ernest Bate, Great Chart; Simon Kellard; Mark Watson, both of Ashford, all of England; Donald E. Mahan, Grafton, Mass.; Thomas M. Shimei, Franklin, Mass.; Kevin R. Kearney, Worcester, Mass.

[73] Assignee: Amoco Corporation, Chicago, Ill.

[21] Appl. No.: 136,654

[22] Filed: Oct. 14, 1993

[51] Int. Cl.⁵ .................. G01N 21/24; G01N 33/16
[52] U.S. Cl. .............................. 422/64; 422/61;
    422/63; 422/65; 422/67; 422/82.08; 422/100;
    422/102; 435/299; 435/300; 435/301; 435/316;
    436/43; 436/47; 436/48; 436/49; 436/164;
    436/165; 436/166; 436/172; 436/174; 436/180
[58] Field of Search ............... 422/63, 64, 65, 67,
    422/81, 82.08, 100, 104, 102, 61; 436/43, 47, 48,
    49, 56, 164, 165, 166, 172, 174, 179, 180, 805;
                                  435/299, 300, 301, 316

[56] References Cited

U.S. PATENT DOCUMENTS

| Re. 29,725 | 8/1978 | Johnson et al. | 435/12 |
|---|---|---|---|
| 4,038,030 | 7/1977 | Albright et al. | 422/61 |
| 4,595,562 | 6/1986 | Liston et al. | 422/65 |
| 4,678,752 | 7/1987 | Thorne et al. | 435/291 |
| 5,055,262 | 10/1991 | Sakagami | 422/64 |
| 5,089,233 | 2/1992 | DeVaney, Jr. et al. | 422/99 |
| 5,098,660 | 3/1992 | DeVaney, Jr. | 422/99 |
| 5,154,888 | 10/1992 | Zander et al. | 422/58 |
| 5,154,889 | 10/1992 | Mursishi | 422/65 |
| 5,158,895 | 10/1992 | Ashihara et al. | 436/526 |
| 5,176,880 | 1/1993 | Iwasaki et al. | 422/63 |
| 5,178,834 | 1/1993 | Kagayama et al. | 422/65 |
| 5,192,505 | 3/1993 | Sakagami | 422/64 |
| 5,192,506 | 3/1993 | Kuresky et al. | 422/64 |
| 5,207,987 | 5/1993 | Kureshy et al. | 422/67 |
| 5,217,443 | 6/1993 | Oxley | 604/317 |
| 5,229,297 | 7/1993 | Schnipelsky et al. | 436/94 |
| 5,254,479 | 10/1993 | Chemelli | 436/180 |
| 5,281,540 | 1/1994 | Merkh et al. | 436/530 |

*Primary Examiner*—James C. Housel
*Assistant Examiner*—Long H. Le
*Attorney, Agent, or Firm*—Thomas W. Tolpin

[57] ABSTRACT

A dependable cost-effective clinical analyzer machine provides an efficient and easy-to-use diagnostics instrument and process to accurately, rapidly and automatically test and analyze samples in test packs for an analyte. In the clinical analyzer machine, remote-controlled trams transport test packs containing loading-/unloading station to a processing/testing station via a carousel and vice versa. In the processing station, a special processor with mechanically-operated rollers mixing shoes, wastegate assembly, magnets, clamp plate and a thermal sealer, process samples in test packs with various reagents to detect an analyte. The carousel holds the test packs during incubation periods and rotates the tested disposable packs past an optical reader which optically senses the presence of an analyte in the sample. Bar code readers are provided to assist in identification of the test pack, patient and sample.

10 Claims, 24 Drawing Sheets

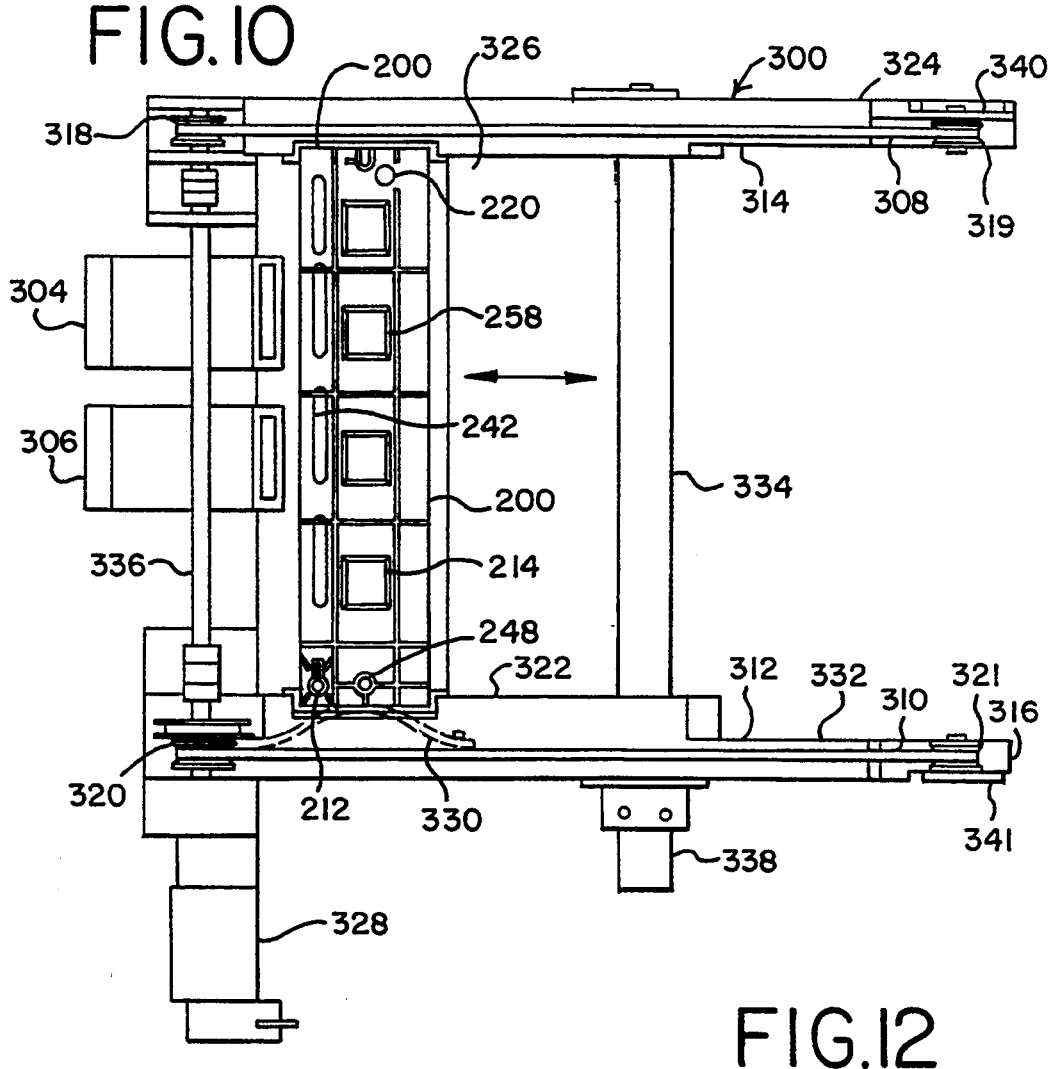
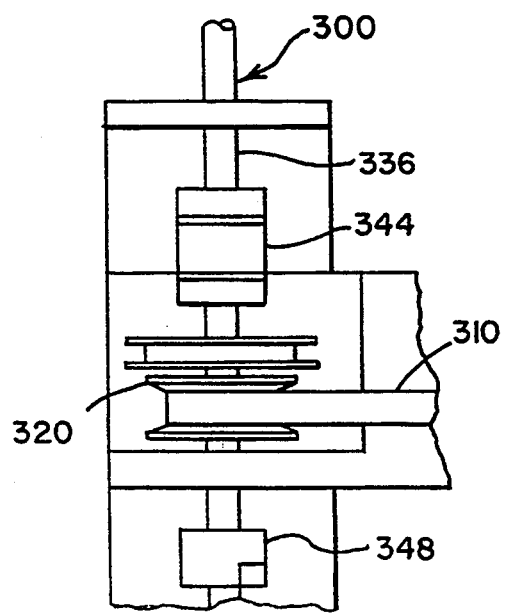
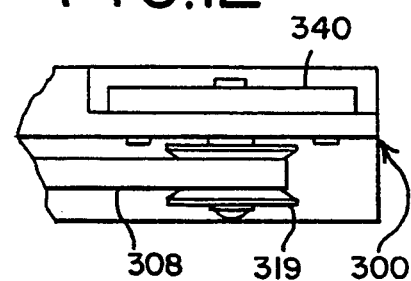
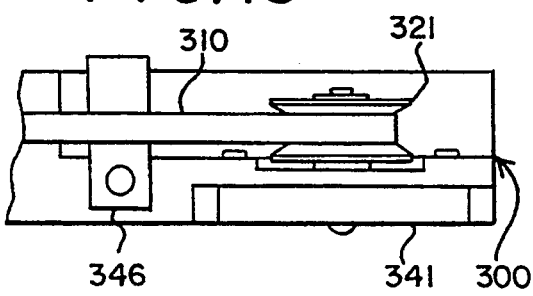

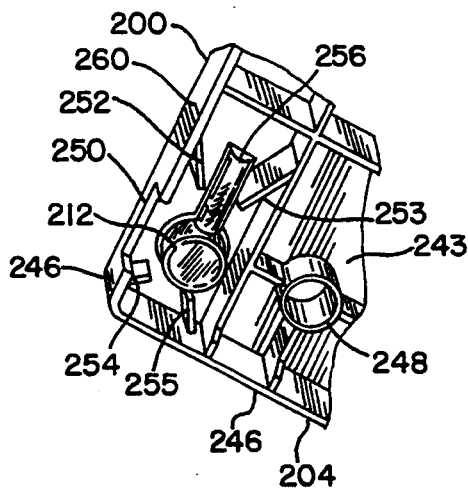
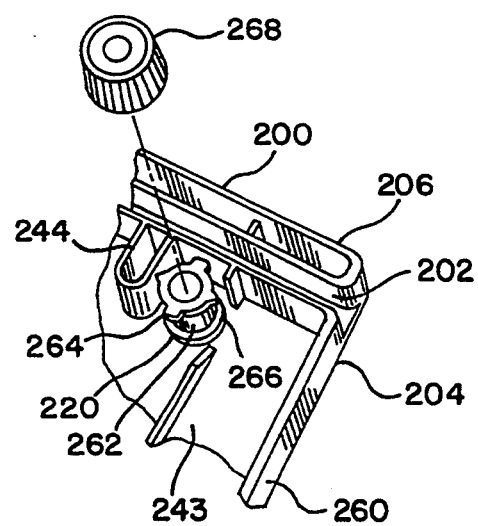
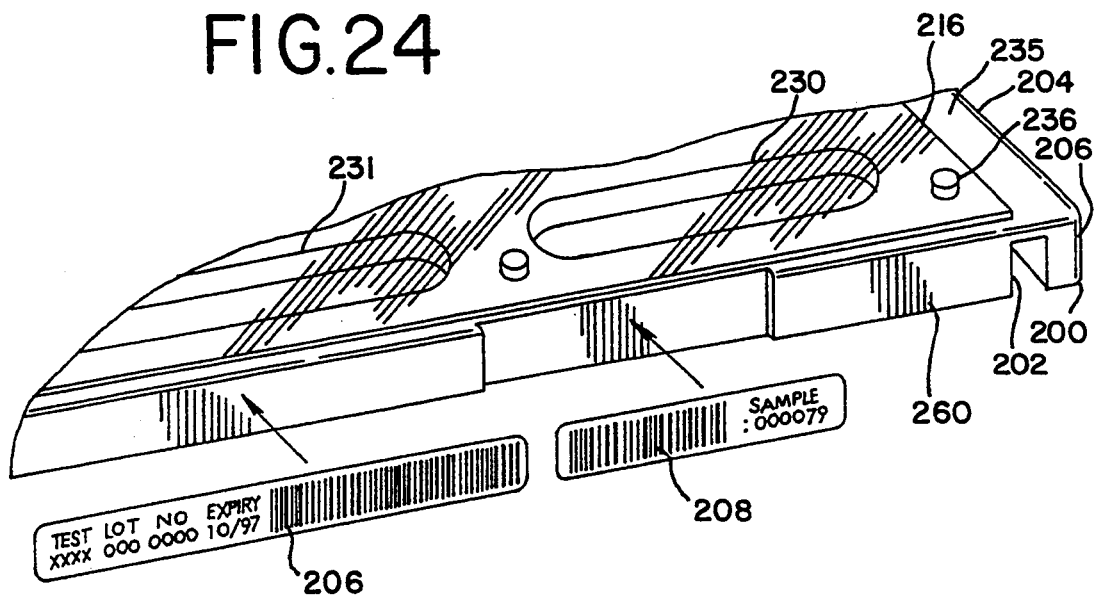

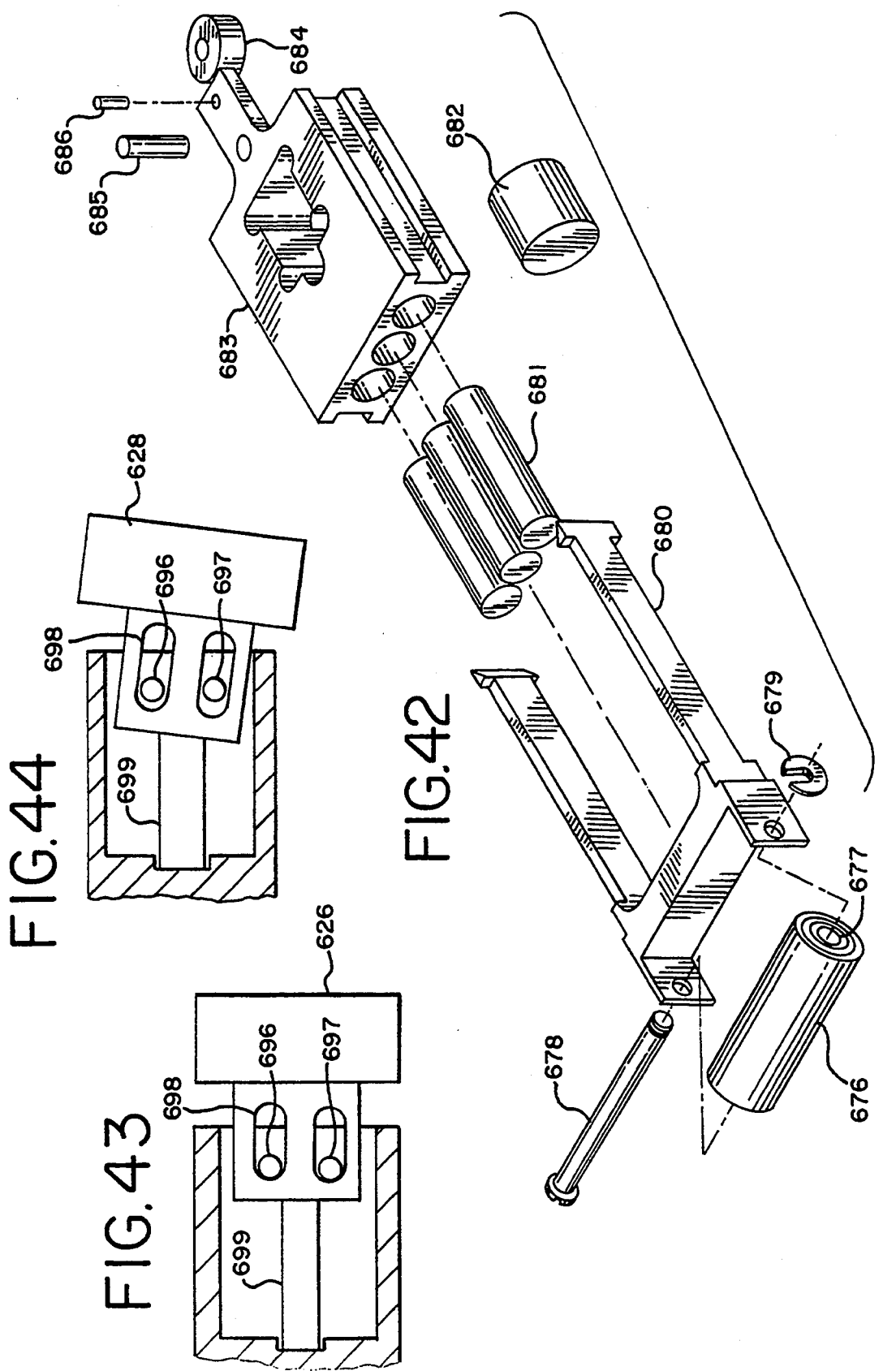

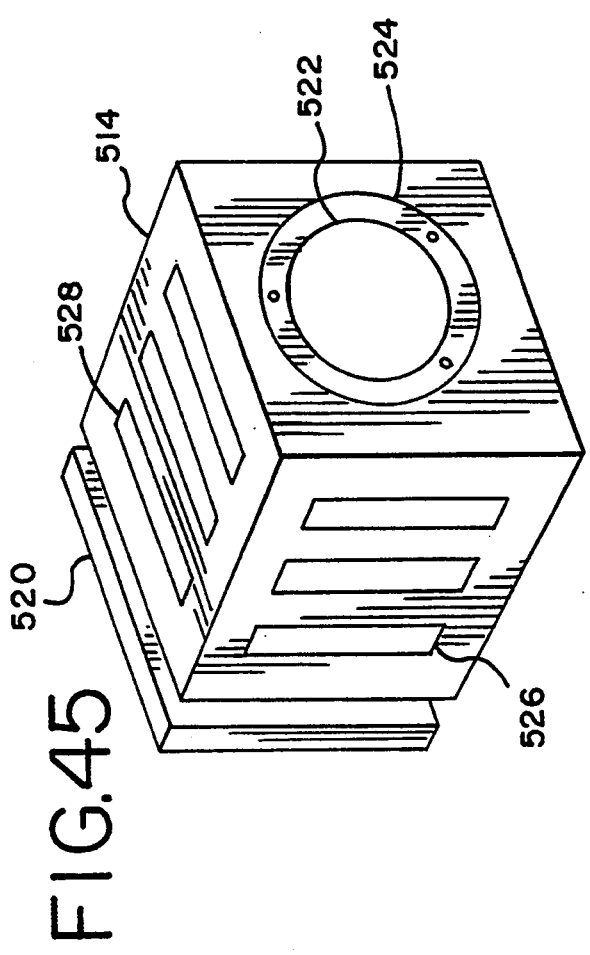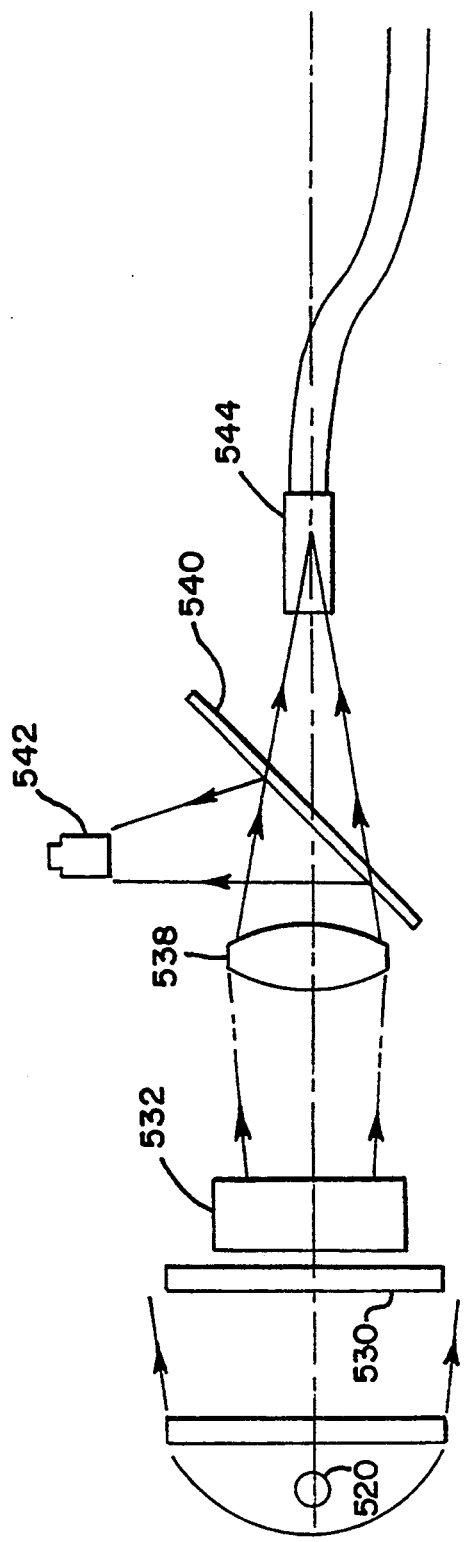

DIAGNOSTICS INSTRUMENT

BACKGROUND OF THE INVENTION

This invention pertains to a clinical analyzer and, more particularly, to an automated diagnostics instrument and process for analyzing samples in test packs for an analyte. Detection of infectious microorganisms is primarily accomplished by either culture techniques or by antibody detection techniques. Culture techniques have been routinely used for many decades and in combination with some biochemical tests are capable of identifying most common bacterial pathogens. Antibody detection techniques came into routine laboratory use about two decades ago. Although generally more sensitive than culture techniques, antibody techniques generally are only useful to diagnose a limited group of microorganisms.

Classical culture techniques, which is still in use today, involves inoculating a human tissue or fluid sample onto a special nutrient media plate(s), using sterile techniques. The media used are based on their ability to support specific microorganisms that could be in the sample. Once the media plates are inoculated, they are incubated for 12-24 hours. Thereafter, plates are macroscopically examined for growth of the microorganism(s). If growth is present, one or two more biochemical tests are performed to identify the organism based on its known metabolic reactions. Biochemical identification involves inoculating specific material with a pure isolate of the bacteria. The biochemical reactions are incubated for 24-48 hours and then observed for presence of a positive or negative chemical reaction. Often a slide is also prepared for microscopic examination that will aid in identification. Plates that did not produce growth initially are incubated for a total of 48-72 hours to clearly determine their negative status. During the 1980's, methods were developed to produce more rapid results. In these methods, after the first 24 hour growth, isolates are inoculated in rapid reaction biochemical materials. Preliminary identification can be available as quickly as four hours on some of these methods with full identification within 12-24 hours for primary culture. The principle of the majority of the rapid tests is the same as classical biochemical methods but has been adapted to a rapid, automated or semi-automated format. Mycobacterium tuberculosis (M.Tb) the causative agent of Tuberculosis (TB), is detected by classical cultural techniques. The main difference is that M.Tb is a very slow growing microorganism, taking four to six weeks to grow and identify,. When the sample is received, a slide is prepared for microscopic examination, which can give a presumptive result if a microorganism looking like TB is seen on the slide. This is not a reliable method but, if positive, may give the physician some indication that the patient could possibly have TB.

Antibody detection methods take advantage of antibodies. An antibody is a protein molecule that is produced in the normal immune system as immune response to foreign (non-self) material. The foreign material is called an antigen. Producing an immune response is called antigenic. Many microorganisms are antigenic to the human body, so antibodies are produced when exposure to the microorganism has occurred.

The original antibody detection method involves the detection and often quantification of the antibody in the blood of the patient. The principle of the method is based on the very specific binding of the antibody to the antigen. If both the antigen and antibody are present, they will form a chemical bond analogous to a lock and key. In the simplest of these methods, the blood sample, potentially containing the antibody, is mixed with the antigen that has a radioactive detector built into its structure. If the antibody and antigen are both present, they will bond producing a radioactive signal indicating a positive reaction. If the antibody is not present in the sample, the antigen will be washed away and the reaction will not produce a radioactive signal. Due to the potential hazards of dealing with radioactive materials, the original methods have largely been replaced by enzymatic detectors that show a color reaction when positive. Other methods, based on the antibody-antigen bond have been developed that combine multiple antibodies and antigen systems to increase specificity. Since they are proteins, antibodies can also be detected by common protein detection methods, such as electrophoresis.

In the past, clinical analyses of analytes in a tube or test pack have been tedious, time-consuming, often taking days to obtain results, manually intensive, and often unreliable. It is, therefore, desirable to provide an improved diagnostics instrument and process which overcomes most, if not all, of the preceding problems.

SUMMARY OF THE INVENTION

An improved automated diagnostics instrument is provided for rapidly, efficiently and effectively analyzing samples in test packs for an analyte. Advantageously, the novel automated diagnostics instrument is easy to use, reliable and safe. Desirably, the test packs are automatically, quickly and repeatedly analyzed by the user-friendly diagnostics instrument without any human contact of the sample in the closed test packs to avoid contamination and assure dependability and confirmation of the assay results.

To this end, the automated diagnostics instrument comprises a movable processing assembly which contacts samples in test packs with at least one reagent to form an optically detectable analyte. The movable processing assembly assists in assuming the test packs. Nucleic acid assays are preferred for best results, although in some circumstances it may be desirable to use immuno assays or other assays. The processing assembly can move vertically, horizontally, longitudinally, laterally and in other directions as desired. The processing assembly can have at least one roller and/or reciprocatable shoe to help mix the reagents in the test packs. The optically detectable analytes in the test packs are optically sensed and detected by an optical detection assembly.

Spaced apart from the processing assembly is a test pack carrier assembly to carry the test packs. The test pack carrier assembly can be in the form of a turntable, carousel, belt conveyor, or other carrying mechanism or holding device. A motor or other dynamic moving means are provided to move the test pack carrier assembly and the optical detection assembly relative to each other so that the test packs are sensed by the optical detection assembly at timed intervals. In the illustrative embodiment, both the test pack carrier assembly and the optical detection assembly are moveable and driven by motors.

The invention also provides an outstanding automated diagnostics process for analyzing samples and test packs for analytes. In the process, optically detectable analytes are formed by sequentially expressing, rolling and mixing reagents with samples in reaction areas of a set of closed disposable test packs. Waste portions of the samples are separated from the analytes in the test packs and rolled or otherwise passed into waste pouches in the test packs, which are subsequently sealed. During processing, the temperature of the test packs are controlled to enhance the reliability of the tests. The test packs are repeatedly moved past a scanning station where they are optically scanned and sensed for the optically detectable analytes.

In the preferred process, blisters of reagents in the closed disposable test packs are compressed and seals are burst with reciprocating compact members, such as shoes, or by rollers. Waste portions of the samples are magnetically separated from the analytes and moved into waste pouches which are subsequently heat sealed. Preferably the test packs are rotated in an upright position past the scanning station, by a carousel.

In the preferred form, the automated diagnostics instrument has a special processing station assembly comprising a movable saddle assembly which rides upon and engages the test packs. The movable saddle assembly expresses and mixes reagents with samples in the test packs to form optically detectable analytes and separates and seals waste portions of the samples from the analytes and waste pouches of the test packs. In the illustrative embodiment, the saddle assembly includes a roller subassembly, a shoe and mixer subassembly, and a sealer subassembly which are operatively connected to each other. The roller subassembly mixes reagents and samples in the reaction area of the test packs and moves the background material comprising waste portions of the samples to waste pouches in the test packs. The shoe and mixing subassembly manipulate and mix reagents in blisters and test packs and break the blisters to express reagents from the blisters to the reaction areas of the test packs. The sealer subassembly seals empty reagent blisters, vacated reaction areas and filled waste pouches in the test packs. Preferably, the processing station assembly also includes a clamp plate assembly to hold and support the test packs in an erect position. Pneumatically operated magnets are operatively connected to the clamp plate assembly to engage the test packs. The pneumatically operated magnets magnetically attract metallic beads (metallic particles) in the test packs carrying the optically detectable analytes. In the illustrative embodiment, the processing station assembly also includes a wastegate assembly to temporarily close the waste pouches in the test packs.

Desirably, the processing station assembly provides the assaying techniques and mechanisms for nucleic acid probe assaying of the samples of test packs by reversible target capture (RTC). The preferred assaying techniques include: hybridizing probes to nucleic acid sequence targets comprising the analytes in the samples; capturing the hybridized probes and targets on the beads; magnetically removing the beads from suspension in the test packs; washing the background material from the samples: releasing targets from the beads with an eluant; and, replicating detector probes with Q-beta replicase enzyme for amplification.

The automated diagnostics instrument has a sensing assembly to optically detect the optically detectable analytes in the test packs. In the preferred form, the sensing assembly includes a read head assembly to detect hybridized fluorescent analytes. A carousel assembly is provided to hold an array of test packs in a generally upright position and to intermittently, repeatedly and accurately move and rotate the test packs past the optical sensing assembly so that the optical sensing assembly can optically detect changing transitory optical characteristics of the analytes in the test packs at selected periodic intervals, as well as confirm the diagnosis. Temperature controls are provided to control the temperature of the samples in the test packs during processing, assaying, diagnostics and reading. The temperature controls include incubator controls, preferably located about the carousel to heat the array of upright test packs in the carousel. The temperature controls also include heating elements about the processing station assembly to heat the test packs in the processing station.

The automated diagnostics instrument also has a load door station for ingress and egress (entrance and exiting) of the test packs. A load tram is provided to move and transport the test packs from the load door station to the carousel and vice versa. The processing tram is provided to move and transport the test packs from the carousel to the processing station and vice versa. Preferably, at least one of the trams includes a belt conveyor. A shuttle is secured to the belt conveyor to detachably hold the test packs in an upright position.

While various types, shapes and sizes of test packs and other means for containing samples can be used in the diagnostics instrument, for best results it is preferred that the test packs comprise closed disposable packs mounted upon impact-resistant trays providing backing plates. The closed disposable packs have burstable blisters containing reagents for the desired tests. Desirably, the closed disposable packs are made of flexible, light-transmissible plastic, such as transparent or translucent plastic, with viewable portions to view the reagents and samples within the interior of the packs. The trays providing the backing plates matingly engage and rigidly secure the closed disposable packs. In the preferred form, the trays have docking mechanisms with read cells and optically transparent windows to permit viewing of the optically detectable analytes in the closed disposable packs. The test packs also preferably have a thermally conductive plate to conduct heat from the heating controls to enhance amplification. In the illustrative embodiment, the trays have laterally slotted, upper carrier portions and lower carrier portions to engage the shuttle and carousel. Each of the trays is encoded with indicia corresponding to a desired test and identification of the sample and patient. Desirably, the automated diagnostics instrument includes an indicia reader assembly, such as a bar code reader, positioned in proximity to the load door station to optically read the indicia, bar codes, and identification of the trays.

One or more central processing units, such as a computer with a display screen, can be provided to receive signals from the bar code reader or indicia reader, as well as the optical read head of the sensing assembly. Desirably, the central processing unit is operatively connected to the processing station to control the sequence of operations of the processing station assemblies and subassemblies.

A more detailed explanation of the invention is found in the following description and appended claims taken in conjunction with the drawings.

BRIEF DESCRIPTION OF THE DRAWINGS

FIG. 10 is a front view of the load tram and bar code readers of the automated diagnostics instrument with a test pack loaded in a shuttle of the load tram;

FIG. 11 is an enlarged fragmentary view of the left lower portion of the load tram;

FIG. 12 is an enlarged fragmentary view of the right upper portion of the load tram;

FIG. 13 is an enlarged fragmentary view of the right lower portion of the load tram.

FIG. 14 is a front view of a processing shuttle carrying a test pack in a processing tram of the automated diagnostic instrument;

FIG. 15 is an enlarged fragmentary view of the left upper portion of the processing tram;

FIG. 16 is an enlarged fragmentary view of the left lower portion of the processing tram;

FIG. 17 is an enlarged fragmentary view of the right lower portion of the processing tram;

FIG. 22 is a perspective view of a read cell of the test pack as viewed from the back of the test pack;

FIG. 23 is an assembly view of a cap and sample port of the test pack as viewed from the back of the test pack;

FIG. 24 is an assembly view of bar code stickers and portions of a tray providing part of the back plate of the test pack;

FIG. 42 is an assembly view of a roller assembly of the automated diagnostics instrument;

FIG. 43 is a cross-sectional view of a sealer assembly of the automated diagnostics instrument;

FIG. 44 is a cross-sectional view of another position of the sealer assembly.

FIG. 45 is a perspective view of the lamp housing of the optical reader:

FIG. 46 is a diagrammatic view of the excitation channel components of the optical reader;

DETAILED DESCRIPTION OF THE PREFERRED EMBODIMENT

Overview

Figure 1:
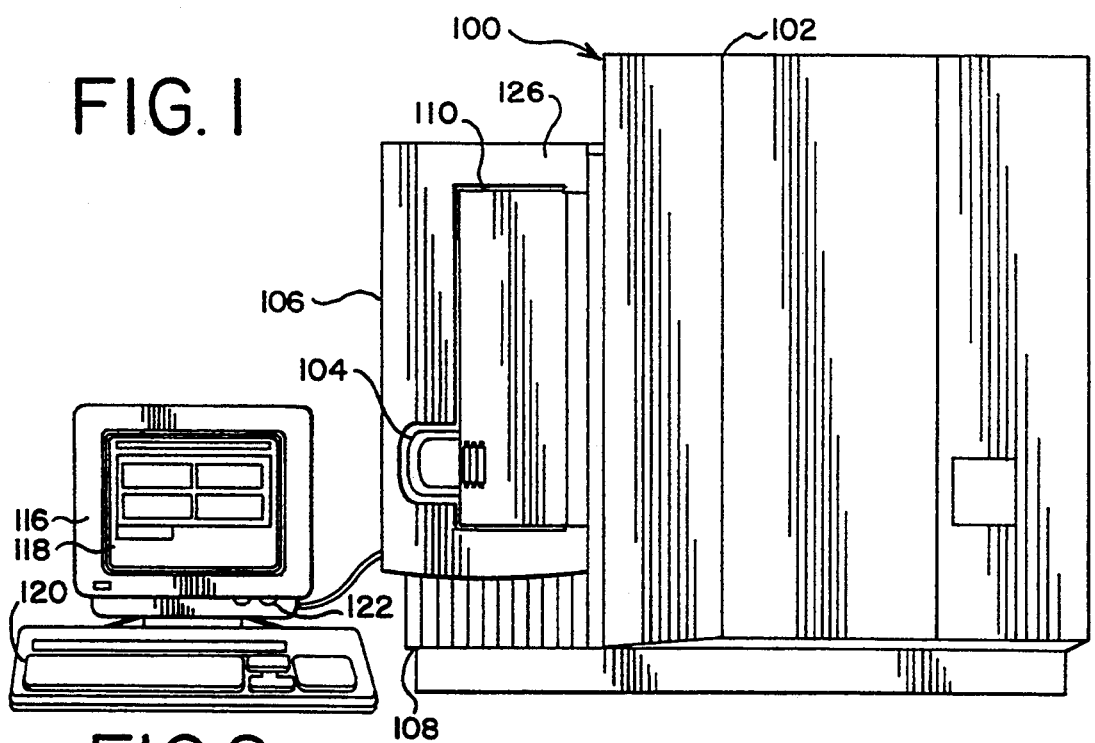
FIG. 1 is a front view of the automated diagnostics instrument in accordance with principles of the present invention.

An automated diagnostics instrument 100 (FIG. 1) provides a clinical analyzer and automatic diagnostics machine to analyze samples for analytes in test packs 200 (FIG. 2), also referred to as test specific packs (TSP). The automated diagnostics instrument is a stand-alone unit that automates a series of reactions, processes, tests and analytes on the test packs. The automated diagnostics instrument performs all reactions involved in an assay in the test packs.

Figure 18:
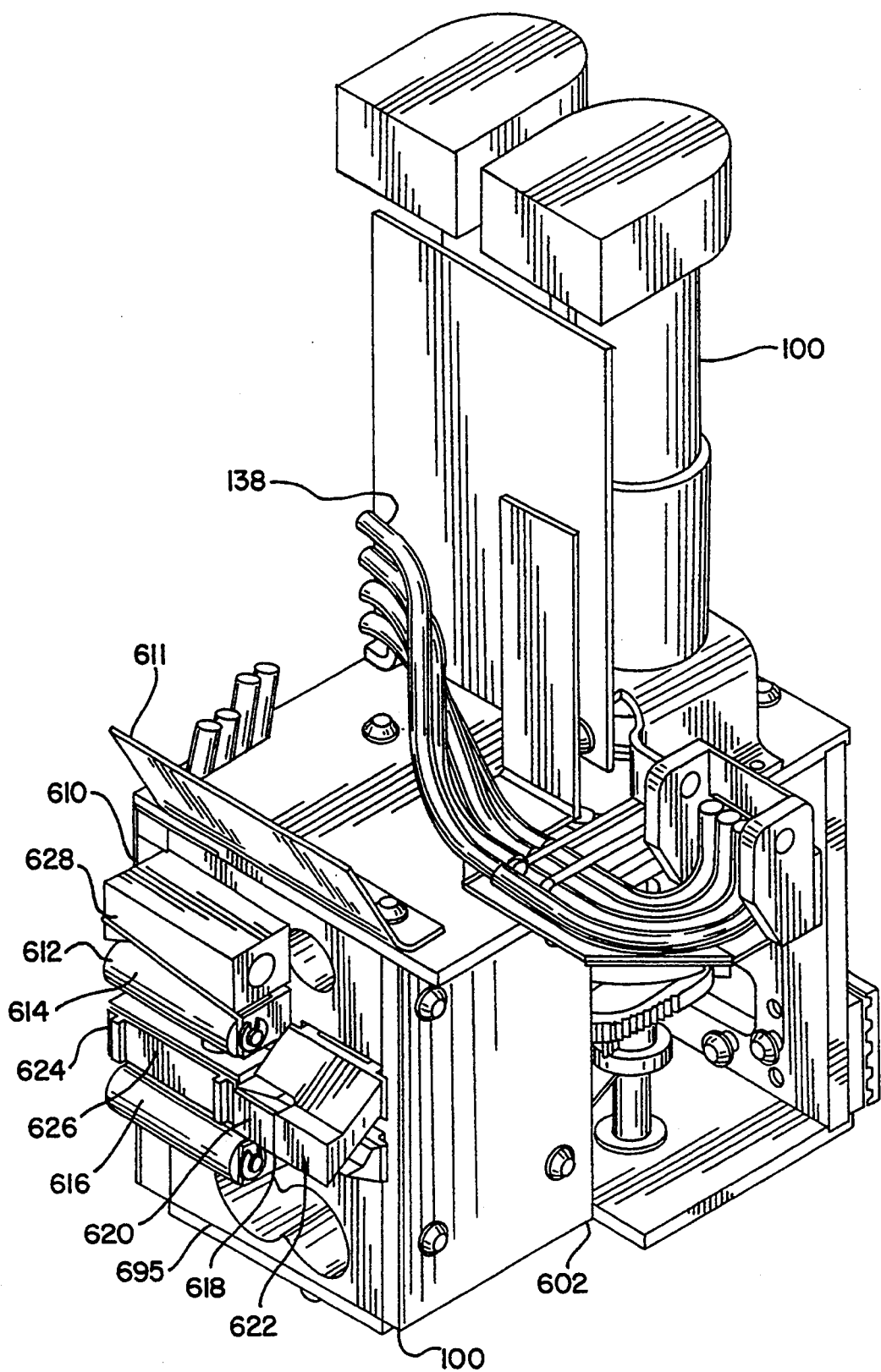
FIG. 18 is a perspective view of the saddle assembly of the automated diagnostics instrument.
Figure 19:
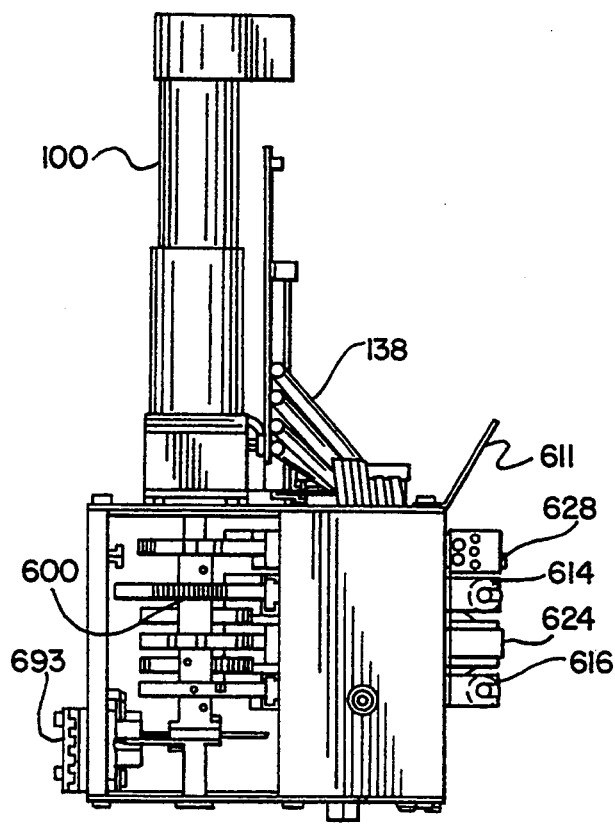
FIG. 19 is a side view of the saddle assembly.
Figure 20:
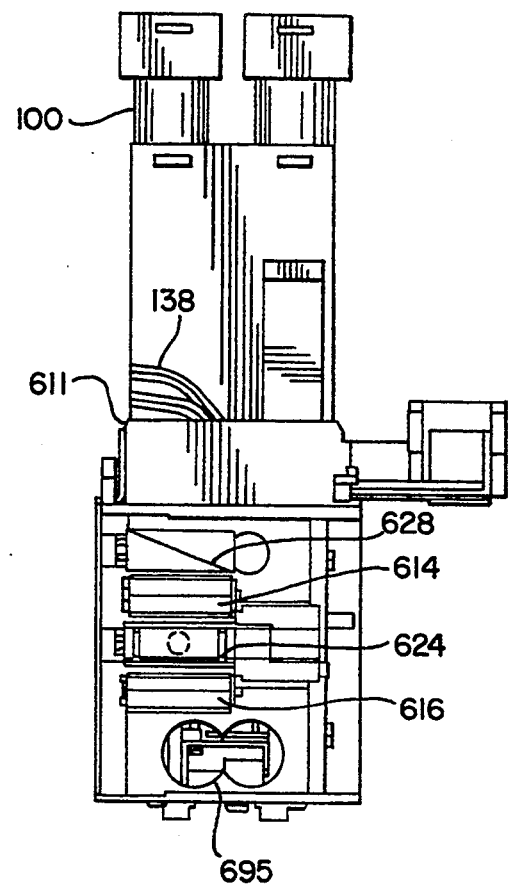
FIG. 20 is a front view of the saddle assembly.
Figure 21:
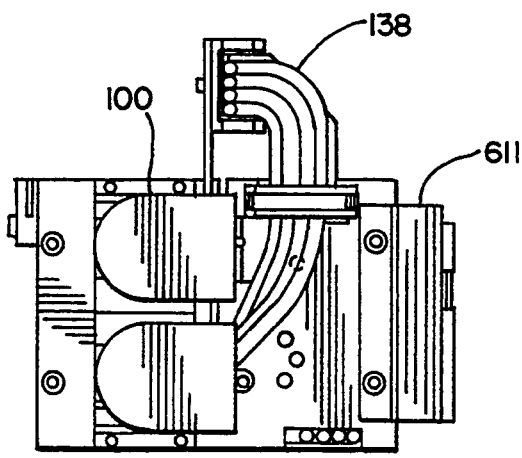
FIG. 21 is a top view of the saddle assembly as viewed from the rear of the automated diagnostics instrument.
Figure 25:
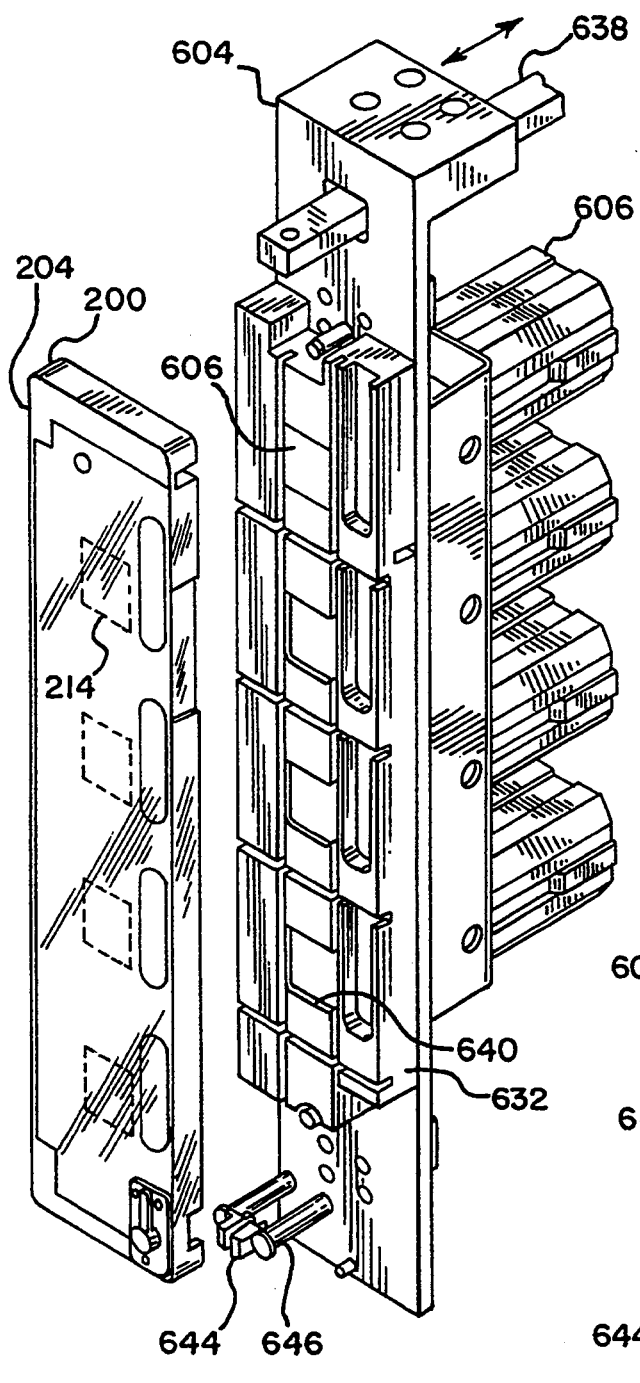
FIG. 25 is an assembly view of a test pack and clamping plate assembly of the automated diagnostics instrument.
Figure 27:
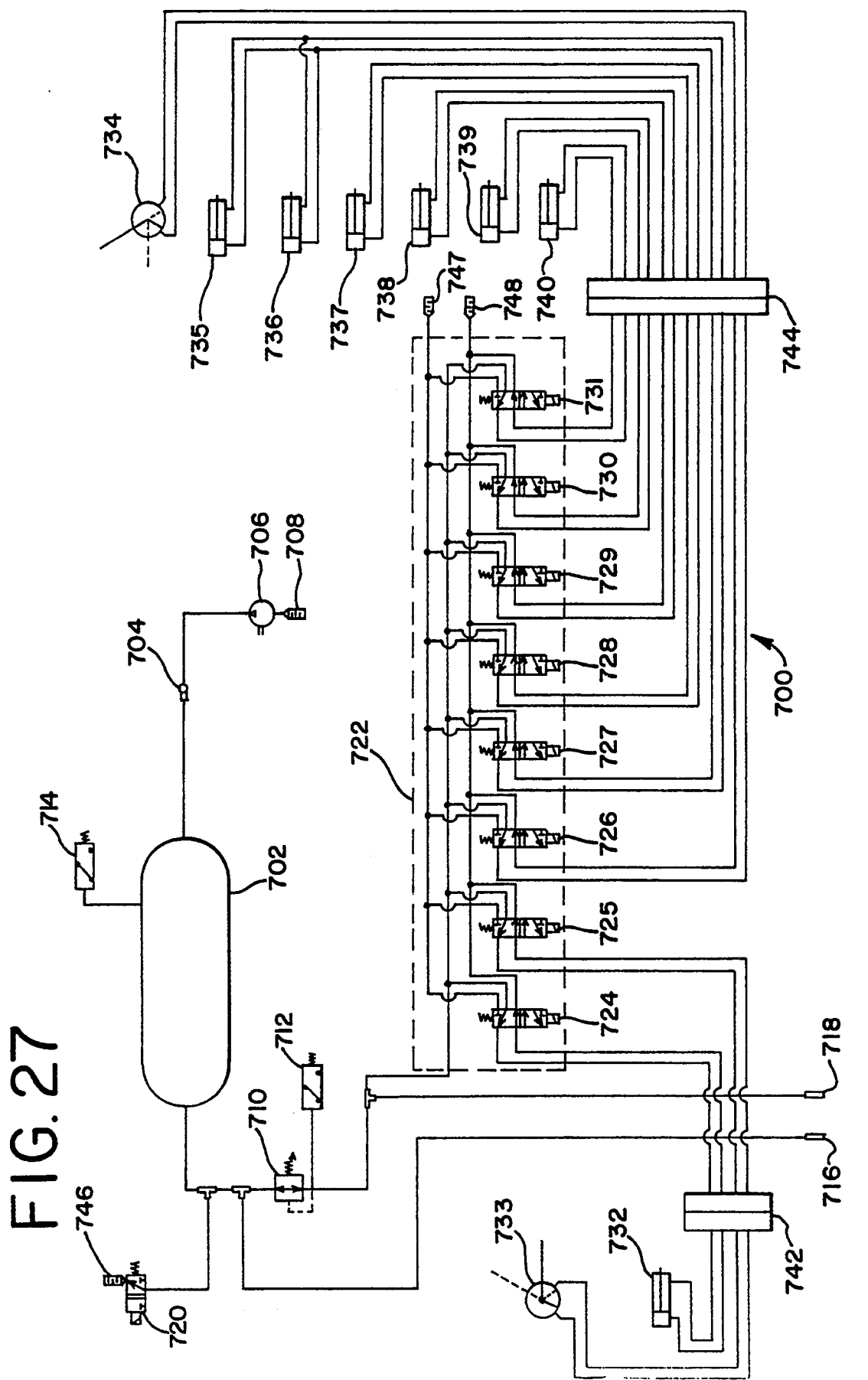
FIG. 27 is a pneumatic circuit diagram of the automated diagnostics instrument.
Figure 29:
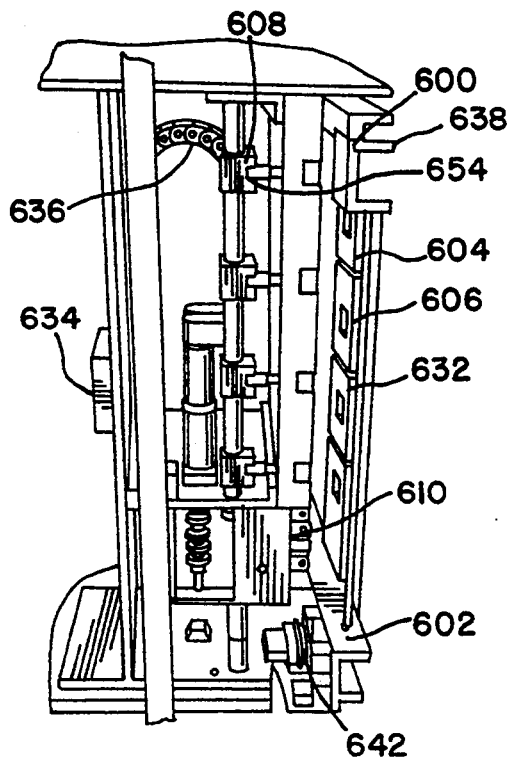
FIG. 29 is a side view of the processing assembly.
Figure 31:
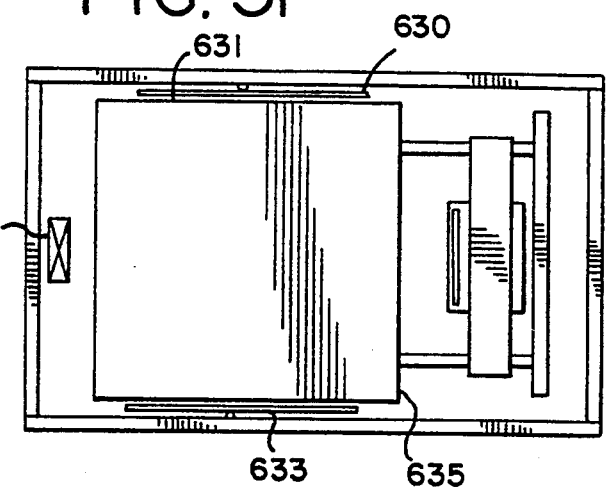
FIG. 31 is a diagrammatic view of a processing heating system of the automated diagnostics instrument.

The automated diagnostics instrument has: a housing or case 102 (FIG. 1), panels including a front panel 104 and side panel 106, a central processing unit 108, a load door 110, trams including a load tram 300 (FIG. 9) and processing tram 302, bar code readers 304 and 306 (FIG. 10), a rotating carousel assembly 400 (FIG. 9), also referred to as a carousel, an optics module 500 operatively connected by fiber optics to an optical reader or scanner 502 with a read head 504, a processor 600, and a processing station 602. The processing station 602 has a processor 600 with: processor clamp plate assembly 604 (FIG. 25) and a processor magnet assembly 606 (FIG. 29), a processor wastegate assembly 608 (FIG. 29), and a processor saddle assembly 610. The processor saddle assembly 610 has a roller subassembly 612 (FIG. 18) with upper and lower processing rollers 614 and 616, a mixer or shoe subassembly 618 with mixers comprising reciprocating shoes 620 and 622, and a sealer subassembly 624 with a side sealer 626 and a reaction area sealer 628. The processor 600 is pneumatically controlled by a pneumatic circuit and system 700 (FIG. 27). Test packs in the processing station are heated by a processor heating system 630 (FIG. 31). Test packs in the carousel 400 (FIG. 9) are heated by a carousel heating system 402. Electrical controls are provided to control and regulate the speed and movement of the trams, carousel, read head and cams in the saddle assembly as discussed below.

A locking pin assembly 112 (FIG. 37) has a movable locking pin 115 (FIG. 37) to releasably secure the carousel at various locations. The locking pin assembly operates to position the test pack in front of the read head so that the read head can read the optically detectable analyte in the read cell. The locking pin assembly further assists in positioning and aligning the test packs for entry into or exit from the load tram and processing tram.

Housing and Panels

The housing 102 (FIG. 1) of the diagnostics instrument can be of reinforced metal construction or of impact-resistant plastic, and can be placed on a lab bench, table or counter. The front panel 104 of the automated diagnostics instrument contains four LEDS (light-emitting diodes): power, load, unload and active. The LEDS indicate the automated diagnostics instrument's current status. Power is illuminated when the automated diagnostics instrument is turned on. The load LED is illuminated when test packs can be loaded. The unload LED is illuminated when a test pack is ready to be unloaded. The active LED is illuminated when the load door 110 cannot be opened.

The side panel 106 (FIG. 1) of the automated diagnostics instrument provides power to the entire instrument and allows the instrument to communicate with other devices. The side panel has: a disk drive, four interface ports, a parallel interface, a serial interface, a video port, connector socket, a power switch, and a fuse. The disk drive copies information to diskettes. Four interface ports can connect components to the automated diagnostics instrument. A parallel interface can be provided for an optional printer. A serial interface can be provided to connect to another computer. A video port can be provided for a monitor 116 with a computer screen 118. A round connector socket can be provided for a computer keyboard 120. A power socket connects to the three-pronged power cord. An ON/OFF power switch turns the automated diagnostics instrument power on and off. A fuse protects the instrument from power surges.

The housing 102 provides an external case which restricts the emission of radio frequencies from the electronic components within the enclosure. An insulating enclosure helps to maintain a constant temperature within the automated diagnostics instrument, ensuring that the test packs encounter the correct temperature in the carousel, processing station, and trams.

Central Processing Unit

The monitor 116 (FIG. 1) and keyboard 120 work together to allow the operator to view and enter information about patient tests and instrument operation. The monitor 116 can be a standard 14-inch VGA color monitor. Dials 122 along the bottom of the monitor 116 adjust the contrast and brightness of the display. The keyboard 120 lets the operator type in information, such as a patients name, and press special function keys to display specific information on the monitor, such as a report on patient test results. The diskette drive on the side panel allows the operator to copy patient results to removable diskettes (floppy disks). The drive can accept high-density, 3.5 inch DOS-formatted diskettes. The automated diagnostics instrument can also include an optional printer and can be used in conjunction with a sample processor. The automated diagnostics instrument can be used with any printer that has a parallel interface, can be based on the Centronics standard, is Epson Ⓡ-compatible, and can provide an 80-column output.

The electronics module 124 (FIG. 9) at the rear of the automated diagnostics instrument contains microprocessors comprising two computers that run the various internal assemblies. The test results computer communicates with the monitor, keyboard and optional printer. Patient test results and instrument performance records are stored on this computer's hard drive along with the programs that let operators view and enter information on the monitor. The system computer schedules the processing work for each test pack and moves the various assemblies within the automated diagnostics instrument. The programs that run the assemblies and make sure that all processing activities occur on schedule are stored on this computer's hard disk. The use of two computers provides an interface which ensures that the system computer is not affected by the operator's actions. The system computer is devoted to running the diagnostics instrument, so that all the timing of all processing actions is exact, precise and accurate. The circuit boards used to determine or monitor overall function of the diagnostics instrument reside within the electronics module 124.

The electronics module 124 of the automated diagnostics instrument can include two IBM compatible PC motherboards in a master-slave configuration in order to provide the microprocessing power in the automated diagnostics instrument. The master system can comprise a 33 Mhz 386 motherboard with a hard disk, floppy disk drive and VGA graphics. The slave motherboard can be a 33 Mhz 386 with VGA graphics. An interface card can contain an EPROM with slave software on it, and provides a bus to the main system motherboard. Four main electronics boards plug into the system motherboard which then distributes signals and power to the diagnostics instrument. The four main boards are: (1) digital board, which decodes the servo motor encoders and reads the opto switches; (2) servo board, which provides power drivers for the motors and heaters; (3) a pneumatics board, which provides drivers for the pneumatics valves and pump and regulates the heater mat sensors; and (4) reader electronics. The main function of these four boards is to provide sensors and drivers which form a number of closed loop servo systems. Additional boards can include a programmable constant current driver to power the sealers and reader photodiode preamplifier. The bar code readers communicate with the slave via an interface. The electronic module 124 (FIG. 9) comprising the computers, keyboard and display screen are wired to and receive signals from the bar code reader and read head. The computers are also connected to the processing station and assembly to control the sequence of operations of the processing station and assembly in accordance with the necessary sequence of steps to conduct the desired tests of the samples in the test packs in the processing station.

Load Door

Figure 2:
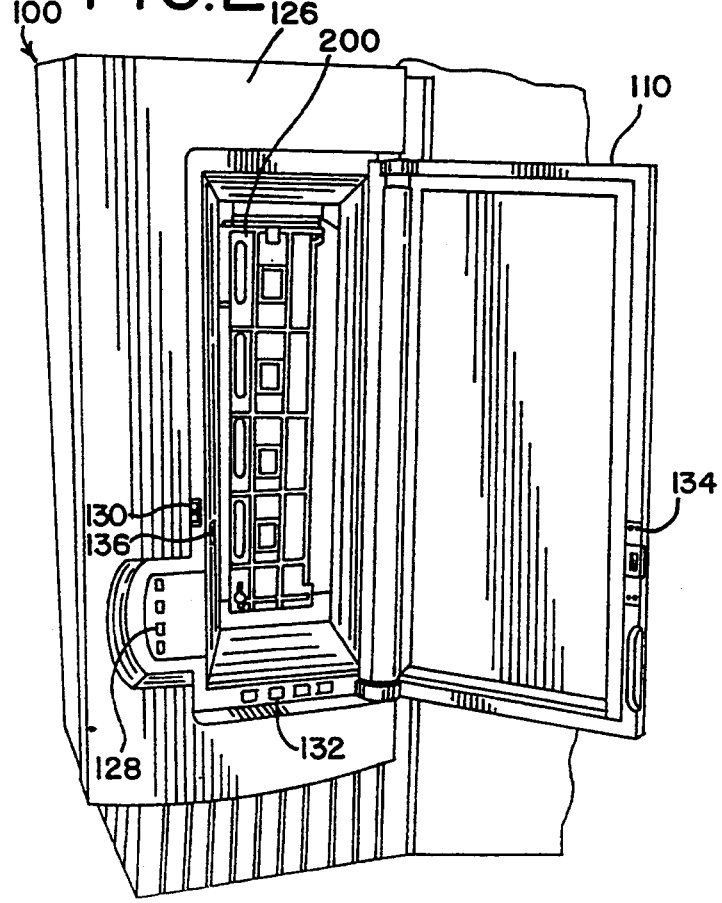
FIG. 2 is a perspective view of the load door of the automated diagnostics instrument loaded with a test pack.
Figure 3:
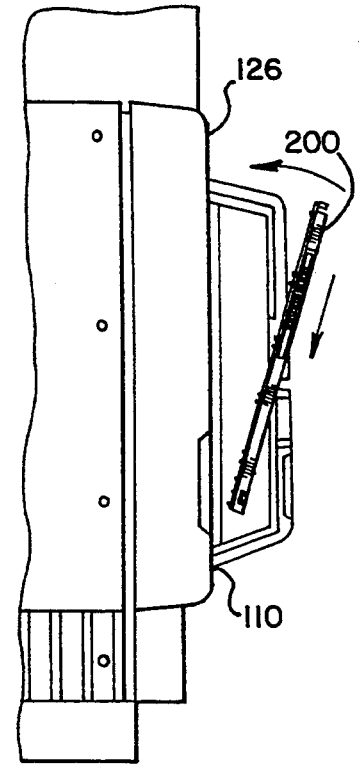
FIG. 3 is a side view of the load door being loaded with a test pack.

The load door 110 (FIG. 2), also referred to as a loading door or a load door assembly, provides a loading station 126 where the operator loads and unloads test packs 200. The load door opens to reveal the load chamber, where the operator inserts the test packs. The operator can load one test pack at a time as shown in FIG. 3 and closes the load door after loading each test pack. Closing the load door causes the automated diagnostics instrument to begin processing the test pack. Desirably, the operator can only open the load door when the instrument is ready to receive or unload test packs. The load door is closed and locked when temperature-sensitive and light-sensitive operations are occurring within the automated diagnostics instrument.

The load door opens an entrance passageway for ingress and entrance of the test packs to be tested and diagnosed in the diagnostics instrument. The load door also opens and closes an exit passageway for egress and exiting of the tested diagnosed test packs.

The load door 110 (FIG. 2) comprises an assembly which includes: a light emitting diode (LED) status indicator and label 128, a door lock 130, a proximity actuation switch 132, a load door strike plate 134, and a retention magnet 136. The door lock 130 secures the load door 110 after the test pack has been loaded therein for controlled handling and uninterrupted protocols. The LED indicator 128 shows the status of the diagnostics instrument 100. The retention magnet 136 is provided to assist and facilitate locking of the load door. The actuation proximity switch 132 disables the load tram motor drive when the load door is open. The load door is designed to be opened using one hand in position while the other holds the test pack. The load door can only be opened when the door lock 130 is off and the LED indicator 128 for load is lit up. The test pack is loaded into the load station area by placing the bottom edge of the test pack into the lower load shuttle of the load tram and pushing down on the lower spring plate. The top edge of the test pack is then pushed into the top load shuttle. Once loaded, the load door is closed and the magnet and lock are activated before the next operation. Unloading of the processed, tested test pack from the load door is the reverse of loading.

Trams

The load and processing trams 300 and 302 (FIG. 9) comprise conveyors that move the test pack around in the automated diagnostics instrument. The load tram 300 moves the test pack between the load door and the carousel 400. The operator loads a pack directly into the load tram 300 and removes the processed test pack directly from the load tram. The processing tram 302 moves the test pack between the carousel 400 and the processing station 602. Each tram 300 and 302 has a set of continuous drive belts 308 and 310 (FIG. 10)—one on top and one on the bottom—which move together as a unit. In order to cradle the test pack in the tram, a bracket 312 on the bottom drive belt 310 lines up under a bracket 314 on the top drive belt 308. The brackets 312 and 314 are permanently attached to the drive belts 308 and 310, fit the test pack dimensions, and move as a pair when the drive belts move. To further support the test pack when it moves, a rail 316 in each tram passageway hooks up with a groove 202 (FIGS. 6, 23 and 24) in the test pack backplate 204. The test pack is conducted along this rail as it is moved. Each drive belt 308 and 310 (FIG. 10) is moved by its own pulley 318–321, which are powered by a motor that provides smooth and accurate movement.

As indicated above, the load tram, also referred to as a loading tram, and process tram, also referred to as a processing tram, each have a pair of conveyor belts 308 and 310 (FIG. 10) which generally move in horizontal planes. Each pair of the tram conveyor belts include an upper conveyor belt 308 and a lower conveyor belt 310. The upper and lower conveyor belts 308 and 310 in each tram are aligned in vertical registration with each other. Each of the trams also has a set of pulleys 318–321 comprising horizontally positioned pulleys, to drive and rotate the conveyor belts 308 and 310 in a horizontal direction. Each tram further has a shuttle 322 which is attached to the upper and lower conveyor belts 308 and 310. The shuttle 322 has upper and lower brackets 312 and 314 which are attached to the upper and lower conveyor belts. The lower bracket of the shuttle has a guide rail 316 which securely engages and is received by the laterally extending horizontal slot 202 of the slotted upper carrier portion 206 of the trays 204 of the test pack 200. The brackets of the shuttle have connecting portions which securely engage the lower carrier portions 246 of the trays. The tram shuttle and tram conveyor belts cooperate with each other to provide a test pack-carrying tram to convey and carry the test packs in an upright vertical position.

As shown in FIG. 10, the load tram 300 has: an upper load tram assembly 324, a load tram support 326, a load tram motor gearbox and encoder 328, a load spring 330, a lower load tram assembly 332, a thermal door assembly 334, a drive shaft 336 and a rotary cylinder 338. The twin drive belts 308 and 310 of the upper and lower load tram assemblies 324 and 326 are driven by a single motor gearbox 328. An encoder on the gearbox motor assists in obtaining accurate placement of the test pack on the carousel. The drive belts 308 and 310 can be steel/kevlar reinforced to avoid belt stretch and reduce backlash. Tensioner plates 340 and 341 (FIGS. 10, 12 and 13) at each end of the upper and lower tram assemblies can be provided to adjust tile tension of the drive belts 308 and 310. Couplings 344 (FIG. 11) are provided to allow easy drive connection between the shaft 336 of the upper and lower load tram assemblies. A lower drive clamp 348 (FIG. 11) is provided to attach the motor gearbox and encoder to the drive system. Air driven thermal door assemblies 334 (FIG. 10) provide a thermal seal for the load tram. An end of limit opto device 346 (FIG. 13) on tile lower rail assembly is provided for set up calibration on start up of the diagnostics instrument.

In operation, the test pack is loaded base first into the shuttle 322 via the load spring 330 (FIG. 10) of the lower load tram assembly 332 and the top section of the test pack is placed in the upper load tram assembly. The loadspring acts as holding force in the load area. The bar code readers 304 and 306 read and identify the test pack before proceeding to the incubation chamber in the carousel. The thermal door assembly 334 is opened via the rotary air cylinder 338 before transportation to the carousel. The test packs are moved by the shuttle via the drive belts 308 and 310 of the load tram. The drive shaft belts 308 and 310 are driven by a motor gearbox and encoder 328 to its specified position on the carousel. Once the carousel has rotated to a vacant slot, the motor gearbox and encoder 328 run in reverse, returning to the load position ready to receive the next test pack.

Figures 14, 15, 16, 17:
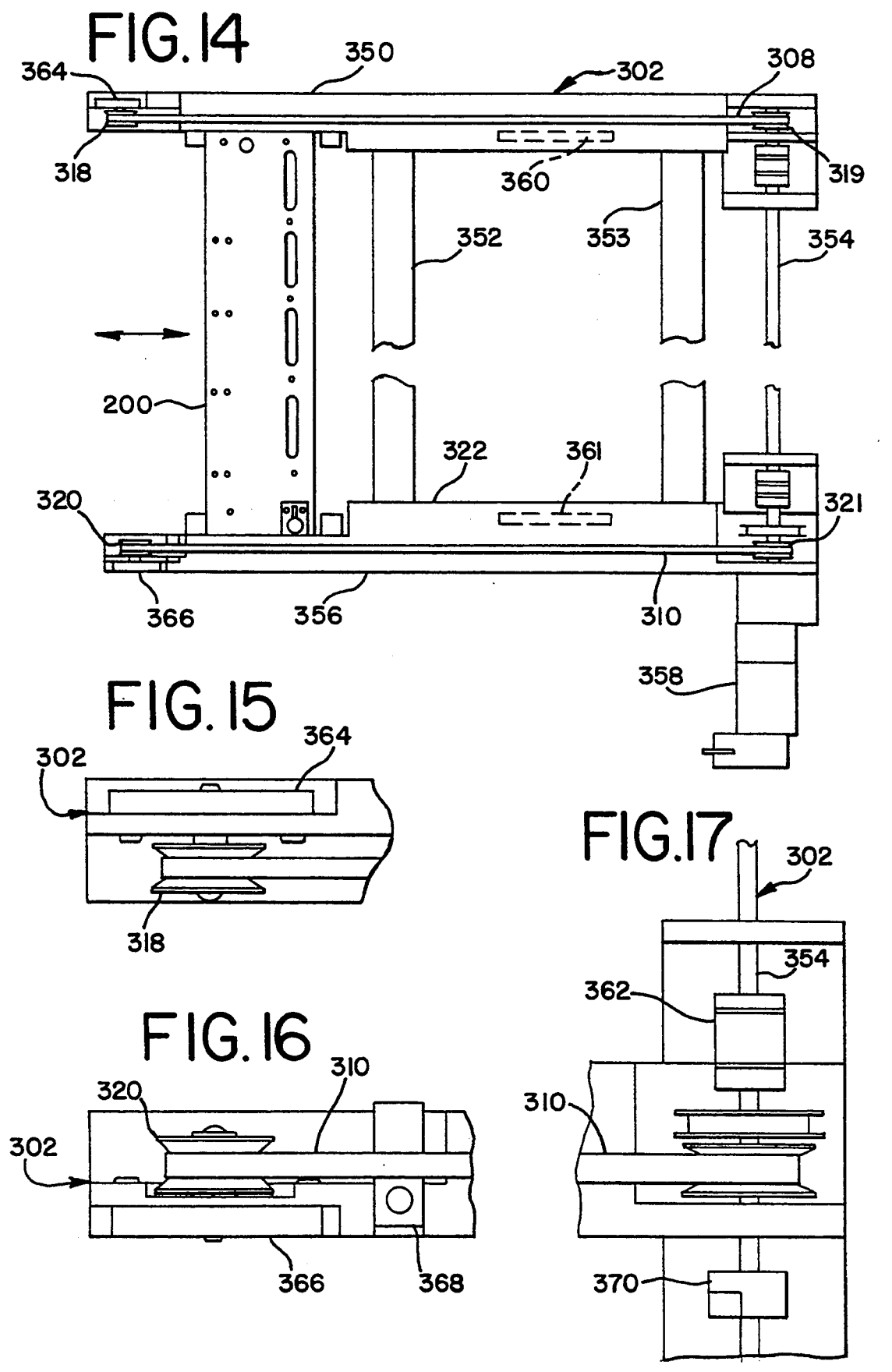

As shown in FIG. 14, the processing (processor) tram 302 has: an upper processor tram assembly 350, tie bars 352 and 353, a processing tram drive shaft 354, a lower processor tram assembly 356, a processing tram motor gearbox and encoder 358, and test pack location springs 360 and 361. The twin drive belts 308 and 310 of the upper and lower processing tram assemblies are driven by a single motor gearbox 358. An encoder on the motor 358 helps obtain accurate positioning of the test packs. Couplings 362 (FIG. 17) are provided to allow easier drive connection between the shaft 354 of the upper and lower assemblies. The drive belts 308 and 310 of the processing tram can be steel/kevlar reinforced to avoid belt stretch and reduce backlash. Processing tram tensioner plates 364 and 366 (FIGS. 14-16) at each end of the upper and lower processing tram assemblies can be provided to adjust the tension on the drive belts 308 and 310. An end-of-limit opto device 368 (FIG. 16) on the lower rail processing tram assembly is provided for set-up calibration on start up of the diagnostics instrument. A lower drive clamp 370 (FIG. 17) is provided to attach the motor gearbox encoder 358 to the drive system of the processor tram.

In operation, test packs are conveyed from the processor load tram assembly to the carousel and vice versa by the processing tram 302. The test pack 200 is located on the shuttle 322 of the upper and lower assemblies of the processing tram. The test pack is conveyed and driven via timing belts 308 and 310 attached to the processing tram shuttle to a position inside the processor so the test packs can be processed. The test packs are clamped and held firmly in the upper and lower processing tram assemblies by flat springs 360 and 361 until the processor clamp plate can be engaged and processing started. Once the test pack is processed in the processing station, the processing tram pushes the test pack in a reverse direction back onto the carousel for incubation, rotation and optical reading via the shuttle and conveyor belts of the processing tram.

Bar Code Reader

Figure 8:
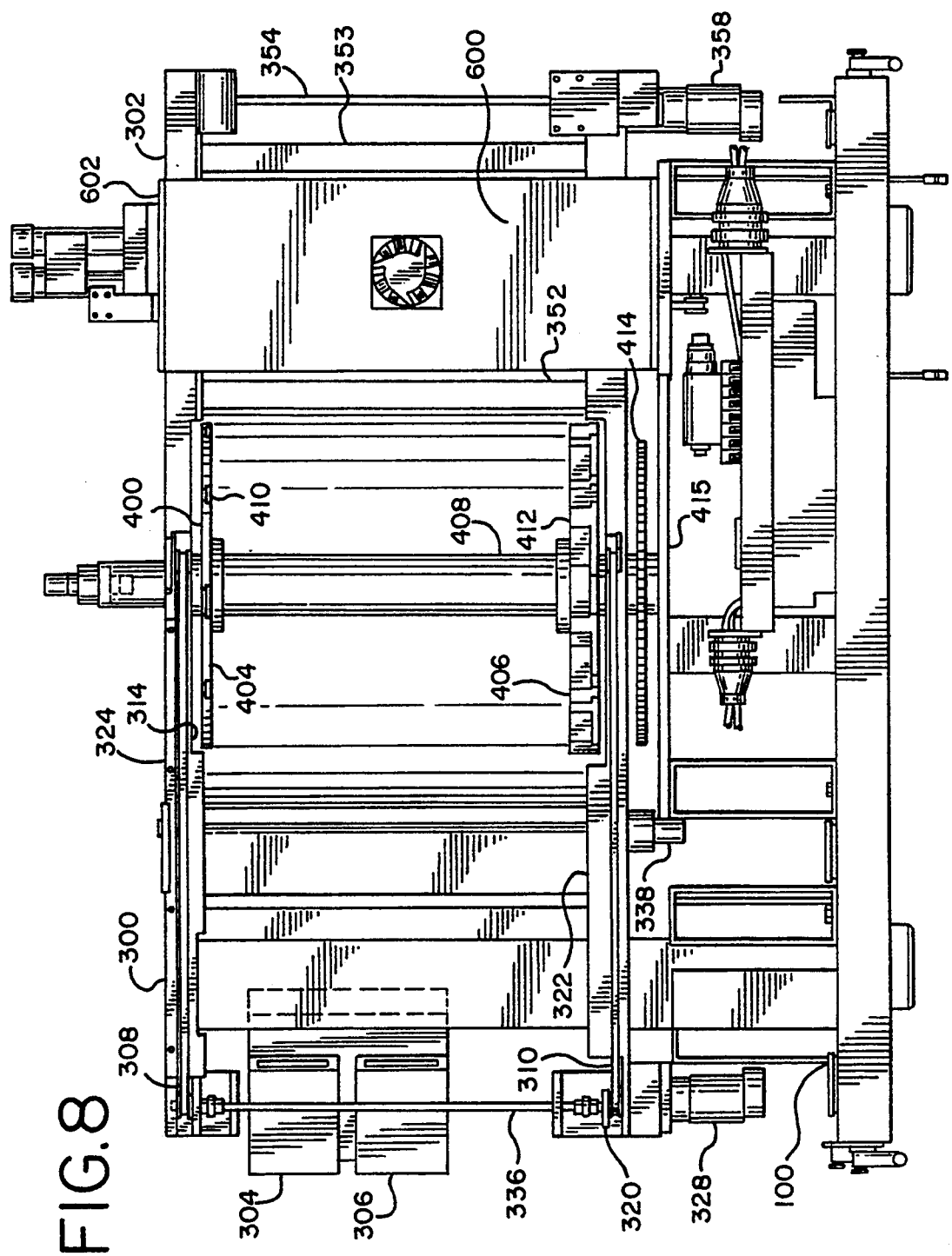
FIG. 8 is a front interior view of the automated diagnostics instrument.

When the operator closes the load door, the bar code readers 304 and 306 (FIG. 10) automatically scan both bar code stickers 206 and 208 (FIG. 24) on the side of the test pack. The bar code readers 304 and 306 (FIGS. 8 and 10) are mounted adjacent the load tram 300 to read patient identification bar codes and test pack identification bar codes on the test packs. The system uses the scanned sample ID (identification) number to track the sample. Other scanned information allows the system to record manufacturing details, such as the lot number. The bar code readers 304 and 306 are stationary units mounted inside the load chamber. The bar code readers' red lights are visible when the load door is open as shown in FIG. 2.

The bar code readers 304 and 306 (FIG. 10) are positioned adjacent the loading station and the upright support frame super structure of the load tram 300. The bar code readers scan and read the bar codes on the labels on the test packs to identity the samples and tests being conducted by the diagnostics instrument.

Carousel

Figure 28:
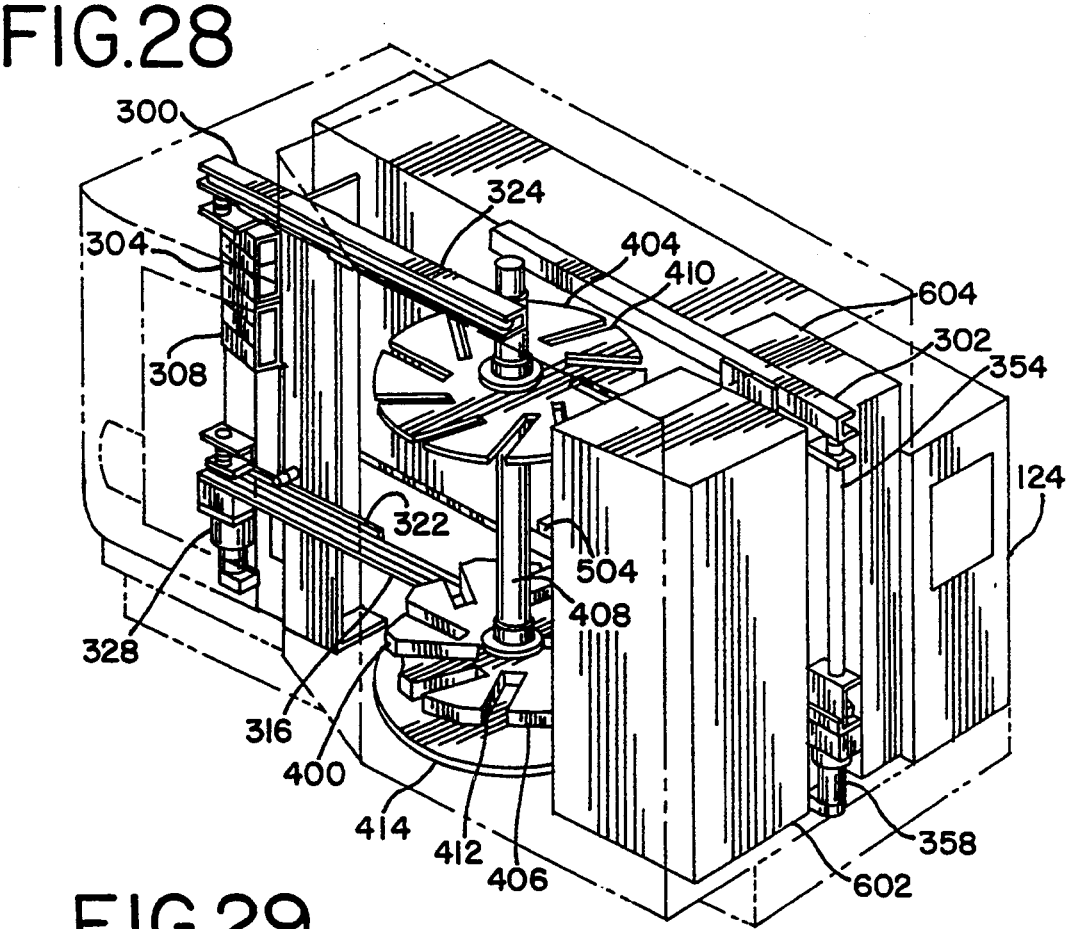
FIG. 28 is a diagrammatic perspective view of the interior of the automated diagnostics instrument.

The carousel 400 (FIG. 8, 9 and 28), also referred to as the carousel assembly, is the central holding location for test packs. The following activities occur in the carousel: initial warm-up before the test pack's first session in the processing station; incubation between sessions in the processing station; and, detection of fluorescence during the final analysis stage and amplification before the test pack is ready for removal from the automated diagnostics instrument. The carousel has a set of top and bottom platters 404 and 406 that are fixed to a central shaft 408. The central shaft of the carousel rotates around a vertical axis, causing the entire carousel to rotate. The carousel has test pack receiving slots 410 and 412 which are evenly located around the carousel for holding ten test packs in a vertical upright position. The test packs are held in the slots 410 and 412 of the carousel by a ridge in each top slot, which hooks into the groove on the backplate of the test pack. The carousel rotates gently back and forth, stopping occasionally to receive test packs or deliver them to the trams. The carousel makes a full counter-clockwise rotation, such as in 40 seconds time. The carousel's back and forth stirring motion keeps test packs from remaining near the read head light for a protracted period before the fluorescence detection stage and protects test packs from temperature variations. A motor powers the carousel by rotating a small gear that, in turn, rotates the carousel's platter.

The carousel 400 (FIG. 8) must, at various times, align with (a) the load tram 300 to retrieve new test packs or return completed test packs; (b) the processing tram 302 to deliver test packs to the processing station 602 or return them to the carousel after processing is complete; and, (c) the read head 504 (FIG. 9) to check test packs for fluorescence during amplification. A locking pin 115 (FIG. 37) locks the carousel in place. When it is time for the carousel to resume rotation, the locking pin 115 retracts and the carousel motor re-engages.

Figure 37:
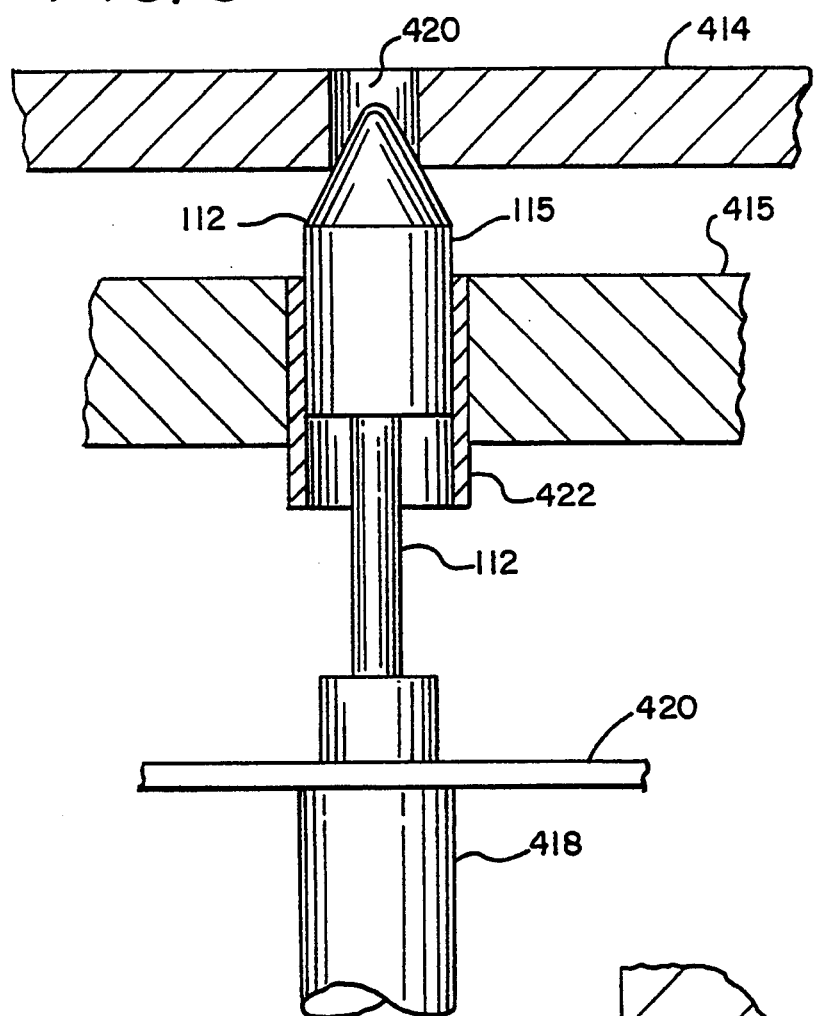
FIG. 37 is a cross-sectional view of a lower drive portion of the carousel of the automated diagnostics instrument.

The carousel assembly 400 (FIG. 28) comprises a rotating carousel with dual turntables 404 and 406. The turntables comprise a slotted upper horizontal platter 404 comprising an eccentrically slotted upper disk, and a lower horizontal platter 406 comprising an eccentrically slotted spring-loaded lower disk. The upper and lower disks define eccentric slots 410 and 412 which are aligned in vertical registration with each other to receive and engage the upper and lower carrier portions of the trays so as to hold the test packs in upright positions in the carousel. Positioned below and secured to the lower disk 406 is an enlarged driven gear 414. The driven gear is located above a horizontal base or baseplate 415 (FIG. 37). The vertical central shaft 408 (FIG. 28) extends between and connects the upper and lower disks 404 and 406. The shaft is secured by welding, bonding, or by a suitable connector such as a cotter pin to the enlarged driven gear 414. The carousel assembly has a drive motor which is connected to and rotates a cantilevered motor drive shaft. The end of the motor drive shaft has a pinon gear which meshes against, engages and drives the driven gear 414 to rotate the dual turntables (platters) of the carousel holding the test packs.

Figure 9:
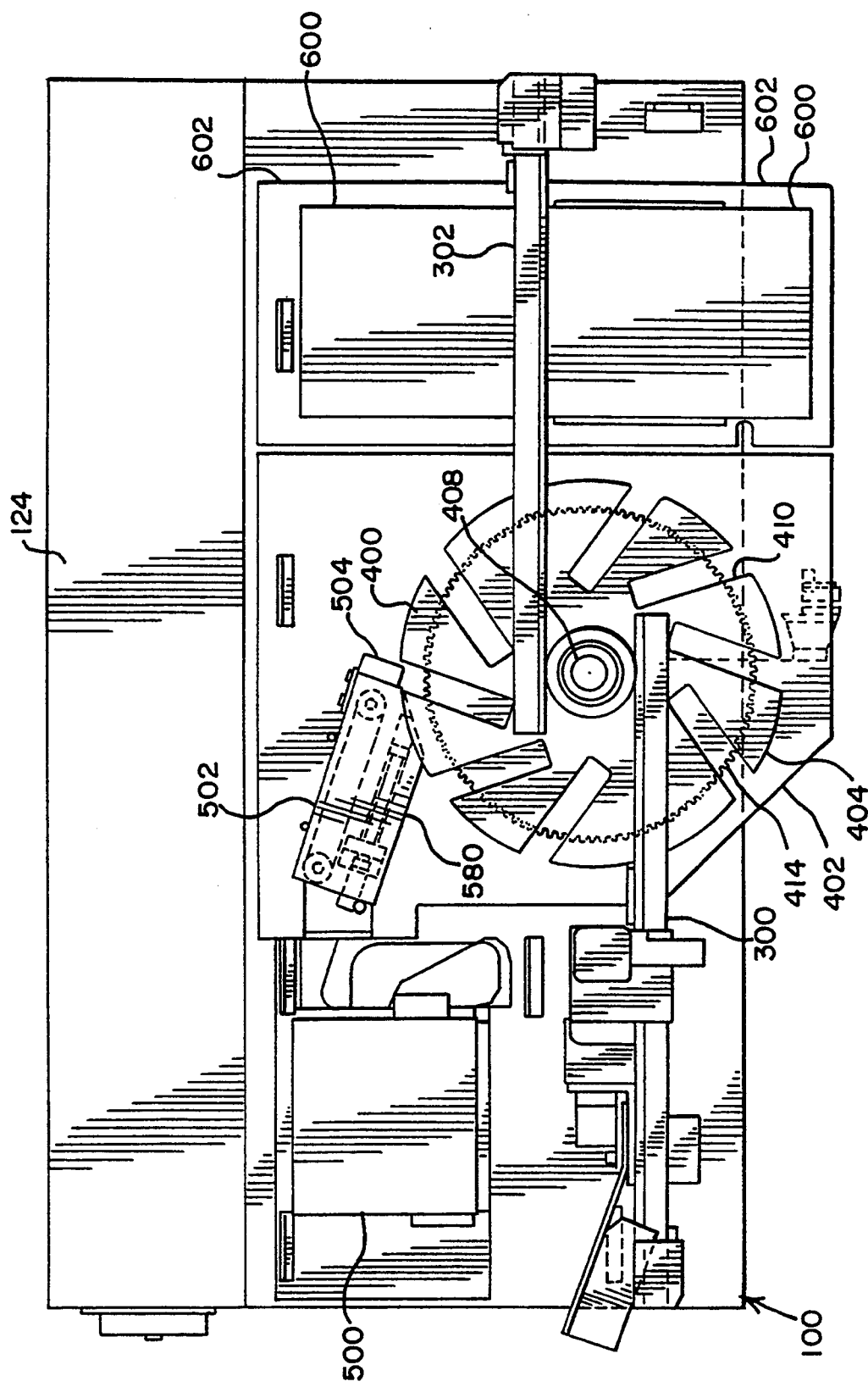
FIG. 9 is a top interior view of the automated diagnostics instrument.

The carousel assembly provides storage, incubation, rotation, transport and reading of the test packs. The test packs are loaded onto the carousel by the load and processor trams. The test packs are contained in the carousel while the required incubation temperature is achieved. The reading of the test packs is achieved in conjunction with the main body of the carousel and the read head mechanism assembly 502 (FIG. 9). In the illustrative embodiment, the carousel is configured to hold ten test packs. The angle and position of the ten slots 410 and 412 (FIG. 28) available on the carousel are such that two slots 180° apart are available in the line of travel of a test pack from one end of the diagnostics instrument to the other, i.e. left to right, and back again. The carousel slot closest to the read head 504 (FIG. 9) is positioned to ensure correct alignment of the read head and read cell window 212 (FIG. 22) of each test pack. In some circumstances, it may be desirable to use a carousel which is configured and arranged to hold more or less than ten test packs.

Figure 36:
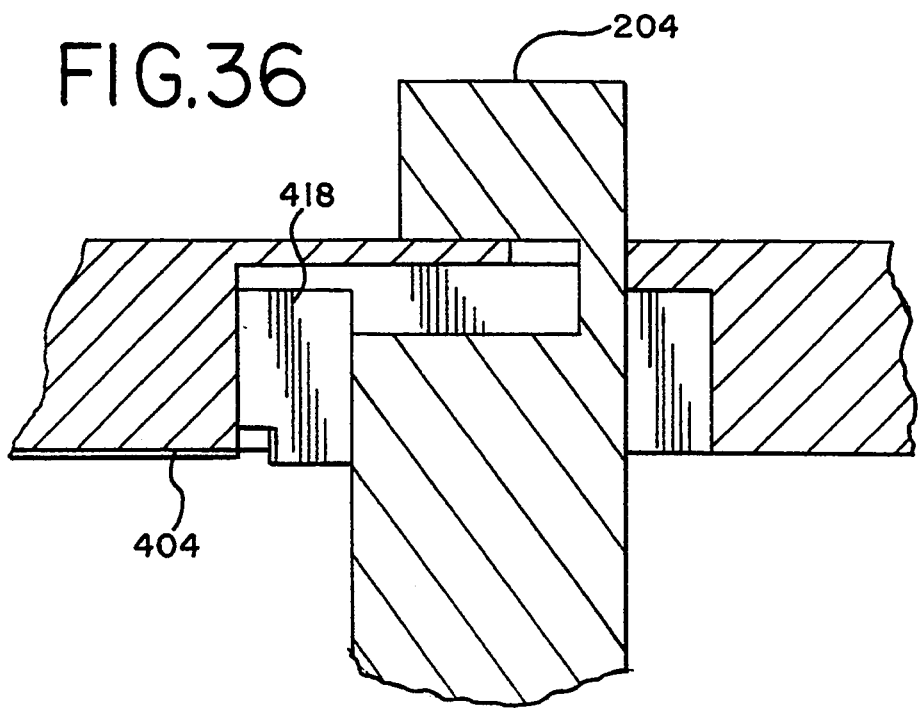
FIG. 36 is a fragmentary cross-sectional view of a lower drive portion of the carousel and locking pin of the automated diagnostics instrument.

In the preferred embodiment, each test pack is held within the aligned carousel slots 410 and 412 (FIG. 28) of the top and bottom carousel plates 404 and 406 by the use of bow springs 418 (FIG. 36) associated with and engaging the top and bottom carousel plates. The spring force of the top and bottom bow springs secures the test packs during rotation of the carousel, reading (optical scanning) of the read head (optical reader) 504 (FIG. 9) as well as hold the test packs against their own weight in the same position until removed by one of the trams 300 or 302.

The carousel is driven by a servo-controlled 12 V DC motor driven via a carousel gear 414 (FIG. 37) and pinion drive spur gear. The locking pin 115 can be made of stainless steel. The locking pin prevents rotation of the carousel during loading and unloading of the test packs by the load and processor trams, as well as during the read cycles of the read head mechanism. The locking pin is reciprocally driven by a double-acting pneumatic cylinder 418 mounted to a bracket 420. Read switches can control and monitor the status of the locking pin. The locking pin itself has a tapered end that is designed to locate into a slot 420 in the carousel gear 414 rather than passing through it, which helps ensure accurate positive engagement. The locking pin can slide within a bearing 422.

Optical Reader

Figure 38:
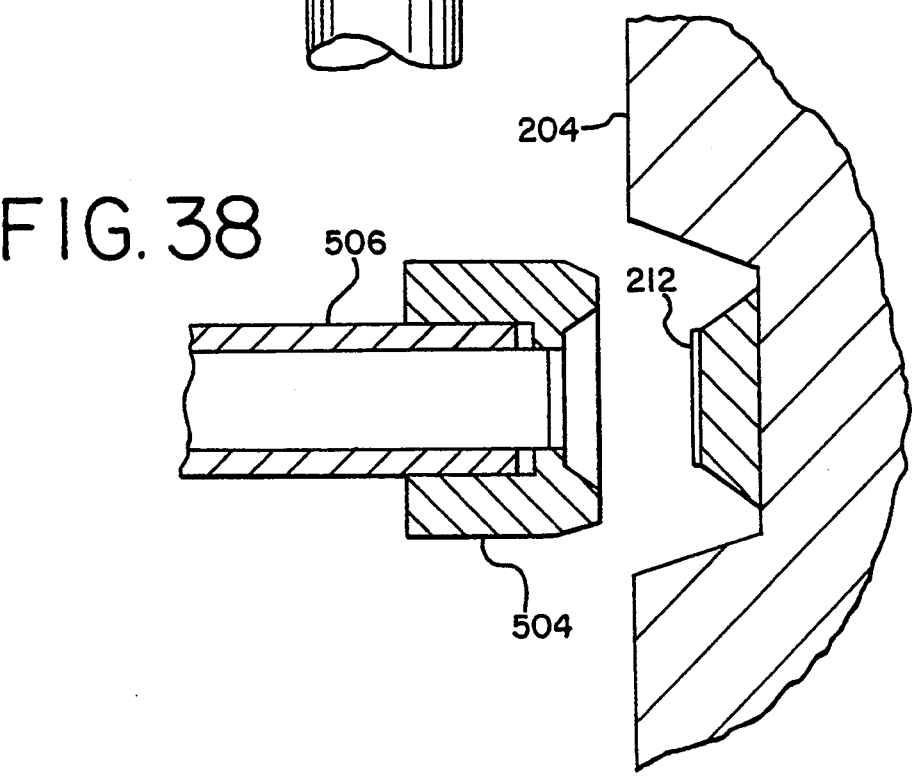
FIG. 38 is a cross-sectional view of the read head and read cell window of the test pack.
Figure 39:
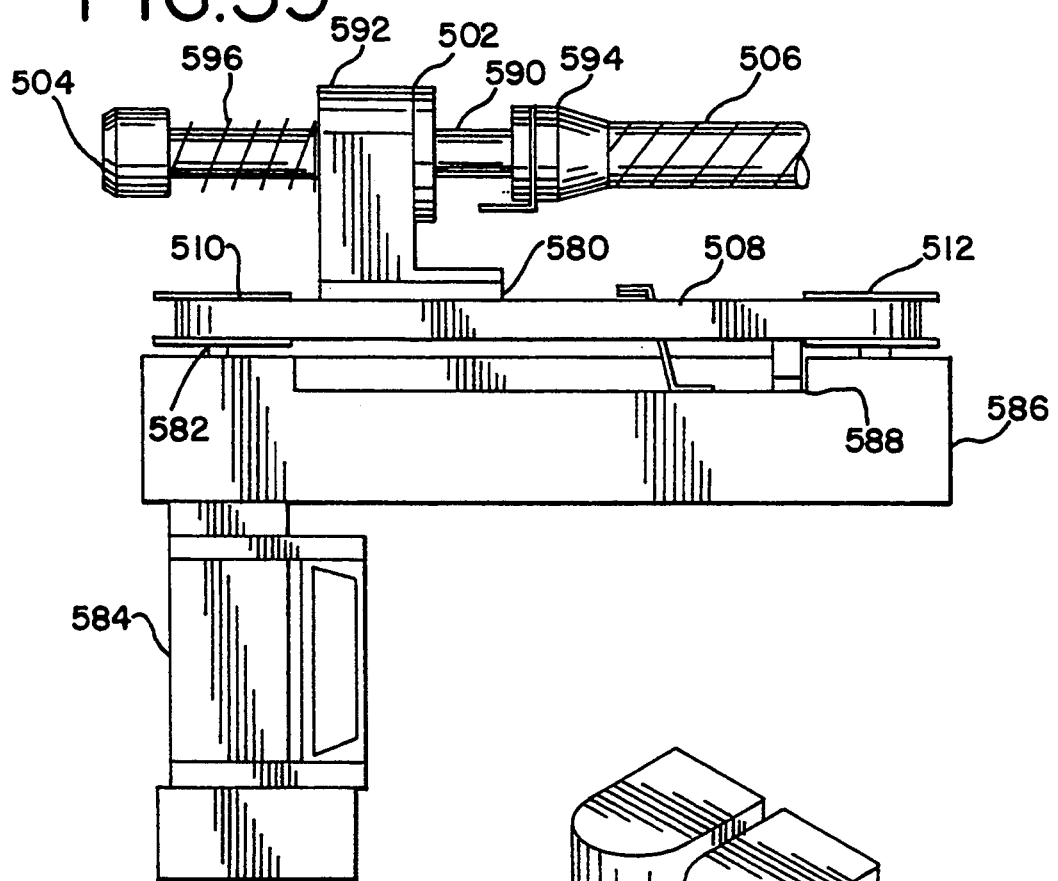
FIG. 39 is a front view of the read head and optical reader mounted upon portions of the automated diagnostics instrument.

The diagnostics instrument 100 has an optical reader and scanner 502 (FIG. 9) which provides an optical detector. The optical reader has a movable optical lead head 504 positioned in proximity to the base of the carousel to matingly engage and contact the read cell windows 212 (FIG. 22) of the test packs in order to read and sense the optically detectable analytes in the read cell of the test packs. Preferably, the read head 504 (FIG. 30) comprises a fluorescence detector to detect fluorescenced analytes. The read head 504 (FIG. 30) measures fluorescence in the samples developed during amplification to detect an analyte in the following manner carousel 400 stops and the read head 504 extends to the read cell window 212 (FIG. 38) on the rear of the test pack. The read head 504 conducts light from a halogen lamp into the read cell window 212 and scans for returning fluorescence in the sample from the amplification reaction. A fiber optic bundle 506 conducts light from the halogen lamp to the read cell and conducts fluorescence back from the read head 504 to a fluorescence detector that measures the intensity of the light being returned. Reading can take less than a second, after which time the read head 504 retracts and the carousel resumes its rotation. Multiple readings are taken to verify results. To ensure accurate detection of fluorescence from the sample, the read cell 212 on the test pack is constructed to provide a precise path length for reading. The read head and fluorescence detector can also be optimized to detect fluorescence from propidium iodide "PI"), which is the fluorescence-creating dye that can be added to the sample during amplification. Fluorescence is only detected when the target nucleic acid structure is present in the sample. The halogen lamp is always lit when the automated diagnostics instrument is on. The read head 504 is moved by a toothed drive belt 508 (FIG. 39) conducted along a set of motor-driven pulleys 510 and 512. When a test pack is not being read, the read head remains in its retracted position.

The optical reader 502 (FIG. 39) comprises a read head mechanism which provides a scanner with a front-surface fluorometer where the chemically tested sample is excited at all wavelengths between 527.5 to 552.5 nanometers and the resulting fluorescence is measured over a bandwidth between 607.5 and 656.6 nanometers. These correspond to suitable portions of the absorption and emission spectra of propidium iodide (PI). PI is the preferred dye used in the testing of the samples in the test packs.

Figure 30:
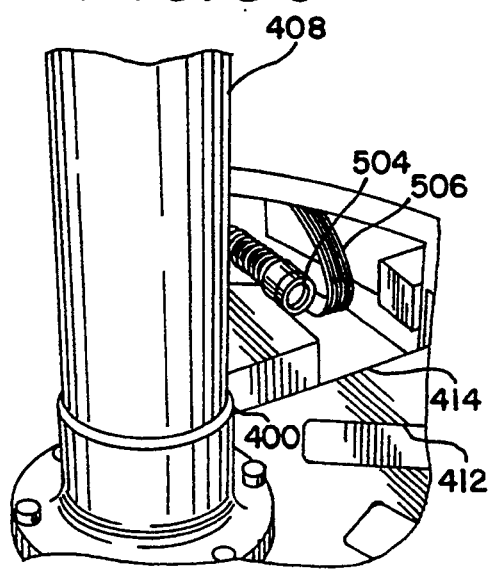
FIG. 30 is a perspective view of a read head of the optical reader of the automated diagnostics instrument.
Figure 47:
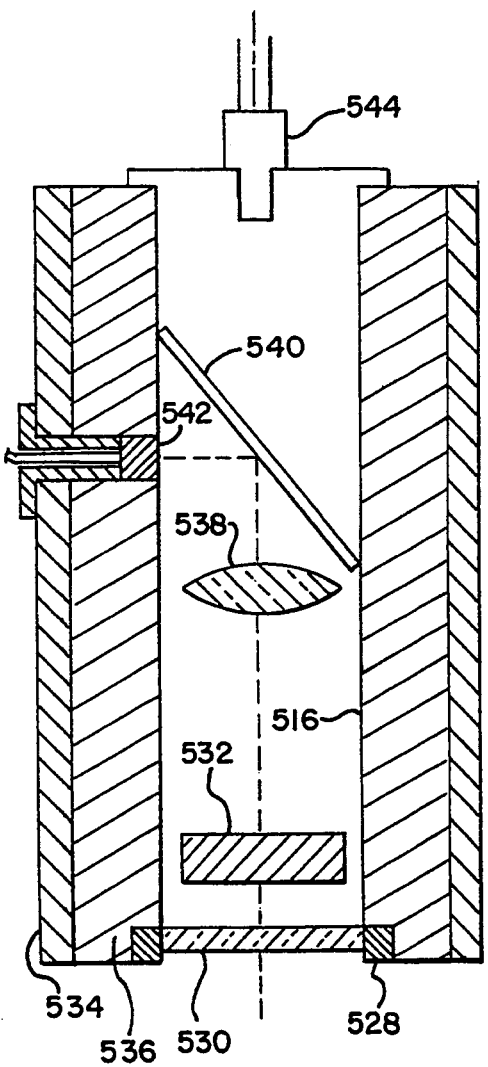
FIG. 47 is an enlarged cross-sectional view of the excitation channel components of the optical reader.
Figure 48:
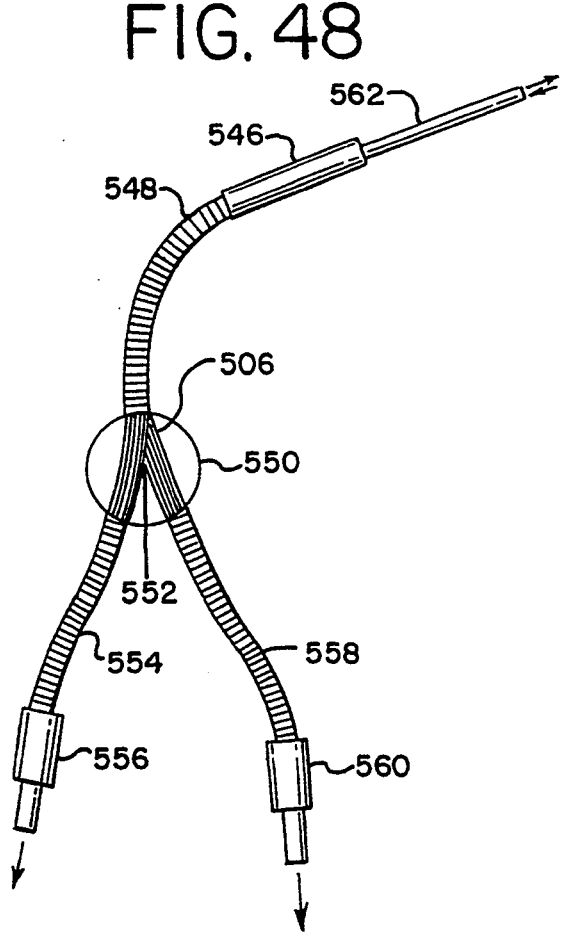
FIG. 48 is an enlarged fragmentary view of the fiber optics bundle of the optical reader with portions of a sheath removed at a Y-junction for ease of understanding and clarity.
Figure 49:
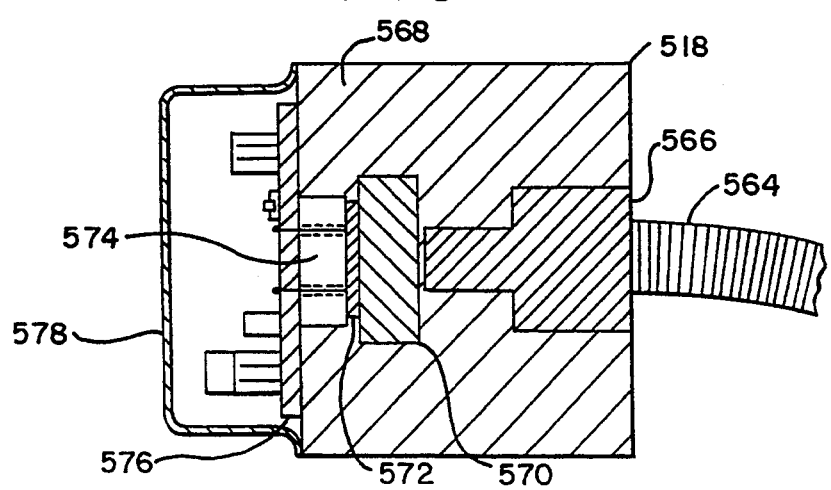
FIG. 49 is a cross-sectional view of the emission signal channel of the optical reader.

The optics system and module 500 (FIG. 9) can be divided into 5 sub-sections: (1) the light source and lamp housing 514 (FIG. 45); (2) the excitation (source) channel 516 (FIG. 47); (3) the fibre optic bundle 506 (FIGS. 30 and 48); (4) the sample well comprising the read cell window 212 (FIG. 38) and sample; and, (5) the emission (signal) channel 518 (FIG. 49). The light source of the optical reader requires sufficient light energy over the excitation bandwidth, i.e., the absorption spectrum of PI. In the preferred optical reader, a 12 V/20 W continuous wavelength (CW), open incandescent tungsten-halogen lamp 520 (FIG. 45) is used. This lamp has a ±5° beam divergence angle and a minimum 35 mm beam diameter. The lamp housing 514 has an infrared (IR) absorbing glass window 522 bound by an aluminum ring 524 which attenuates the thermal energy transfer to the rest of the optics module. The lamp housing also has numerous vents 526 and 528. The lamp of the optical reader is loaded into the lamp housing from the back and is replaceable. The lamp housing provides sufficient self-ventilation for the optical reader lamp, but shields the optical reader lamp from all direct air currents and its optical axis is aligned with that of the rest of the module.

The excitation channel 516 (FIGS. 46 and 47) of the optical reader has: an aluminum infrared (IR) absorbing window mounting 528 and window 530; an excitation filter 532; an aluminum excitation block 534; acetal excitation channels 536; lens 538; a beam splitter 540; lamp detector 542; and a receiving face 544. The thermally attenuated light from the light source of the optical reader is passed through the IR-absorbing glass window for attenuation. The purpose of this is to protect the optical components from excess temperatures. The absorbed energy is carried away by the bulk of the aluminum excitation channel housing. A large thermal gradient, insulation, can be provided by making the excitation channel out of black acetal. The acetal excitation channel 536 has a cylindrical section which, when loaded with the excitation channel optical components, is placed into the housing and is secured. The near-parallel source beam of the optical reader can be filtered by a 25 mm diameter bandpass interference filter with a 540 mm center wavelength (CWL) and 23 nm full width half maximum (FWHM). Blocking by such a filter extends from x-ray up to IR at 120 nm and the filter has a minimum optical density (OD) of 6, typically 8 and a minimum transmittance of 60%. The effective CWL of the filter at a 5° incidence angle is about 539.25 nm which is negligible. A bi-convex object lens 538 of the optical reader collects the excitation energy light and can diverge it onto a 3 mm diameter fibre optic bundle face 544 at a 60° solid angle which is less than the 70° acceptance angle of the optical fibers. The fibre optic face 544 is placed within the lens focal length such that its face is maximally illuminated. The optical fibers are finely randomized in order to effectively diffuse the source image. A glass beamsplitter 540 can be placed at a 45° angle to the diverging excitation beam. This reflects about 5% of the excitation energy towards a silicon photodiode to help monitor the lamp of the optical reader.

As best shown in FIG. 48, the fibre optic bundle 506 of the optical reader has a Y-guide configuration with: a common fiber bundle ferrule 546, common bundle metallic sheath 548, a Y-shaped junction 550, split 552, an emission signal bundle metallic sheath 554 and ferrule 556, and an excitation lamp bundle metallic sheath 558 and ferrule 560. A common bundle 562 comprising some 8000 glass fibers is secured in a long stainless steel ferrule 546 which then accesses the sample window. This carries both excitation and emission beams. The main fiber optics bundle 562 is then bifurcated at a suitable junction 550 with 64% of the fibers being dedicated to the emission (signal) channel. The fibers are randomized either at the common ferrule 546 or at the junction 506, depending on the overall length of the guide and are protected by a metallized sheath 548. The fiber optic bundles are cemented at all the faces within their respective ferrules with finely ground and polished surfaces. The cement, however, is selected so that it is transparent to the excitation and emission wavelengths of the light. This is helpful to ensure negligible background emissions due to self-fluorescence of the guide.

The shape and size of the sample well comprising the read cell window 212 (FIG. 38) of the docking mechanism for the optical reader is designed to restrict emissions to a 30° solid angle, so as to be within the acceptance angle of the fibre optics (70°) for maximized efficiency of signal collection. The read cell window 212 has an outwardly extending frustoconical (frustum-shaped) cross-sectional configuration. The read head 504 has an inwardly extending frustoconical (frustum-shaped) configuration which provides a frustoconical socket. The read head is complementary in shape to the read cell window to matingly engage and nest within the read cell window in order to read the optically detectable analyte in the read cell. Preferably, the distance between the fibre optic face and the sample well is set up so as to minimize sensitivity to sample well movement of the test pack, maximize emission beam collection and to minimize the collection of any system background, e.g. cement fluorescence, which is reflected off the well surface of the test pack back into the fibre optics at angles up to 70°.

The emission signal channel 518 (FIG. 49) has: an excitation signal fiber bundle 564 and ferrule 566, an aluminum block 568; an excitation filter 570; a signal detector 572; an aluminum photodiode spacer 574; a circuit board 576; and aluminum shielding cap 578. The fluorescence of the tested sample in the test pack together with some reflected excitation energy are carried back through the fibre optics to the signal detector 572 and the excitation channel 516. Preferably, of the emission signal, at least 64% arrives at the signal detector. The emissions can be further filtered such as with a 25 mm diameter bandpass interference filter 570 with a 632 nm center wavelength (CWL) and 49 nm full width half maximum (FWHM). Such blocking and filtering extends from X-ray up to IR at 1200 nm. The filter 570 has a minimum optical density (OD) of 6 (typically 8) and a minimum transmittance of 70%. The effective CWL of the filter 570 at the 35° incidence angle for background emissions can be 592.59 nm and 624.18 nm at a 15° incidence angle for the signal. The background emission can extend to 14.91 nm outside the intended emission signal lower cutoff wavelength (607.5 nm). To further attenuate the unwanted emissions below 607.5 nm, a colored glass filter can be placed before the emission filter. The filtered signal is detected by a large-area (100 mm$^2$) silicon photodiode. The high-gain, single-stage preamplifier for this transducer preferably has low output noise (less than 1 mV), high common mode rejection ratio (90 dB) and high signal-to-noise ratio (83 dB for full scale output). The closed-loop frequency response of the amplifier is preferably matched to the characteristics of the photodiode to minimize noise gain and to indict stability. The circuit board 576 carries the photodiode. An anodized aluminum spacer 574 which guards the short photodiode electrodes by connecting the spacer to the circuit reference rail. For added improvement in noise performance and stability, the circuit is preferably electromagnetically shielded by an earthed (grounded) metal cap 578 and the block 568 containing the emission filters 570 and the detector 572 is thermally regulated at a suitable temperature.

The optical scanner 502 (FIG. 39) has a read head mechanism 580 which presents the optics module fibre optic bundle 506 to the read cell of each test pack in the correct orientation within the time selected by the system process of the diagnostics instrument. The read head mechanism maneuvers and positions the test pack so that the desired repeatable relationship is obtained between the test pack and the fibre optic bundle 506. The read head drive 582 is provided by a servo-controlled 12 V DC motor 584 and drive pulley 510 and 512 and endless drive belt 508. The drive belt 508 is attached to the elongated base 586 of the read head mechanism. The base 586 is mounted on a linear guide 588 to ensure smooth and accurate linear movement. A splined linear shaft 590 is mounted to the read head housing body 592 and provides the mounting and clamping feature for the fibre optic bundle 506 via a collet 594 on one end. The other end of the splined shaft has a tapered head and a read head compression spring 596 mounted thereon as part of the docking mechanism to ensure the required contact engagement between the read head 504 and the read cell window of the test pack. The splined shaft 590 ensures that once assembled, the fibre optic bundle 506 will be secure and not rotate so as to prevent variations and changing of the viewing area of the test pack read cell. The read head spring 596 provides the requisite compression to help enable the test pack to be positioned and clamped temporarily at each read operation. Preferably, the read head 504 comprises a double tapered read head for internal as well as an external contact with the test pack read cell window. Coarse adjustment and docking is provided by the external taper. Fine adjustment and docking is provided by the internal taper. A flag can be attached to the moving splined shaft to cut an opto, i.e. interrupts an optical beam, at the required control point which monitors the position of the read head and provides feedback information to the computer.

Processing Station

The processing station 602 (FIGS. 8 and 9) is where the automated diagnostics instrument performs numerous mechanical operations on the test pack. The processor 600 of the processing station expresses reagents from test pack blisters into the test pack sample; mixes materials in the test packs; moves liquids into waste pouches in the test pack; and seals blisters and waste pouches in the test packs to make sure that liquids do not flow into these areas of the test pack at inappropriate times.

The processor 600 at the processing station comprises three major assemblies: a clamp plate assembly 604 (FIG. 29), a wastegate assembly 608 and a saddle assembly 610. The clamp plate assembly provides a clamp plate 632 which clamps against the test pack to hold it firmly in place during processing. The wastegate assembly 608 opens and closes the waste pouches in the test pack. The saddle assembly 610 performs processing activities, such as expressing reagents and mixing liquids in the test pack. The test pack is held between the clamp plate assembly and the saddle assembly. The front of the test pack faces the saddle assembly, and the back of the test pack is against the clamp plate assembly. The processor can also have a fan 634 and a chain or wire guide 636.

Testing of the samples of the test packs are sequentially and automatically conducted by the processor 602 (processing assembly) located at a processing station. The processing station and assembly automatically express and mix reagents with the samples in the test packs in a sequence appropriate for the desired test to be conducted on the samples in the test packs. The processing station and assembly has a clamp plate assembly 604 which compressively clamps, supports and holds the test packs in an upright vertical position. Pneumatically operated magnets 606 are operatively connected to the clamp plate assembly 604 by reciprocating shafts to engage the trays and magnetically attract metallic beads in the test packs which carry the optically detectable analytes. The clamp plate assembly moves along a linear track 638. The processing station and assembly also have an upright wastegate assembly 608 which opens and closes waste pouches in the disposable closed packs. An upright vertical belt conveyor assembly is operatively connected and attached by fasteners or connectors to the vertically movable saddle assembly 610 to move the saddle assembly vertically so that the rollers, shoes, sealers and other components of the saddle assembly can contact and engage different areas of the disposable closed packs.

Clamp Plate and Magnet Assemblies

Figure 26:
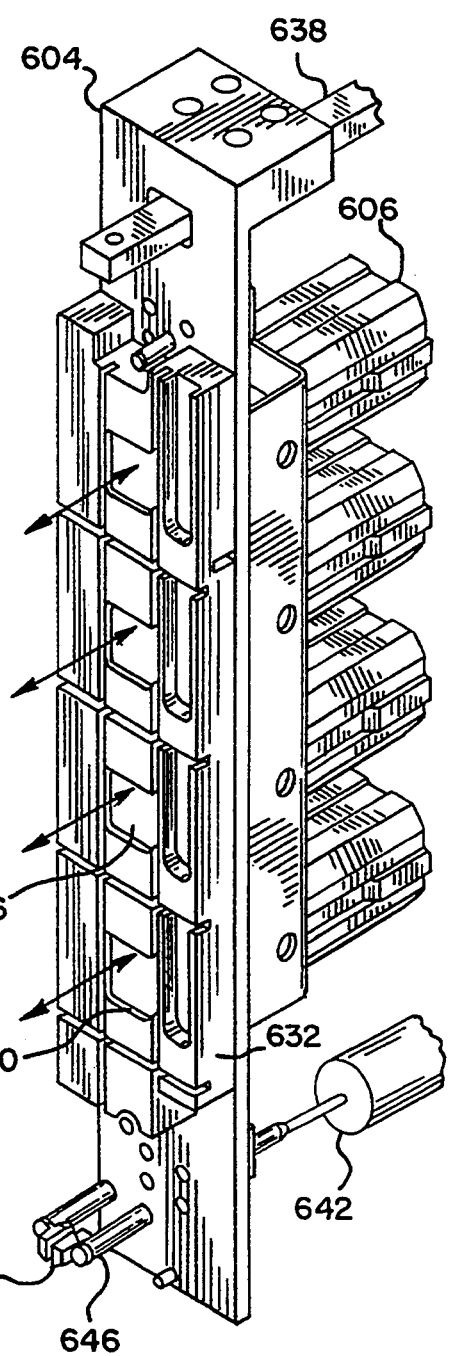
FIG. 26 is a perspective view of the clamping plate assembly and indicating the direction of movement of the magnets.

The clamp plate assembly 604 (FIGS. 25 and 26) has a clamp plate 632 which provides the supporting mechanism of the processing station. The clamp plate holds the test pack while it is in the processing station. The clamp plate surface conforms exactly to the back of the test pack so that all parts of the test pack are fully supported when the saddle applies pressure to the test pack during processing. The clamp plate pushes a newly delivered test pack against the saddle. The clamp plate retracts at the end of the pack's processing station session, allowing the processing tram to return the test pack to the carousel. Four square cut-out areas 640 in the clamp plate allow magnets 606 to advance and touch four areas 214 of the back plate 204 of the test pack 200 to pull magnetic beads out of solution. Each magnet is moved by its own pneumatic device.

The primary function of the clamp (clamping) plate assembly is to support and clamp the test pack in the correct position while it is being processed by the processor assembly. The clamp plate assembly also provides the reaction force necessary to maintain equilibrium during chemistry processing of the test pack. The clamp plate moves along a linear track 638 (FIG. 26I, and is powered by pneumatics at the top and bottom of the clamp plate. The linear guide takes the weight off the whole clamp plate assembly and maintains an accurate linear displacement upon actuation. The clamp plate assembly is driven by two double-acting pneumatic cylinders 642 which are actuated by read switches. The pneumatic cylinders are coupled to the clamp plate with rod end bushings and pins to ensure that the correct line of force is maintained.

Figure 34:
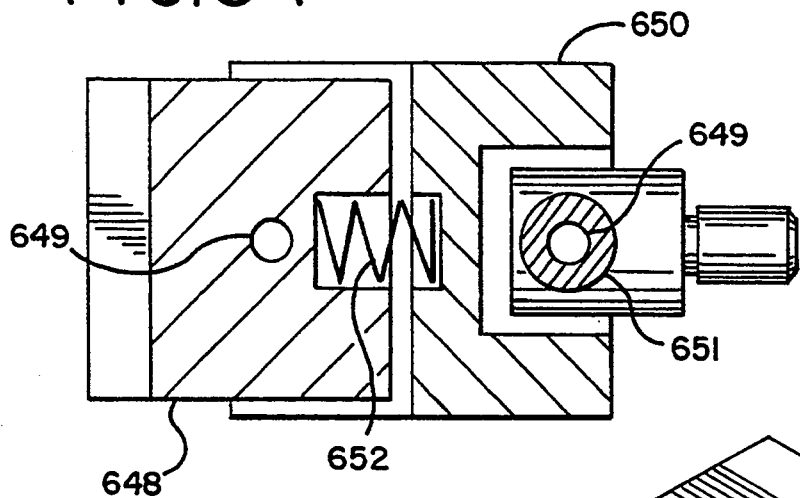
FIG. 34 is a cross-sectional view of a portion of one of the magnet assemblies of the automated diagnostics instrument.
Figure 35:
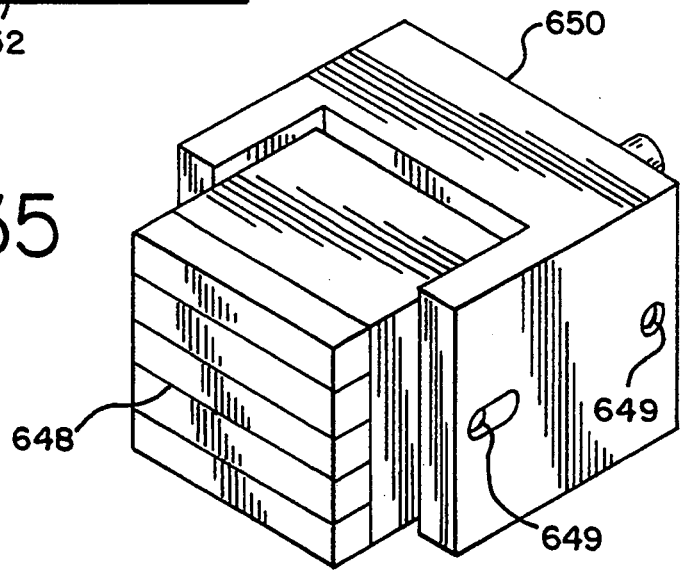
FIG. 35 is a perspective view of a magnet assembly.

As part of the chemistry process within the test packs, it is desirable for magnetic particle separation to occur in each of the four reaction areas at different times. This is accomplished by four magnet assemblies 606 (FIGS. 25 and 26) which collectively comprise a processor magnet assembly. Each of the magnet assemblies 606 has a laminated magnet block 648 (FIG. 35I, which is secured by pins 649 to a U-shaped yoke. At least one of the pins can be annular surrounded by a tube (tubing) 651 (FIG. 34). The magnets are urged outwardly from the yoke 650 by a compression magnet spring 652. The magnet is held captive in the yoke 650 via pins 649 and a spring 652. The yoke 650 acts as the magnet's carrier and guide. The spring 652 underneath the magnet gives the magnet a small amount of bias and tension. The pins 649 help control radial and axial movement of the magnet assembly to ensure a degree of self-levelling of the spring-biased magnet face against the pliable plastic backplate 204 (FIG. 25) of the test pack. The magnet is presented to the rear of the test pack backplate 204 (FIG. 25) into a specially thinned section 214 to ensure very close proximity to the pouches of the test pack containing the test reagents (chemistries) and magnetic particles. The magnet itself can comprise a boron/neodymium/iron material with a very high strength of 35 MGO. Preferably, the magnet is horizontally laminated to allow for a concentrated magnet field to be contained within a small and specific area of the test pack. The horizontal nature of the field helps prevent the magnetic particles from sliding outside of the magnetic field area on further activities within the test pack.

The magnet assembly is coupled to the double-acting pneumatic cylinder which provides the required reciprocating linear movement of the magnet so as to ensure that the magnet is engaged to the test pack when required and retracted away when not required. The pneumatic cylinder piston movement and magnet movement is actuated and controlled by reed switches mounted to the pneumatic cylinder. Coupling of the magnet assembly to the pneumatic cylinder is accomplished by a pin push fitted into the magnet yoke after passing through a piece of plastic tubing 651 (FIG. 34) within the hole of a separate connecting bar. The coupling arrangement allows a flexible degree of freedom in each axis to allow the magnet assembly to have a degree of free float to prevent clogging and sticking when being driven by the rigidly fixed double acting pneumatic cylinder through a rigidly fixed guide block.

Wastegate Assembly

Figure 32:
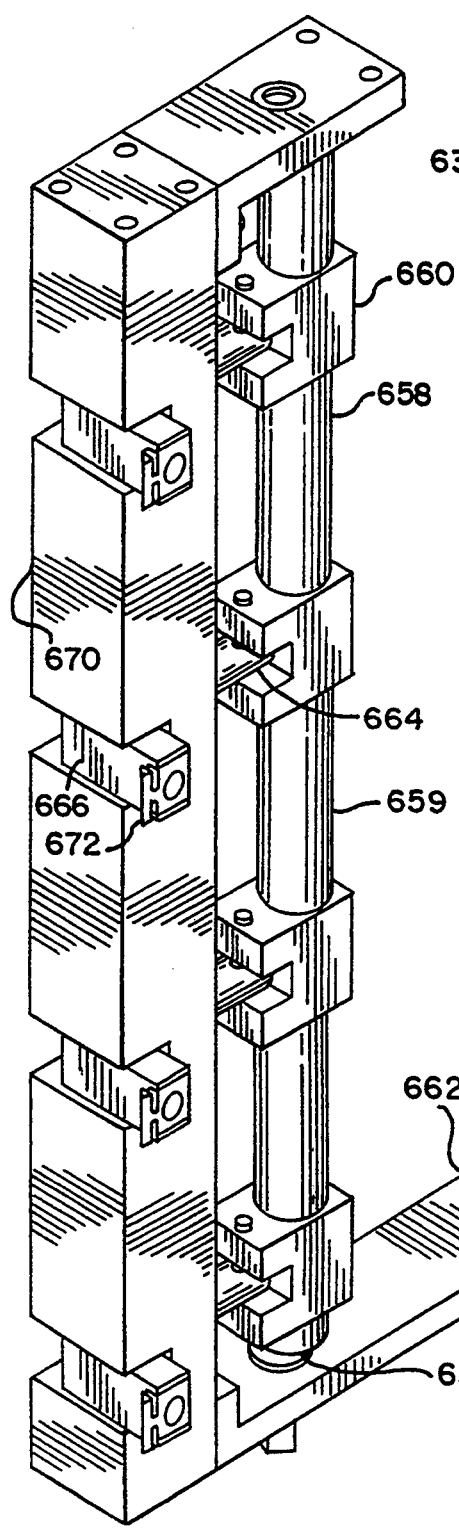
FIG. 32 is a perspective view of portion of the wastegate assembly of the automated diagnostics instrument.

The wastegate assembly 608 (FIG. 29) is the gate keeper to the waste pouches of the test packs. The wastegate assembly opens and closes the waste pouches on the test pack so that liquids are only moved to the pouches at the proper time. Four T-shaped gates 654 on the wastegate assembly line up with the four waste pouches on the test pack. A cam shaft 656 (FIG. 32) rotates the wastegate assembly, pulling the gates away from the pack to open the waste pouches, and pushing the gates against the pack to temporarily close them.

Figure 33:
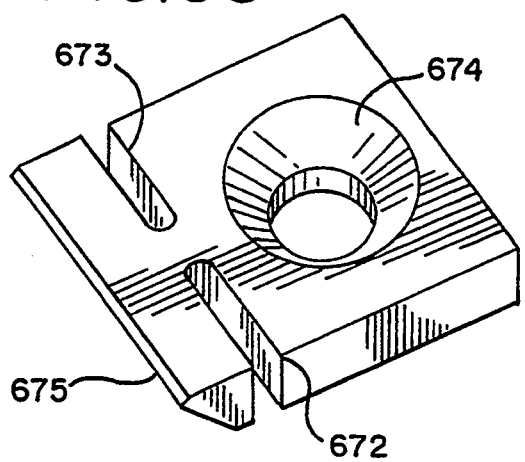
FIG. 33 is an enlarged perspective view of a sealing insert portion of the wastegate assembly.

The function of the wastegate assembly is to provide a temporary mechanical sealing gate to each of four waste areas on the test packs (TSP). This is achieved by a single vane rotary air actuator providing the drive force to an eccentric stainless steel cam 658 (FIG. 32) which in turn activates four independent gates. The cam 658 has multiple cam sections 659 which provide linear displacement of the wastegate from the given 180° rotation provided by the air actuator. Acetal cam followers 660 provide a link between the cam 658 and a travelling wastegate wall or floor 662. The wastegate wall or floor 662 is in contact with the cam 658 to provide a positive return device. Pins 664 pass through the cam followers 660 and spring-loaded wastegate feet 666. The springs in the wastegate feet provide a preload which is transmitted to the pouch surfaces of the test pack upon contact to ensure the correct sealing force and pressure is applied during sealing. Each of the individual wastegate feet are guided and positioned by a single guide block 670 containing acetal bearings to free and smooth running. Wastegate sealing inserts 672 are placed on the end of each of the wastegate feet 666 to contact and seal the waste pouches in the test packs. The wastegate inserts 672 have a self-levelling section 673 (FIG. 33), a locating fixing section 674 and a sharp edge 675 comprising a sealing member that provides the required sealing characteristics of the test pack pouch.

Saddle Assembly: Rollers, Mixers and Sealers

The saddle assembly 610 (FIG. 18) is the workhorse of the processing station. The saddle assembly manipulates the test pack—expressing reagents into the patient sample, mixing liquids and washing background material out of the sample—so that the assay can take place. The saddle assembly 610 has a splashguard 611 and contains three subassemblies that operate on the test pack: (1) roller subassemblies 612 mix liquids in the test pack reaction area and move liquids around in the disposable closed pack: (2) mixer subassemblies 618 comprising shoes manipulate test pack reagent blisters to re-mix their contents and also express blister contents into the reaction area of the test pack; and (3) sealer subassemblies 624 permanently close off empty blisters, vacated reaction areas and filled waste pouches to keep liquids from being pushed back into them. When the automated diagnostics instrument 100 manipulates a portion of the test pack, the entire saddle assembly 610 moves up or down to position the rollers 614 and 616, mixers 620 and 622, and sealers 626 and 628 over the appropriate test pack location. The saddle assembly 610 moves on a linear bearing. Subassemblies move in and out as needed to manipulate the pack. Rotating cams drive the subassemblies in and out pushing them against the test pack.

The roller subassemblies 612 (FIG. 18) of the saddle assembly mix liquids in the test pack reaction area and move liquids from the reaction area to another location in the test pack. The roller subassemblies mix liquids in a reaction area as follows. A roller 614 or 616 of the saddle assembly can be first positioned at the bottom of the reaction area of the closed disposable pack. The saddle assembly is then moved upwardly, pulling the roller until the liquid in the reaction area of the closed disposable pack is at the top of the reaction area. Then, the roller is repositioned above the liquid at the top of the reaction area of the closed disposable pack and pulled downwardly causing the roller to push the fluid into the bottom of the reaction area. This sequence is repeated many times to thoroughly mix the contents of the reaction area of the closed disposable pack.

The roller subassemblies 612 (FIG. 18) of the saddle assembly also move liquid into waste pouches of the closed disposable pack as follows. A roller 614 or 616 of the saddle assembly can be first positioned at the bottom of the reaction area. The wastegate opens the waste pouch. Then, the roller pulls up to the top of the reaction area, pushing the liquid into the waste pouch. Finally, the wastegate temporarily closes the waste pouch. After the reaction stage is completed, the waste pouch is permanently heat sealed by the sealer assembly.

The roller subassemblies 612 (FIG. 18) of the saddle assembly further move liquid down to the next reaction area via a roller 614 or 616 which can be positioned at the top of the reaction area of the closed disposable pack and then moves downwardly to the bottom of the reaction area. The pressure of the liquid in the reaction area breaks the burstable test pack seal between the reaction areas and the liquid is pushed into the lower reaction area of the test pack. Then, a permanent heat seal across a portion of the disposable pack is generated by the sealer assembly 624 to close the upper reaction area of the test pack.

The mixer (shoe) subassemblies 618 (FIG. 18) of the saddle assembly suspend the contents of test pack reagent blisters and also express the contents of test pack blisters into the test pack reaction area. The mixer (shoe) subassemblies mix blister contents before expressing them into the reaction area such as, for example, to re-suspend magnetic beads in solution. The mixers (shoes) 620 and 622 manipulate the blisters as follows. One mixer (shoe) 620 or 622 extends briefly, pressing one side of the test pack blister, and then retracts. Then the other mixer (shoe) 620 or 622 presses the other side of the blister, and retracts. This sequence is repeated, causing a back-and-forth mixing of the liquid in the blister. The mixer (shoe) subassemblies 618 also express the contents of a test pack blister into a reaction area as follows. The outer mixer (shoe) 622 presses down on the outer half of the test pack blister (the half that is furthest away from the reaction area). Then, the other mixer (shoe) 620 presses downwardly with sufficient pressure to break the blister's burstable seal, causing the blister's liquid to move into the reaction area. Then the sealer assembly 624 generates a permanent heat seal to close the test pack blister.

The sealer assemblies 624 (FIG. 18) of the saddle assembly 610 create heat seals to close off empty blisters, vacated reaction areas and filled waste pouches in the test packs to keep liquids from being pushed back into them. The side sealer 626 creates a vertical heat seal that closes emptied reagent blisters in the disposable packs. The reaction area sealer 628 creates a horizontal heat seal to close a reaction area in the closed disposable pack after its contents are moved to the next reaction area under it. The reaction area sealer 628 can also be used to permanently seal the entrance to waste pouches as follows. The heat sealer 628 is positioned adjacent to the test pack. Heat is applied to the sealer 628 for a short time. Then, the sealer 628 remains in the closed disposable pack to hold the seal closed while it cools. The sealer 628 is then retracted from the test pack before the saddle assembly moves.

As discussed above, the saddle assembly 610 (FIG. 18) of the processing station includes sub-mechanisms and assemblies comprising a roller assembly 612, a mixer assembly 618 and a sealer assembly 624. The roller assembly 612 has horizontally reciprocating cam-driven rollers 614 and 616 to mix reagents and samples in the reaction areas of the closed disposable packs. The rollers 614 and 616 also move background material and waste portions of the samples to the waste pouches in the closed disposable packs. The mixer assembly 618 has horizontally reciprocating cam-driven impact members 620 and 622. The impact members 620 and 622 preferably comprise metal shoes to manipulate and mix reagents in the blisters of the closed disposable packs. The shoes 620 and 622 are also manipulated to break the blisters in the closed disposable packs to express reagents from the blisters to the reaction areas of the closed disposable packs. The sealer assembly 624 has horizontally reciprocating cam-driven sealers 626 and 628. The sealers include a side sealer 626 and a reaction area sealer 628. The side sealer 626 heat seals emptied test pack reagent blisters. The reaction area sealer 628 heat seals used, emptied, vacated test pack reaction areas as well as partially filled or full waste pouches containing the background material and waste portions of the samples in the test packs.

The roller subassemblies 612 (FIG. 18) comprising part of the saddle assembly of the processor (processing station) employs two composite rollers 614 and 616. One roller, the high pressure roller 614, is for high force rolling. One roller, the low pressure roller 616, is for low force rolling. The rollers move fluid around the test pack when processing the test pack. The outer silicon sheath (layer) 676 (FIG. 42) of the rollers conforms to the contours of the test pack to ensure minimum residual volumes and can provide a 3 mm footprint which acts as a shut off to stop back flow from the waste reservoir of the test pack. The nylon core 677 of each roller provides the support and bearing surface for the outer silicon sheath 676 of the rollers. Additionally, the nylon core 677 provides a good interstitial bonding face for the silicon, which significantly reduces delamination of the rollers. The rollers are held by a roller pin 678 and E-clips 679 on a yoke 680 and are urged against the test packs by springs 681 and a roller cam follower 683 and then return is assisted by return spring 682. The cam follower 683 is driven by a roller cam 684 and receives a bearing pin 685 and return pin 686.

Figure 41:
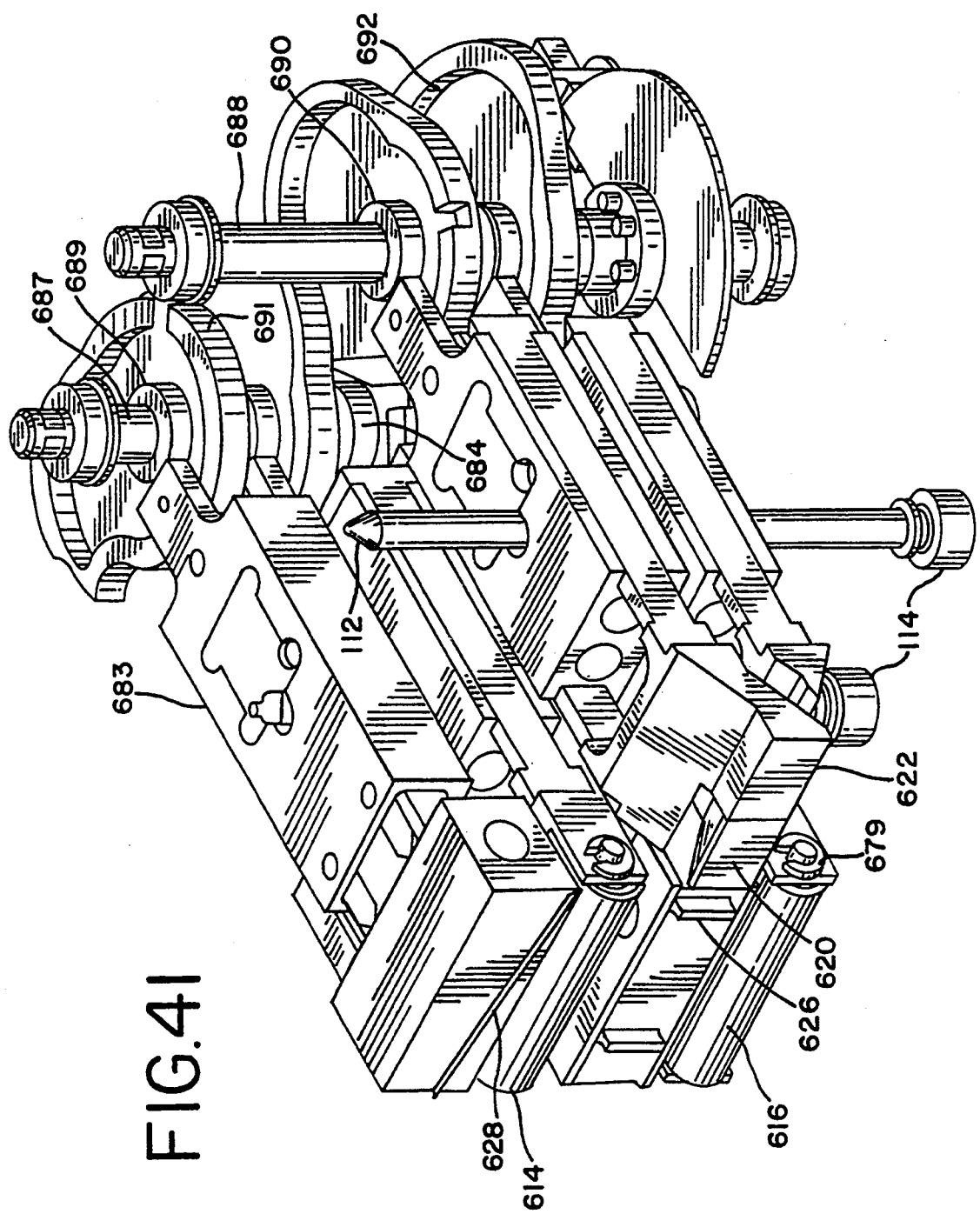
FIG. 41 is an enlarged perspective view of a saddle assembly and portions of the processor assembly of the automated diagnostics instrument.

The processor saddle 610 (FIG. 18) is a compact mechanism and assembly housed and maneuvered vertically within the processor. Its purpose is to manipulate the reagent fluids and test sample within the test pack in order to carry out a specific assay. The test pack manipulations required are: (a) blister making; (b) blister expression; (c) blister sealing after expression; (d) rolling waste fluid into waste blister; (e) reaction area fixing; (f) rolling target fluid into next reaction area; (g) sealing reaction area after use: and, (h) rolling amplification of the tested sample (cocktail) into the read cell. The saddle 610 uses six saddle actuators to accomplish this set of manipulations. The saddle actuators are driven by two servo-motors via a set of interleaved cams 684 mounted on two cam shafts. The cam shafts include a roller cam shaft 687 (FIG. 41) and an expression cam shaft 688, which have a set of position or states, e.g. dwell positions. The positions/states of the roller camshaft 687 include: (1) high pressure roller and reaction area seal [RASEAL]; (2) high pressure roller; (3) both rollers; (4) low pressure roller; (5) off; and (6) side sealers [SSEAL]. The position/states of the expression camshaft 688 include: (1) both shoes; (2) back shoe; (3) off; and, (4) front shoe. The position/states of the cam shafts are positioned at 60° intervals. The roller camshaft 687 is physically prevented from entering the interstate condition between the side sealer 626 and the high pressure reaction sealer 628 by the complimentary shapes of the sealer cams. The diagnostics instrument safely resets the saddle cams 684 by sensing the calibration opto device and resetting in the opposite direction if the opto device is blocked.

The saddle cams 684 (FIGS. 41) comprise generally similar roller cams, sealer cams 689 and mixer (shoe) cams 690. The saddle cams are dual profiled cams which have an external cam profile 691 to provide the necessary actuation force, to the cam follower, and a secondary internal cam profile 692 to provide a fall-back return mechanism. The cam profiles themselves can be composites of a basic simple harmonic motion (SHM) curve over 57.5° and a nominal 5° dwell at the nose, coupled with constant radii between equivalent states. There can be an eight millimeter rise/fall between positions/states of the cam shafts. This SHM cam profile was chosen to give the lowest possible pressure angle to minimize side loads in the system. The saddle cams act on roller bearings in the cam followers 683 which move within the guideblock. The cam followers 683 of the roller subassemblies, sealer subassemblies and mixer subassemblies are generally similar. The cam followers are spring-loaded against the saddle cams by the action of the return springs on the locking pins 114. If the locking pins 114 are unscrewed and removed, the actuators can be easily extracted. For the rollers 614 and 616 and expression shoes 620 and 622, the force is passed through mainsprings to the actuator yoke while the sealers 624 and 626 use a self-levelling mechanism. The rollers 614 and 616 themselves are nylon cores around which a silicon rubber is formed and then ground to shape. The expression shoes 620 and 622 are dog-legged in order to achieve horizontally offset shoes from a vertical camshaft. This is to enable the shoes 620 and 622 to mix fluid in a blister by alternately mixing half a blister into the other half.

Figure 40:
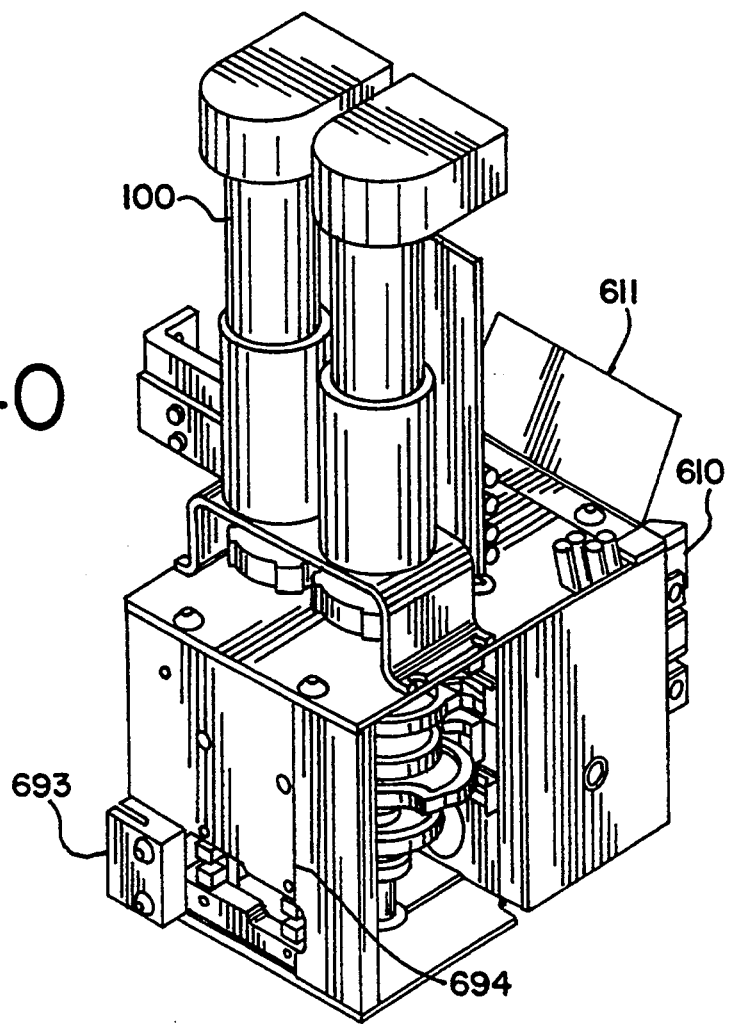
FIG. 40 is a perspective view of portions of the saddle assembly.

The prime movers of the saddle processor are servo-controlled DC motors coupled to the saddle cams with gearboxes and universal couplings. These can be splayed in order to more easily fit them into the processing area. Vertical motion of the saddle processor is provided by a servomotor on the processor frame which drives a toothed belt. The processor saddle is attached to this belt by a belt clamp 693 (FIG. 40) which relies on maintaining an equivalent cross-sectional area while changing the cross-sectional shape. This ensures that the belt is held firmly in place.

The saddle is directly attached to the processor by the saddle carriage of the vertical linear guideway. The saddle carriage is screwed into place against a vertical datum 694 (FIG. 40) on the saddle backplate. The top and bottom plates register against this same vertical datum. The top and bottom plate datum lines register in turn to the guide block which dictates the actuator positions. The guide block 695 (FIG. 18) is split into three parts which align about the actuators to provide a good reference back to the datum.

The sealers 626 and 628 (FIG. 18) rely on a hot element made of stainless steel or other material, and protected from the plastic test packs by polytetrafluoroethylene (PTFE) loaded glass weave tape. The PTFE tape prevents molten plastic of the test packs from sticking to the hot element. The illustrated diagnostics instrument uses a sealer with a shoe machined so as to provide mechanical anchoring for the hot element, the PTFE weave tape and the electrical connections. The sealers self-levelling mechanism relies on two pins 696 and 697 (FIGS. 43 and 44) which self-align themselves in two oversize slots. The sealers are urged toward the disposable packs by springs 699. When the sealers are not in contact with the test pack, the sealers maintain a square position. When one corner of the sealer is grounded, the rest of the sealer rotates about that point until it sits down fully. The short sealer is relieved so that it spans the reaction area without compressing the fluid within the reaction area of the test pack and provides a uniform pressure about the hot element.

The saddle can be electrically connected to the processor frame by a conduit chain through which cables 138 (FIG. 18), ribbon cables and extra-flexible sealer cables run. These can be led to the distribution board where the motors, encoders and opto-devices are joined. The sealers can also be connected by flexible cables through an enclosed protective conduit to the distribution board.

Pneumatic System

The pneumatics schematic flow diagram of FIG. 27 diagrammatically illustrates the pneumatic circuit 700 of the diagnostics instrument. The pneumatic circuit 700 controls and supplies air to all assemblies, components and modules of the diagnostics instrument that contain some form of pneumatic actuation. The pneumatic circuit 700 has a pneumatic vessel or tank comprising an air reservoir 702. Connected to the reservoir via a non-return valve 704 is a pump (compressor) 706 having a silencer 708. Also, serially connected to the reservoir are: a pressure regulator 710, electropneumatic pressure switches 712 and 714, pressure gauges (switches) 716 and 718 and a clump valve 720. A ten-way manifold 722 having solenoid direct-acting pneumatic valves 724–731 is pneumatically connected to pneumatic cylinders 732–740 and to the pressure regulator 710. The ten-way manifold 722 includes: a locking pin valve 724, a thermal door valve 725, a wastegate valve 726, a clamp plate valve 727, and magnet (magnetic) valves 728–731 for the beads. The locking pin valve 724 is connected to a carousel locking pin cylinder 732 via a six-way connector 742. The thermal door valve 725 is connected to a load tram thermal door cylinder 733 via a six-way connector 742. The wastegate valve 726 is connected to a wastegate cylinder 734 via a 12-way connector 744. The clamp plate valve 727 is connected to the top and bottom clamp plate cylinders 735 and 736. The magnet valves 728–731 are connected to the magnet (magnetic) cylinders 737–740.

In the pneumatic circuit, the pump 706 can run until 90 seconds after the reservoir's upstream pressure switch (pressure gauge) detects 4 bar pressure. The pump restarts when the pressure switch (pressure gauge) 716 detects that the pressure has dropped below 4 bar, sending a signal to the central processing unit. A non-return valve 704 stops any leak through the pump and provides an easier start for the pump by alleviating back pressure which can otherwise cause pumps to stall. The air reservoir 702 can then be regulated to 3.75 bar and is monitored by a second pressure switch (pressure gauge) 718 which indicates the downstream pressure. A bank (manifold) 722 of solenoid-operated direct-acting valves 724–731 are used to govern the air flow to each assembly and pneumatically operated components, making sure that they are actuated at the correct time via signals from the central processing unit. The pneumatic circuit has silencers 708 and 746–748 to reduce noise levels for exhausting air and a dump valve 720 which is turned on and off by an electrical switch.

Carousel Heating System

Figure 50:
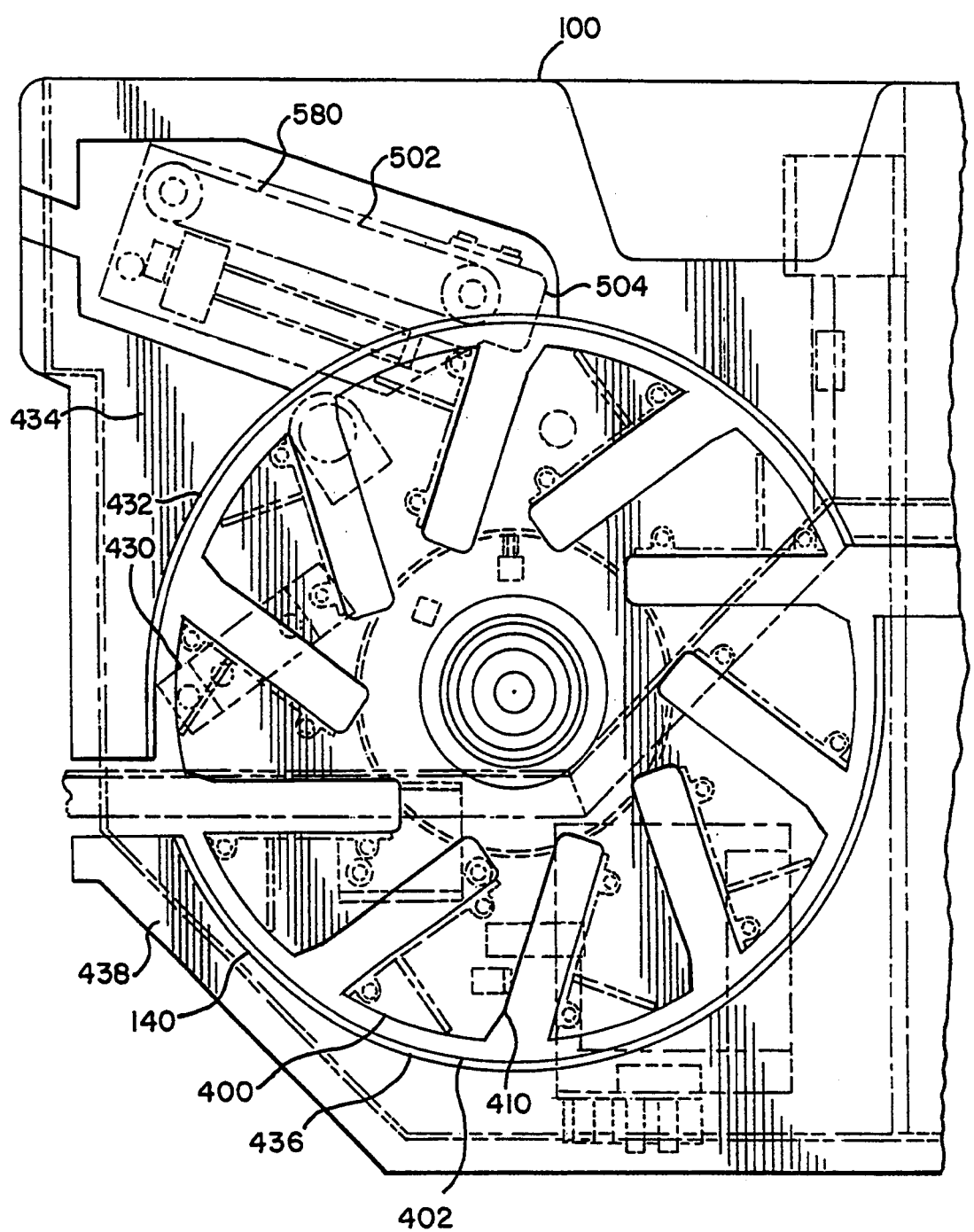
FIG. 50 is a diagrammatic top view of the carousel heating system of the automated diagnostics instrument.

A temperature control regulator assembly 140 (FIG. 50) provides a carousel heating system 402 and a processor heating system 630 (FIG. 31) to control and contain the temperature of the samples in the test packs in the diagnostics instrument 100. The temperature control regulator assembly includes an incubator heater and a processing station heater. The carousel heating system, also referred to as an incubator heater, heats the array of upright test packs in the carousel and includes heating wires and elements positioned on the lower platter (lower turntable) and on the surrounding interior arcuate carousel walls.

Temperature control of the carousel of the automated diagnostics instrument uses a buoyancy driven convection system to maintain an overall test pack temperature within 2° C. The temperature control of the carousel heating system 402 (FIG. 50) includes: a heater mat 430 attached to the upper surface of the carousel lower platter, a rear wall heater 432 adjacent rear insulation 434, and a front wall heater 436 adjacent front insulation 438. The temperature controls can be regulated by a carousel cylinder. The internal vertical walls of a carousel cylinder provide the heat source. This can be accomplished by mounting two full area heater mats to metal backing plates which are attached to the two halves of insulation forming the structural components of the system. The heater mats on the vertical walls can provide for a total power input of 120 watts and can be maintained at a set point within 37°–39° C. The air in contact with these mats is warmed by conduction. The lower plate (disk) of the carousel can have a 60 watt heater mat attached to it. The carousel heater mat provides uniform heat input to the lower plate (disk) and this combined with the low loss environment enables minimal thermal gradients throughout the plate. Convection processes distribute the heated air throughout the system. The test packs are in turn heated by conduction from the contact of the warmed surrounding air. The read cell area 212 (FIG. 22) of the test pack is particularly important and this zone is heated by direct conduction. The insulation the carousel heating system can be constructed from a low density rigid polyurethane with a density in the range of 140 Kg m$^3$ to 180 Kg m$^3$. Such low density foam provides thermal conductivities of $\sim$0.03–0.04 w/m/k which is helpful to maintain the low thermal gradients required and provide a power efficient system.

A single sensor comprising a thermistor is embedded in the carousel heater accurately report temperatures representative of each section of the carousel. The test packs are secured by bow springs within the slots of the disks (plates) between carousel segment. The bow springs provide sufficient force to maintain the lest pack is position and clamp the read cell backplate, attached to the back of the pack, against the surface of the carousel baseplate. The read cell is held in contact with the thermally conductive read cell backplate of the test pack to provide an effective conductive path from the temperature controlled carousel plate to the contents of the read cell itself, This temperature control channel can be controlled by the central processing unit.

The read head mechanism (assembly) and carousel housing are heated by heater mat secured to the base of the read head. The read head heated mat has embedded thermistor serving as a sensor. The temperature can be set between 37° and 39° C. The read head heater mat can be supplied with a voltage ranging from 0 V and −15 V as opposed to ±15 V as are all other mats. This gives the read head heater mat a 15 W full power level. The heater mats are preferably constructed of silicon rubber with internal sensors comprising thermistors. The carousel and reader head mats, contain integral thermal cutouts. External thermal cutouts can be used on the wall mats, During warm-up phases, full power is directed to all heater mats. Once the duty cycle of each channel drops below a pre-determined level as the unit approaches steady state temperatures, the power supply is reduced to 25% full power.

Processor Heating System

Temperature control of the processor at the processing station comprises a processor heating system 630 (FIG. 31) which includes a forced convection system to maintain air temperatures where the test packs are processed and a conductive system to apply heat directly to the test pack when the test packs are tested and processed in the clamped position. In order to maintain the test packs at the desired temperatures in the processing station, both the convection and conductive heating systems are preferably operated simultaneously. The heaters of the processor heating system are insulated by low density polyurethane insulation.

The convective system comprises: a left hand side wall heater 631, a right hand side wall heater 633 and a fan 634 to circulate the heated air. The side wall heaters 631 and 633 comprise heater mats which are secured to metal backplates of the processor to regulate and control the temperature of the processor. The plates are attached to the front left and right hand side of the processor module at the processing station. A single thermistor mounted in the right heating mat (right hand side wall heater) 633 is used to control the temperatures of the right and left side wall heaters 631 and 633. The heating mats comprising the left and right side wall heaters 631 and 633 can be maintained a temperature of 41.5° C. A fan 634 mounted in front of the processor circulates the heated air between the plates and directs the heated air at about 38° C. to the test packs.

The conductive system in the processing station includes a clamp plate heater 655 (FIG. 31) comprising a silicon heater mat. The clamp plate heater 635 is secured the clamp plate assembly, which clamps and holds the test packs in the processing station. The clamp plate heating mat can provide 60 W of power and has a thermistor to maintain the clamp plate surface against the test pack at a temperature between 37°–39° C.

The heater mats of the processing heating system 630 can be of silicon rubber construction with interval sensors comprising thermistors. The clamp plate heating mat can contain an integral thermal cutout. The left and right side wall heating mats can have external thermal cutouts. Sample rate can be 10 Hz and pulse width modulation is used to provide efficient power usage.

During warm-up phases, full power is directed to the heating mats. Once the duty cycle falls below a predetermined level as the unit approaches steady state temperatures, the power supply to the heating mats are reduced to 25% full power. In use, the processing heater is positioned in the processing station and assembly to heat the metal plate so as to heat and maintain the temperature of the samples in the test packs undergoing tests in the processing station.

Electrical Controls

The motors in the automated diagnostics instrument are controlled by the same basic servo control system. The servo control system has servo control loops which are responsible for the positional and movement control of the servo motors including a DC motor with an integral gearbox. A motor position encoder comprises a counter which shows the position of the servo motor. The counter can be incremented for every clockwise movement of the motor and decremented for every counter-clockwise movement. Once a known position (datum) has been located, the motor is then able move to any other position with great accuracy. The motor drive circuit is responsible for delivering the amperage and voltage required to move the motor. The preferred circuits are capable of delivering up to two amps at 12 volts to move the motor either clockwise or counter-clockwise. The servo channels are responsible for controlling the movement and action of the following mechanical subassemblies:

(a) the load tram which moves one test pack from the load door to any of ten positions on the carousel or vice versa, as well as permits the test packs to be loaded or unloaded from the diagnostics instrument;

(b) the process tram which moves one test pack from the processing station after it has been tested to any one of ten positions on the carousel or vice versa;

(c) the carousel which moves the test packs past the read head to the load tram and process tram;

(d) the read head which senses the presence of fluorescence in the test packs;

(e) the roller cam of the saddle assembly, which raises and lowers the high pressure roller, low pressure roller, reaction area sealer, and side blister sealer; and (f) the expression shoe cam of the saddle assembly which opens (bursts) is responsible for the resuspension and expression of side blisters.

Test Packs The test specific pack (TSP) 200 (FIG. 6) is a disposable pack that is used perform a complete test on a patient sample. Each test pack is: (a) test specific— for example, the MTB test pack contains reagents that specifically test for the presence of M. tuberculosis in a sample; (b) disposable—each sample is tested in its own test pack which is discarded after use; and (c) closed—the contents of the test pack are protected against contamination that would invalidate test results. At the same time, the risk of operator exposure to biohazardous materials is minimized. The test packs 200 are closed, disposable containers that are pre-filled with all required reagents, injected with the sample, and then loaded into the automated diagnostics instrument for testing as shown in FIG. 2.

The test pack 200 (FIG. 6) has a flexible, transparent plastic, closed disposable pack 216; a translucent white, semi-rigid plastic backplate (backing plate) 204 providing a tray; a transparent plastic read cell window 212; a thermally conductive black cover plate 218 providing a heating plate and read cell heater; and a sample port 220. The closed disposable pack 216 has: a read cell 213, a series, set or array of reagent blisters (burstable blisters) 222; five reaction areas 224–228; an amplification overflow and containment area 229; four waste areas or pouches 230–233; a sample passageway 221 and an amplification passageway 237. The thermally conductive cover plate 218 can be made of metal or other thermally conductive material. The read cell 213 is an integral part of the closed disposable pack 216. The read cell 213 fits within, is aligned with, and protectively covered by the read cell window 212. During manufacturing and reagent filling, the closed disposable pack 200 (FIG. 7) has inlet loading blisters 234 which are filled with reagents and are cut off (severed) after the reagents are injected, passed or otherwise expressed into the reagent blisters 222. Some of the reagent blisters may not be filled for some test protocols.

Figure 7:
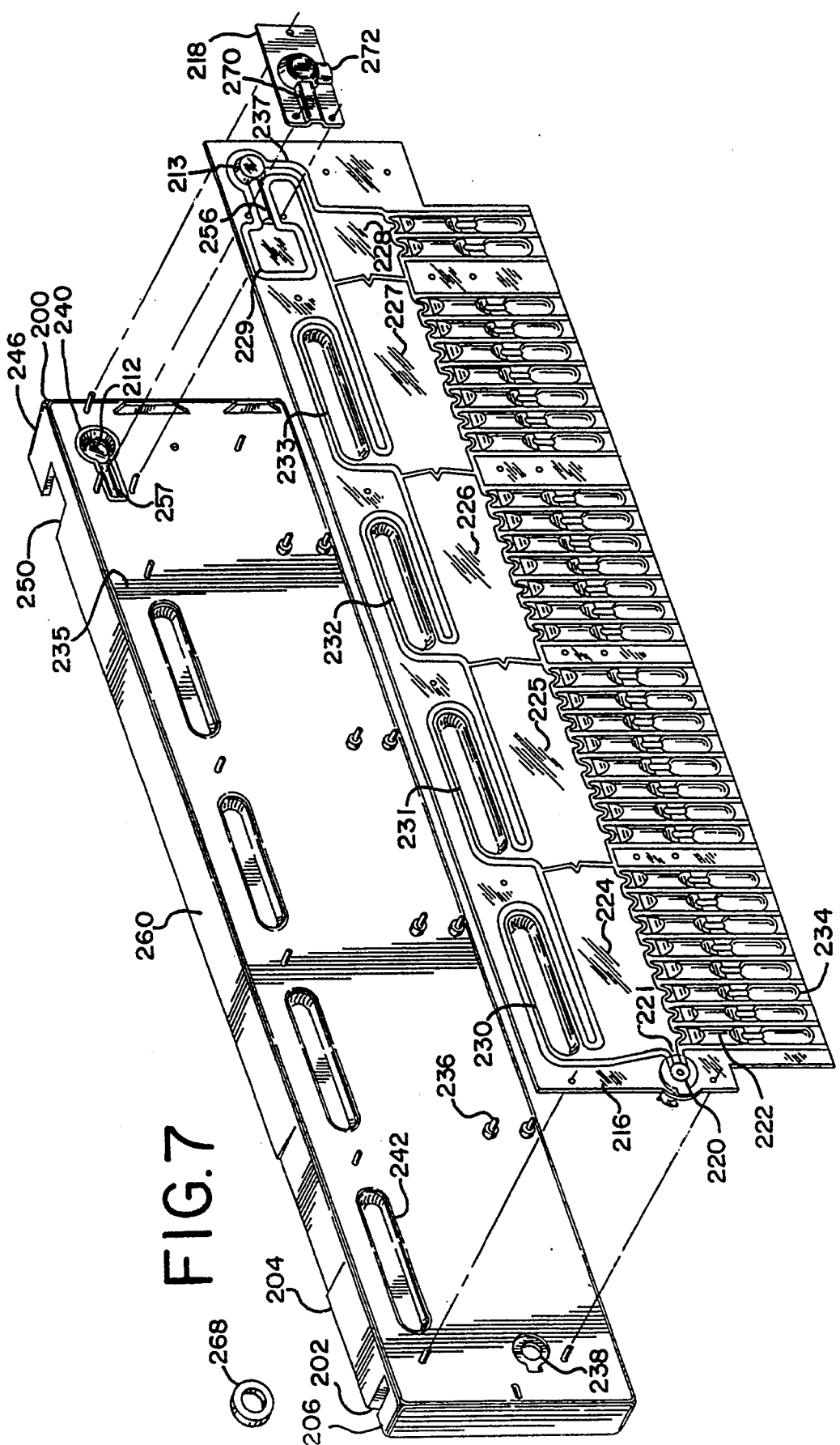
FIG. 7 is an assembly view of the test pack.

As best shown in FIG. 7, the front 235 of the backplate 204 has: (a) connecting pins or pedestals 236 which receive and are heat sealed to the closed disposable pack 216 and the thermally conductive cover plate 218; (b) a recessed sample port hole 238 which receives the sample port 220; (c) a keyhole-shaped read cell opening or hole 240 to receive the read cell window 212; and, (d) oblong chambers or recesses 242 which support and receive the wash chambers 230–233. The back (rear) 243 of the backplate 204 has: an upper carrier portion 206 (FIG. 23) with a lateral guide slot 202 providing a groove to receive and ride upon the tram rail; a U-shaped locking pin-receiving groove and socket 244; a lower carrier portion 246 (FIG. 22) with a circular locking pin-receiving groove and socket 248; a U-shaped channel or groove 250 to accommodate the read head; and four read cell docking vanes 252–255 comprising tapered ribs whose axes intersect through the read cell window 212 and read cell 213. Locking pins engage the locking pin sockets 244 and 248 at the processing station to secure the test pack 200 during processing of the test pack. The docking vanes 252–255 provide part of the docking mechanism which aligns in registration with, telescopically receives, nests with and matingly engages the read head. The transparent plastic read cell window 212 and read cell 213 each have an elongated read cell chimney 256 and 257. The intermediate central rearward (back) portion of the backplate 204 has four square magnet-engaging areas or recesses 258 (FIG. 10). The elongated longitudinal identification (ID) side 260 (FIG. 24) of the backplate has identification stickers or labels 206 and 208 to identify the test and patient sample.

As shown in FIG. 23, the sample port 220 has a conical socket 262 with a lock fitting 264 and stem 266. A removable sample inlet cap or plug 268 covers the sample inlet port 220. The cap 268 is removed during injection of the inlet sample.

The thermally conductive cover plate (heating plate) 218 (FIG. 7) has a key-hole shaped read cell window—receiving chamber or recess 270 in communication with a lateral sample passageway—receiving chamber or recess 272. The thermally conductive cover plate 218 covers, receives, secures and transfers heat to the read cell window 212 and read cell 213.

Test packs are preferably delivered in secure boxes, all of the same test-type and lot. Each test pack in the box is individually packaged in a protective foil and light-tight envelope. Each box can be labeled with: test type (for example, MTB for M. tuberculosis); lot number to track how and when the pack was manufactured; and, expiration date for the test pack. Each box of test packs also includes two quality control samples that the operator injects into test packs and runs through the instrument as part of an ongoing quality control procedure to verify instrument and test pack performance.

Sample processing tubes can be used to hold the sample before it is injected into the test pack. The processing tube can be designed to work with a sample transfer device and can be optimized for any special pre-processing that might be required for the sample. Sample transfer devices can be used to allow the operator to inject the correct amount of the sample directly from the sample processing tube into the test pack. One end attaches to the sample processing tube and the other end screws into the test pack. A filter can be used in the sample transfer device to ensure that only a clear sample is delivered into the test pack. A loading nest can be provided to support the test pack while the operator injects a sample into the pack. The loading nest resists movement while the operator attaches the sample transfer device to the test pack.

Each new, unused test pack includes reagents and materials comprising: probes, diluents, magnetic beads, washes, eluants, nucleotide mix, and Q-beta replicase enzyme. Reagents can perform the reversible target capture ("RTC") chemistry. The reagents are located in the blisters on one side of the test pack. The probes bind to the target nucleic acid sequence so it can be isolated and then detected. Two types of probes can be used: detector probes and capture probes. The diluents reduce concentration of solution to facilitate capture of target-probes complex. The magnetic beads capture the target-probes complex. Washes remove background materials and unused reagents. The eluants remove the target nucleic acid sequence from the magnetic beads. The nucleotide mix provides an environment that facilitates amplification of a nucleic acid segment, and can also include the fluorescent dye propidium iodide ("PI"), which binds into the nucleic acid segment that will be amplified. Q-beta replicase enzyme can promote amplification of the nucleic acid segment, whose fluorescence can be detected by the read head of the optical reader.

A sample port 220 (FIG. 23) allows the operator to inject the sample to be assayed into the test pack. The sample port is on the back of the test pack. Reaction areas in the closed disposable pack provide a location for sample and reagents to mix. The five reaction areas 224–228 (FIG. 6) in the closed disposable pack are located along the center of the pack. Waste pouches 230–233 in the closed disposable pack store waste fluids from each stage in the assay process. The four waste pouches, which are located along the right ID side 260 of the test pack, are empty when the test pack is new. A read cell 212 (FIG. 22) holds the final product sample of the reaction and allows the optical reader to read the fluorescence of the sample pack. A thermally conductive cover plate 218 protects the front of the read cell.

Figure 4:
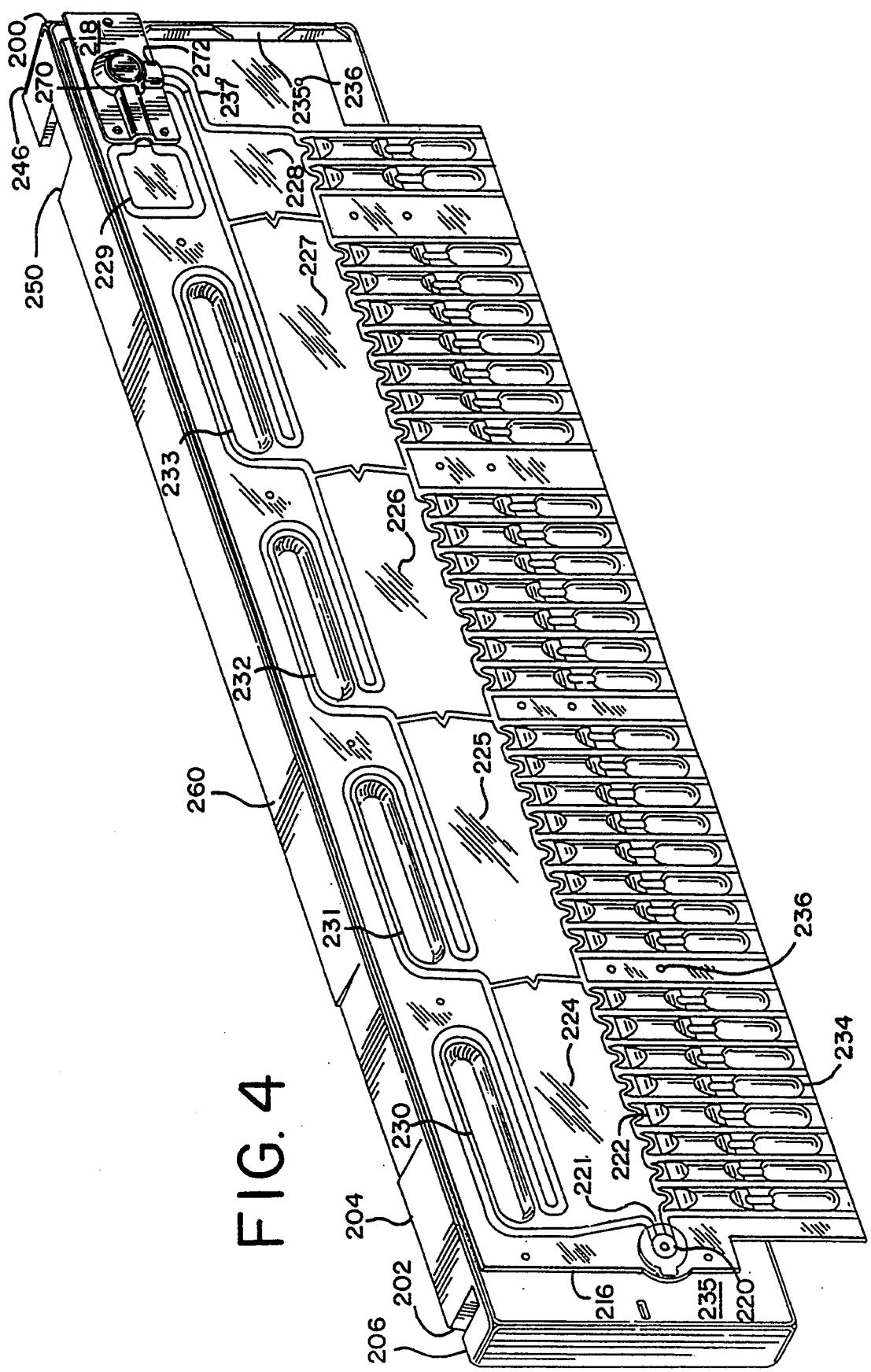
FIG. 4 is an enlarged perspective view of a test pack before the inlet filling section of the disposable closed pack has been injected with reagents and fluids and severed.
Figure 5:
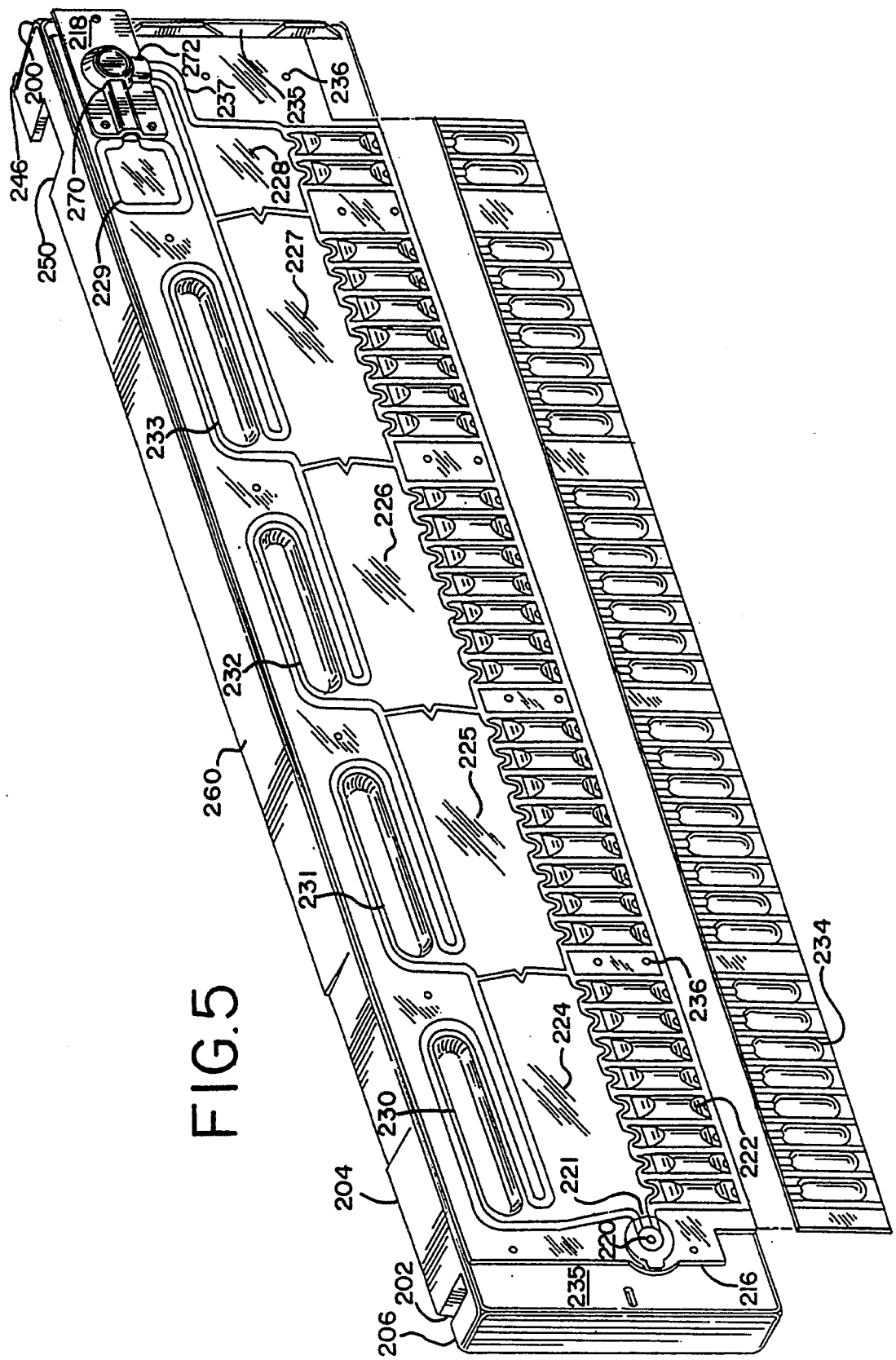
FIG. 5 is a perspective view of the test pack after the inlet filling section of the disposable closed pack has been injected with reagents and fluids and severed.

The reagent blisters 222 (FIG. 4), inlet loading (filling) blisters 234, and waste pouches 230–233 of the closed disposable pack can be formed from a single sheet of clear, non-reactive material. This formed piece is affixed to the tray comprising the test pack's rigid plastic backplate. The sample port is molded as part of the backplate. The read cell is formed from an optically clear and rigid plastic, and is affixed to the backplate during manufacture. Burstable seals in the closed disposable pack temporarily close reagent blisters and separate reaction areas from each other in the closed disposable pack. As the test pack is processed, the automated diagnostics instrument bursts the reagent blisters to introduce reagents into a reaction area and to move the contents of one reaction area to the next. During processing, permanent heat seals are applied to close emptied blisters, vacated reaction areas and filled waste pouches to keep liquids from being pushed back into them.

The sample port 220 (FIG. 23) on the back 243 of the test pack is where the operator injects the patient sample into the test pack. The sample port can comprise a conical socket 262 with a Luer-type lock fitting 264 which exactly fits and locks to a sample transfer device, ensuring injection of the correct volume of sample and eliminating the chance of leakage during injection. The sample inlet cap 268 can comprise a conical Luer-type plug that covers the sample port. The sample inlet cap can be affixed to the sample port during manufacture, and is preferably only removed to insert the patient sample. Then, the cap should be replaced.

The optical reader of the automated diagnostics instrument determines the result of each patient assay by reading the level of fluorescence detectable in the read cell window 212 (FIG. 22) after test pack processing is complete. In order to provide a precisely defined shape for reading, the read cell window on the back of the test pack is preferably arranged and constructed with a rigid, flat planer surface that is optically clear. The read cell window is recessed for protection against damage, fingerprints, scratches and dirt. The back of the read cell 212 is reinforced by a thermally conductive, metal cover plate 218, which is visible from the front of the test pack. The thermally conductive cover plate 218 also conducts heat from the carousel base and controls the temperature in the read cell, such as during amplification. The volume of liquid in the read cell is controlled by precise reagent and sample volume, as well as back pressure caused by air moved out of the read cell into the read cell pillow on the front and chimney on back of the tray (backplate) of the test pack.

As shown in FIG. 24, a bar code sticker (label) 206 can be attached such as when the test pack is manufactured. A sample bar code sticker (label) 208 can also be affixed by the operator when preparing the test pack. In the preferred embodiment, a multi-digit identification (ID) number on this bar code sticker uniquely identifies the sample. This bar code sticker contains information that uniquely identifies the test pack, and allows details about its manufacture to be traceable. Bar code stickers identify: test type; lot number to track pack manufacture; serial number to uniquely identify the test pack; and, expiration date (month and year) for the test pack. An actual manufacturer's bar code sticker would identify a specific test, lot, and serial number. The preferred bar code stickers enable the automated diagnostics instrument to keep track of each test result. Two types of stickers can be provided: (1) sample ID number stickers to designate unique ID numbers in each box of test packs; and (2) quality control information stickers to specify a unique quality control ID number for the sample. Each unique ID number on the bar code stickers can include: a digit (1, 2 or 3) that identifies the test pack contents wherein the number "1" identifies a patient sample, the number "2" identifies a positive quality control sample, and the number "3" identifies a negative quality control sample. Each bar code sticker can have a multi-digit sample ID number and a multi-digit internal control number.

The test packs 200 (FIG. 7) provide a test pack sampling assembly with a closed disposable pack 216 and an impact resistant tray (backplate) 204. The closed disposable packs have burstable blisters 222 which contain reagents for selected tests as well as reaction areas 224–228 in which the reagents are mixed with the sample to conduct the desired test. The disposable packs also have waste pouches 230–233 to contain washed background material and waste. The closed disposable packs are made of flexible transparent plastic to permit viewing of the reagents and samples contained in the packs. Each closed disposable pack has a read cell, also referred to as a read cell window 212 to contain and display optically detectable analytes.

The impact-resistant trays are preferably molded of impact-resistant plastic and provide backplates to support the closed disposable packs. The trays have closed disposable pack-receiving surfaces which are shaped complimentary to the mating surface portions of the closed disposable packs to matingly engage and rigidly support the closed disposable packs. Each of the trays has and defines a window-receiving opening 240 (FIG. 7) which is positioned in alignment with the read cell of the mating disposable pack. Each tray also has a horizontally-slotted upper carrier portion 206 (FIG. 23 ) with a laterally-extending horizontal slot 202 and also has a lower carrier portion 246 (FIG. 22). The trays also have posts 236 (FIG. 7) which are secured, such as by heat bonding, to the closed disposable packs. For identification purposes each of the trays of the test packs have labels, 206 and 208 (FIG. 24), such as self-adhesive labels, which are attached to the trays. The labels have bar codes which correspond to the desired test to be conducted and identify the samples and patient.

Advantageously, each of the test packs has a transparent, impact-resistant read window 212 (FIG. 22) which is secured to the tray in the window-receiving opening. The read window firmly engages and contacts the read cell to permit viewing and reading of the optically detectable analytes in the read cell of the closed disposable patio. Preferably, the read cell is key-hole shaped and the tray has inclined, tapered docking fins 252–255 positioned about the read cell to provide part of a docking mechanism to facilitate alignment and coupling of the read head of the optical detector and the read cell window.

Figure 6:
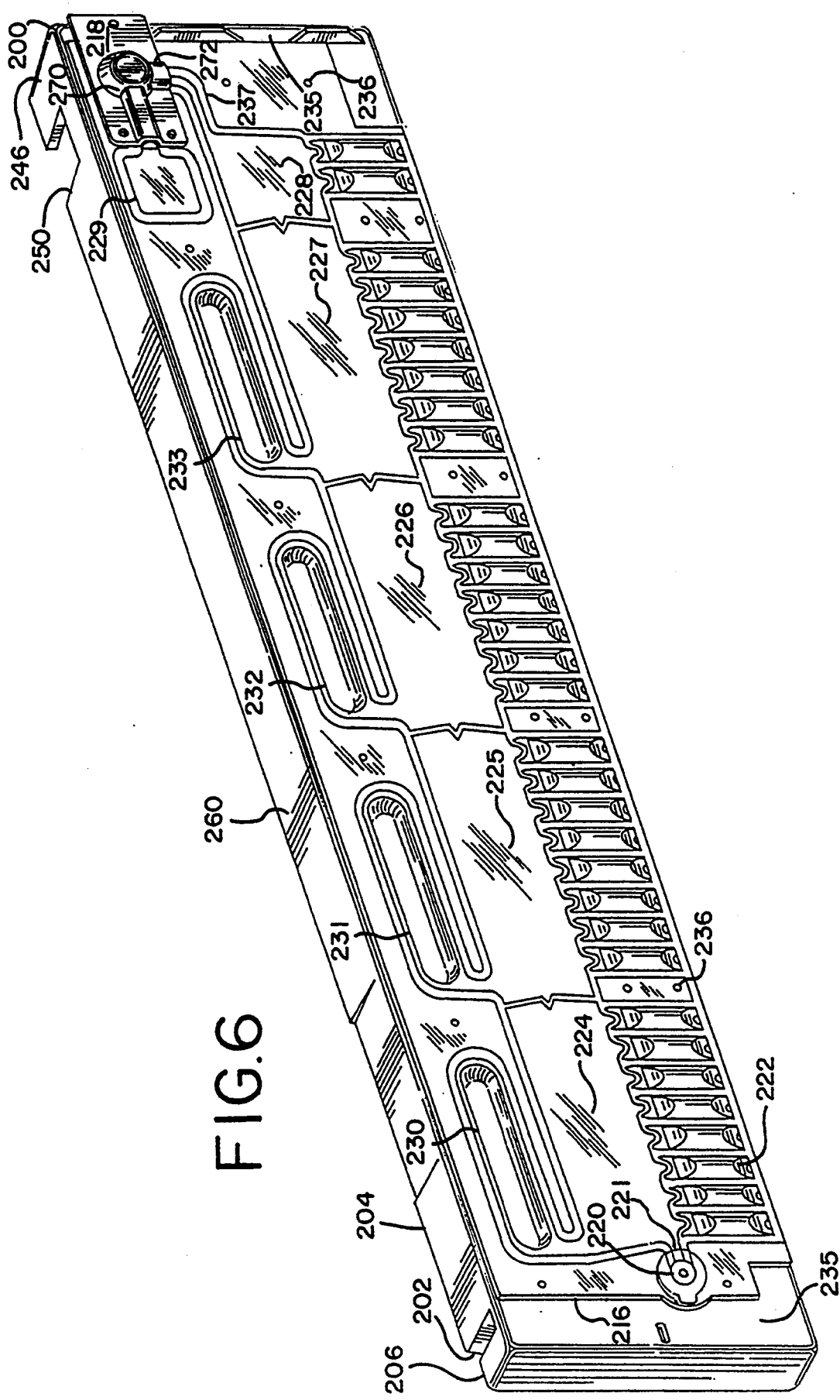
FIG. 6 is a perspective view of the test pack.

The test pack also has a thermally conductive plate 218 (FIGS. 6 and 7) secured to some of the posts 236 of the tray. The posts are secured to the thermally conductive plate and closed disposable pack by an enlarged over-hung crimping portion caused by heating the unattached cantilevered portions of the post beyond its melting temperature. The thermally conductive plate engages the closed disposable pack about the read cell and conducts heat to enhance amplification. The thermally conductive plate has an outwardly-extending circular portion 270 about the read cell which provides a containment area and support pocket for the optically-detectable analyte in the read cell The test pack has a totally contained plastic bag comprising a disposable closed pack with compartments to carry out a series of chemical reactions. The closed disposable pack has blisters to contain and, when squeezed, to allow efficient suppression of fluids. The blisters include filling blisters (inlet loading blisters) 234 which provide a contamination-free filling system with air-free vertical filling. The filling system and method also allow for any overflow fluids to be sealed and disposed of correctly. The test pack has a read cell 213 (FIG. 27) which is contained within the closed bag (closed disposable pack) and is designed to be bubble free, to be always full and to have a slight pressure to ensure that the shape is fully maintained. The read cell window ensures good optical quality. Good temperature stability of the read cell is accomplished by contact with the thermally conductive cover heating plates 218 (FIG. 6). The read cell engages, couples and cooperates with a read head assembly. The read head assembly has a conical read head for successive reads and reposition which are taken with high repeatability of the read head position, thereby giving good repetitive results from a fiber (fibre) optic reader.

During testing the closed disposable packs undergo magnetic separation by rollers and a series of magnets since the sealed area fluid and magnetic particles need to be separated. The physical parameters are such that the fluid and magnetic particles are positioned in the presence of powerful magnets. Due to the fluid dynamics, the ability to do this may require one or two rollers to reduce the fluid velocity and thereby allow the magnetic particles to be separated by the close presence of a magnetic field.

The closed disposable packs can be manufactured from plastic film. Preferably, the chambers and features of the vessel provide a bag comprising the closed disposable pack are formed by welding two films of plastic. The preferred plastic film is manufactured by DuPont de NeMours and sold under the trade name Surlyn ®. Surlyn ® is an ionomer resin thermoplastic containing both covalent anti ionic bonds. The ionic intercharge electrostatic forces are very powerful and thermally reversible at temperatures varying from 175° C. to 290° C. Two sheets of Surlyn ® plastic can be placed together during the manufacturing process with one or both of the sheets heat-formed to the shape required on a continuous speed production process and one sheet laid top of the other. Permanent bonds may be formed between the two films to form chambers, passages and seals. In addition, semi-permanent bonds can be formed to serve as burstable seals. These bonds are made with heated filaments, or by other plastic welding techniques. The duration of heat, compressive pressure exerted on the two films, temperature of the filament and cooling time influence the nature of the bond.

The difference between breakable seals and permanent walls in the closed disposable packs are a matter of degree. Permanent walls tend to retain integrity up to 50–60 psi. Burstable seals tend to rupture at pressures of between 10–30 psi. Such permanent seals or walls are made with a wider filament capable of operating at a higher temperature. The wider high temperature element is held against the two sheets at higher compressive pressure, for a greater time and cooled more slowly than burstable seals in the closed disposable packs.

The test pack vessel (closed disposable pack) has a first reaction area which is adapted to receive a solid support, a test sample and at least one first probe capable of associating with the support and the target to form a support-probe-target complex upon imposition of probe-binding conditions, leaving sample debris free in solution. A sample is introduced into the first reaction area through the sample port. After the sample has been introduced into the reaction area, the sample port can be sealed. The probe(s) can be contained in one of the reagent blisters, and can be forced into the first reaction area of the closed disposable pack by applying pressure to the blister. (The pointed center of each burstable seal adjacent to each blister, or between reaction areas, is the weakest part of the seal, and can be ruptured by applying pressure to the blister of the reaction area by the action of a roller of a shoe.) Addition of the probe to the reaction area allows the probe to form a probe-target complex, prior to binding to the support, while the prove and the target-containing sample are in the reaction area.

In assays which employ a two-probe system, wherein one detection probe is capable of producing a detectable response, and a second capture probe is capable of capturing a detectable probe-target complex to a solid support, it may be advantageous to allow the sample and the capture probe to hybridize prior to capture on supports. Capture of the capture probe on the support prior to the capture probe hybridization target, impairs the kinetics of the binding of probes to target, requiring a hybridization of longer duration or resulting in less efficient hybridization. The test pack facilitates hybridization of the probes to the target by maintaining the support separate from the sample during an initial hybridization. Such hybridization may take place in any reaction area, but typically the first and/or second reaction area.

Following hybridization, magnetic supports or magnetic beads are preferably received within the first reaction chamber. Magnetic supports in the form of metal beads (particles) can be contained within a support chamber, i.e. a reagent blister containing the magnetic particles. In order to facilitate the filling of support chamber, the closed disposable pack can be equipped with filling chambers (inlet loading blisters) 234 (FIG. 4), which allow the test pack to cooperate with filling nozzles, funnels, etc. After the supports have been loaded into the support chamber, the filling chambers are no longer needed and are severed and removed. A permanent seal is welded between the upper and lower plastic sheets, sealing the support within the support chambers, which become closed cells.

The magnetic beads can carry primary amine or carboxyl functional groups which facilitate covalent binding or association of a probe to the magnetic support particles. The support beads can be single domain magnets and superparamagnetic so as to exhibit little or no residual magnetism. The magnetic support is preferably capable substantially homogeneous dispersion within the sample medium and includes at least one antiligand moiety capable of binding to a ligand under binding conditions to form a target-probe support complex.

After the target and the probes have been allowed to hybridize under binding conditions within the reaction chamber, the magnetic supports held in the support chamber are expressed into the reaction chamber by the shoes. A gate is interposed between the magnetic support chamber and the reaction chamber (reaction area) to separate the chambers until the shoe is exerted on the support chamber. After the magnetic support has entered the reaction chamber, the support chamber is permanently sealed from the reaction chamber, to avoid fluids backing up into the chamber.

The magnetic supports which are present in the reaction chamber (reaction area) are mixed to provide contact and dispersion within the reagent solutions retained in reaction chamber. The flexible plastic closed disposable pack allows for mixing of solutions by simply rolling across the closed disposable pack body. The probe-target complex is allowed to bind to the magnetic support and the magnetic support is immobilized.

The backing plate or tray can be equipped with hollowed out/indented areas towards the back side of the plate to allow the magnets to be positioned in close proximity to the supports. The use and need for such magnetic support indentations are dependent upon the thickness of the backing plate and the strength of magnets used for immobilization. During immobilization, the sample debris is separated from the target-probe support complex by compressing the reaction chamber (reaction area) to urge solutions through the effluent passage and into an effluent chamber. The passage between the effluent chamber and the first reaction chamber can be closed by compressive clamping pressure on the passage.

Following removal of solutions/reagents containing sample debris from the first reaction chamber, the magnetic supports and the walls of reaction chamber may contain further non-specifically bound sample debris. In order to solubilize or suspend such further sample debris, the magnetic supports are further washed. A series of wash chambers 230–233 are formed in the top and bottom (first and second) plastic films. Each wash chamber is blistered and each closed disposable pack has a blistered filling chamber to accommodate nozzles, tubes, funnels, etc. After the filling operation is complete and fluids are retained within the wash chambers, each wash chamber is sealed by the formation of a permanent seal.

Each wash chamber is separated from the reaction chamber by a burstable seal. Upon imposition of shoes on the first wash from the first wash chamber, the wash breakable seal opens and allows the solutions retained within the wash chamber to enter the reaction chamber. Upon suitable mixing, the magnetic supports are immobilized within the first reaction chamber and the wash solutions removed through effluent passage into the effluent chamber. In order to avoid back flow of solutions into any of the open wash chambers, each chamber can be permanently sealed after solutions have been removed therefrom. Following the wash from the solutions in the first wash chamber, the supports retained in reaction chamber are washed sequentially with the solutions retained in the second wash chamber and, in a similar manner, the wash solutions retained in the third wash chamber. This wash may be repeated additional times if there are additional blisters containing wash solutions. During each wash. magnetic supports are retained in the reaction chamber and wash solutions are removed from the reaction chamber by effluent passages into the effluent chamber.

The antiligand system of the support and probe can be reversible to allow a probe-target complex to be removed from the magnetic support. The test pack can utilize homopolymer nucleic acids, ligands and antiligands. One homopolymer nucleic acid can be associated with a magnetic particle and a complementary homopolymer nucleic acid can be associated with the probe. Such homopolymers can be released upon suitable release conditions such as alternations in temperature, pH, salt strength, etc.

The magnetic supports (metallic beads) used within the reaction chamber (reaction area) of the closed disposable pack may hold unacceptable levels of non-specifically bound probe and sample debris. In solution, the target-probe complex is removed from the first reaction chamber through a burstable seal into a second reaction chamber. The second reaction chamber of the closed disposable pack is formed between welds of the top and bottom (first and second) sheets of film of the test pack. The second reaction chamber is blistered to accommodate fluid volumes.

In order to separate the target and probe complex from the support, the vessel comprising the closed disposable pack can carry eluent solutions within an eluent chamber. The eluent chamber is maintained separate from first reaction chamber by a breakable seal. Compression of the eluent chamber urges eluent solutions through the burstable seal and into the first reaction chamber. Eluent solutions are mixed with the magnetic support by rolling the solutions throughout the first reaction chamber. Under appropriate release conditions, the target-probe complex is released from the support. Solutions carrying the target-probe complex are urged through a breakable seal separating the first reaction chamber from a second reaction chamber.

The first, second, third and fourth reaction chambers of the closed disposable pack can be maintained separately from each other by a permanent seal. The first, second, third and fourth reaction chambers (areas), blisters, etc. of the closed disposable pack are structurally and functionally similar. Following recapture of the target-probe complex on supports and subsequent washes with wash solutions maintained in first, second and third wash chambers, removal of solutions through a passage into an effluent chamber, the target-probe complex can be released from the second support by eluent solutions maintained in an eluent chamber in a manner as that described with respect to the first reaction chamber. As with the first reaction chamber, following removal of solutions from wash chambers and eluent chambers, such chambers can be permanently sealed to avoid back flow of solutions into such chambers. Eluent solutions carrying the target-probe complex released from the support are urged through a second chamber breakable seal into a third reaction chamber. After solutions have entered the third reaction chamber, the third reaction chamber can be closed to the second reaction chamber by the formation of a permanent wall or seal. The function and operation of the components and elements associated with the third reaction chamber are identical to the function and components associated with the second reaction chamber following capture of the target-probe complex on a support and subsequent washes, the target-probe complex is released from the support. Eluent solutions containing the target-probe complex are urged through a burstable seal by compressing the third reaction chamber. Eluent solutions containing the target-probe complex pass through burstable seal into a fourth reaction chamber. The function and components associated with the fourth reaction chamber are similar in structure and operation to second reaction chamber and third reaction chamber. Eluent solutions for solubilizing the target-probe complex after washes can be maintained in blistered eluent chamber separate and apart from the fourth reaction chamber by means of a burstable seal. In the event additional washes or eluent solutions are desired, they may be carried in extra chamber. Following capture of supports, washes and elutions from such supports, the elution solution held in fourth reaction chamber can be forced through a breakable seal into a fifth reaction chamber. In order to maintain fifth reaction chamber separate and apart from fourth reaction chamber, a permanent seal can be welded into the top and bottom (first and second) sheets of the test pack. A read chamber (read cell) is maintained separate from the fifth reaction chamber in order to allow mixing of the reagents prior to moving them to the read chamber. Complete mixing prior to reading the signal can produce more consistent readings.

Desirably, one of the probes has a label capable of detection. Reagents to facilitate production of a detectable response can be carried in a detection chamber. In the event that the probe includes a replicatible entity, such as MDV-1 or like sequences, the detection chambers can contain an enzyme, Q-Beta replicase, anti necessary cofactors and agents. In the event that the probes include MDV-1 or like sequences that are replicated by the enzyme Q-Beta replicase during a detection phase, one of the reagents of detection may include propidium iodide. Desirably, the read chamber allows fluorescent detection of propidium iodide outside the fifth reaction chamber.

The test packs are capable of performing four reversible target capture cycles in a closed environment with amplification of a detectable moiety. The signal from the detectable moiety can be detected outside of the vessel. The closed disposable packs can contain different reagents for performing different tests in the processing station of the automated diagnostics instrument.

Operation

When an operator inserts a test pack 200 (FIGS. 2 and 3) containing a patient sample in the load door 110 and closes the door, many functions take place. Bar code readers 304 and 306 (FIG. 10) scans bar codes 206 and 208 (FIGS. 24) on the test pack that contain unique numbers that the automated diagnostics instrument uses internally to keep track of each sample. A load tram 300 (FIG. 10) takes the scanned test pack from the load door to a carousel 400 (FIG. 9). The carousel holds the test packs while the sample incubates and also while the test packs are in between processing station steps. The processing tram 302 (FIGS. 9 and 14) takes the test pack from the carousel 400 to the processing station 602 and back to the carousel. The processor 600 at the processing station 602 (FIGS. 8 and 9) manipulates sections of the test pack to introduce and mix reagents with the sample and then performs mechanical operations on the resulting mixtures. The read head 504 (FIGS. 9 and 30) scans each test pack for fluorescence in the final reaction stage to determine if the sample is negative or positive. Finally, the load tram 300 (FIG. 9) takes the processed pack back to the load door 110 (FIG. 2) for removal.

The automated diagnostics instrument can use nucleic acid probe technology fir the diagnosis of infectious disease. The principle of the test involves the isolation of a nucleic acid sequence, comprising a target that is unique to a specific microorganism. The method is capable of detecting small amounts of the target directly from a clinical sample. The target can be isolated through a series of binding and purification steps referred to as Reversible Target Capture ("RTC"), in which the target is temporarily captured while background materials are removed. Then, the target is released for additional purification. Ultimately, the target is detected through amplification of a detector material bound to the target. The binding steps can rely upon the Watson-Crick principle whereby complementary nucleotides form predictable base pairs (A-T, G-C, etc.). Specific nucleic acid sequences, called probes, are designed to bind (hybridize) to a known target. Probes hybridize because they contain sequences that exactly complement the target's nucleic acid sequence. In addition to the sequence attached to the target, probes have tails that are used in other reaction steps, such as target capture. "Probe sequence" generally means a specific nucleic acid sequence that exactly complements the target sequence and which hybridizes to the target under optimal chemical conditions. Probes allow the target nucleic acid sequence to be captured or detected in the sample. A capture probe binds first to the target and then to magnetic beads, allowing the beads to capture the target. A detector probe binds to the target to allow the diagnostics instrument to detect the target in the sample. A target-probes complex is formed when the capture and detector probes bind to the target. Hybridization is the process of forming a bond between a specific target nucleic acid sequence and a complementary sequence in a probe, resulting in a ternary complex called a target-probes complex. Capture is the process of bonding the tail of the capture probe to a magnetically attractable metal bead. Capture allows the target-probes complex to be removed from suspension, such as by magnets, while background materials are washed out of the sample along with any unhybridized probes. A diluent is a solvent introduced to dilute the concentration of solutes in the solution. Elution is the process of introducing a chemical solution (eluant) to remove absorbed materials (solutes). In these tests, the eluant is used to free the target from its captured state by breaking bonds either between it and its capture probe or between the capture probe and the magnetic particles on which it is captured. An intercalating dye is a dye that binds between base pairs in a replicating nucleic acid structure, becoming fluorescent to allow detection. Amplification is the process of stimulating replication of a nucleic acid sequence. Q-beta replicase is the replication enzyme used to make multiple copies of the detector probe.

The automated diagnostics instrument performs its analysis on samples whose target nucleic acids have been released from cells of microorganisms. The releasing mechanism differs from organism to organism. Analyte-specific test reagents are provided with the test packs and are identified by the bar code label (sticker).

After the test pack containing the sample is introduced into the automated diagnostics instrument, steps are performed to capture the target, remove background materials and then release the target. The first step is hybridization in which probes hybridize to the target nucleic acid sequence in the sample. Two types of probes are introduced into the first reaction area for hybridization: capture probes and detector probes. Magnets remove the magnetic beads and their captured target-probes complex from suspension while background materials are washed out of the sample, along with any unhybridized probes. An eluant releases the target from the beads so the target is available for additional purification. To increase the variety and amount of background materials removed from the sample, the automated diagnostics instrument performs a second cycle hybridization, capture, wash and elution using a different capture and release chemistry. Then, two more capture and release cycles further isolate the target in the reaction mixture. This strategy of using a series of different capture and release chemistries, each of which clears the sample of different materials, is called dual capture. The combination of reverse target capture (RTC) and dual capture helps purify the target nucleic acid. A total of four different RTC cycles are performed. Each cycle removes additional background material and unhybridized probes from the reaction mixture. In RTC cycle 1, the capture probe and detector probe hybridize with target. Magnetic beads bind to and retain capture probe during elution. In RTC cycle 2, a different capture probe hybridizes with target. New magnetic beads bind to capture probe, and then release probe during elution. In RTC cycle 3, target-probes complex are captured, washed and released. In RTC cycle 4, a final round of capture, wash and release is performed. After the RTC cycles are completed, the sample is substantially purified of background materials and is ready for the final amplification and detection stage. As a result of the four RTC cycles, one of the following results is returned: (a) a positive result is indicated by the presence of fluorescence (fluorescent detector probe attached to target); analyte (target); (b) a negative result occurs if there is no fluorescence of the target analyte. If the target is present, it is hybridized to both the detector and capture probes. The detector probe will be replicated (amplified) and the resulting fluorescence can be detected. If the target is not present, the detector probes have been washed out of the sample. Amplification will not occur and no fluorescence will be detected.

The processor 600 in the processing station 602 of the automated diagnostics instrument performs all of the stages in the reversible target capture (RTC) assay described above. Advantageously, all of the RTC processing stages and the subsequent target detection stage take place within a closed test pack that contains all the required reagents. The automated diagnostics instrument manipulates the test pack, releasing reagents into the sample, mixing, separating and washing the sample as appropriate. Preferably, all operations are precisely timed and volumes are controlled to provide optimal chemistry.

An operator or technician can prepare the test pack by injecting the sample into the sample port 220 on the back of the closed disposable test pack. The operator places the pack in the diagnostics instrument's load chamber (load station) and closes the load door 110, at which time the diagnostics instrument begins processing the test pack. In the processing station of the diagnostics instrument, capture and detector probes are expressed into reaction area through the blister's burstable seal, after which the blister is permanently heat sealed by the sealer assembly. One or more rollers 614 and 616 the saddle assembly 610 of the processor 600 mix the contents in the first reaction area. During first stage capture, the following reagents are introduced into reaction area: a diluent which serves as buffer to reduce the concentration of salt used in hybridization: and magnetically attractable metal-type bead(s) whose tails bind to the capture probe's tails. In the processing station of the diagnostics instrument, a diluent is expressed into the first reaction area from two blisters, after which the blisters are permanently heat sealed by the sealer assembly. Metal beads are mixed in their blister to return them to suspension, and are then expressed into the first reaction area after which the blister is permanently sealed by the sealer assembly 624. One or more rollers 614 and 616 of the saddle assembly of the processor mix the contents of the first reaction area. Then, the rollers move the contents to the bottom of the first reaction area, away from waste pouch. The test pack can be moved to the carousel by the processing tram for incubation, during which time the metal beads capture the target-probes complex.

During first stage washing, a wash material is introduced into reaction area of the closed disposable pack to remove background materials from the sample. Three sequential washes occur. In the processing station of the diagnostics instrument, magnets 606 from the clamp assembly 604 of the processor 600 pull the metal beads to the test pack backplate 204 so as to remove the beads from the solution along with the captured target-probes complex. The capture probe separates from the target, while the detector probe remains attached. The capture probe on the metal bead is later discarded along with the metal bead. Three washes are introduced into the reaction area of the closed disposable pack, one wash at a time. Each wash blister is permanently heat sealed by the sealer assembly 624 after the wash is expressed into the reaction area. After each wash is introduced, one or more rollers 614 and 616 mix the liquid in the reaction area and then push the waste liquid into the waste pouch. Then, the next wash is introduced. The first wash breaks the burstable seal that closed the entrance to the waste pouch. After the final wash, the entrance to the pouch is permanently heat sealed by the sealer assembly 624.

During first stage elution, a volume of elution buffer is introduced into a reaction area of the disposable closed pack to denature the bond between the capture probe and the target (analyte). In the processing station of the diagnostics instrument, an eluant can be expressed into the reaction area, after which its blister is permanently heat sealed by the sealer assembly 624.

The following processes occur during the second stage RTC cycle: (a) hybridization—the target/detector complex hybridizes with the second capture probe; (b) capture—the target-probes complex are captured on magnetic beads via capture probe; (c) wash—the background material is washed out of solution; anti, (d) elution—target-probes complex removed from the metal beads. A different type of capture probe is introduced for the second hybridization. In the processing station of the diagnostics instrument, the waste pouch is temporarily sealed by the wastegate 608. Capture probes are expressed into the second reaction area, after which the probe blister is permanently heat sealed by the sealer assembly 624. One or more rollers 614 and 616 distribute the solution in the second reaction area. Magnets 606 from the clamp 604 assembly of the processor 600 pull the metal beads in the first reaction area out of suspension, and then one or more rollers 614 and 616 push the liquid down to the second reaction area through the burstable seal that separates the reaction areas. The opening between the first and second reaction areas are permanently heat sealed by the sealer assembly 624. One or more rollers mix the contents of the second reaction area. Then, the rollers 614 and 616 move the contents to the bottom of the second reaction area, away from waste pouch. The test pack can be moved by the processing tram 302 to the carousel 400 for incubation, during which time the capture probe hybridizes with the target-detector complex.

During capture, the following reagents are introduced into the second reaction area of the closed disposable pack: (a) a diluent—the same buffer is introduced as was used in the first capture; and, (b) a type "B" metal bead, whose moiety binds to the capture probe's tail. In the processing station of the diagnostics instrument, the waste pouch is temporarily sealed by the wastegate assembly. Diluent is expressed into the second reaction area from two blisters, after which the blisters are permanently heat sealed by the sealer assembly 624. Metal beads are mixed in their blister to return them to suspension, and are then expressed into the second reaction area, after which the blister is permanently sealed by the sealer assembly. One or more rollers 614 and 616 of the saddle assembly 610 mix the contents of the second reaction area. Then, the rollers 614 and 616 move the contents to the bottom of the second reaction area, away from the waste pouch. The test pack can be moved by the processing tram 302 to the carousel 400 for incubation, at which time the new metal beads capture the target-probes complex.

During the second stage washing of the closed disposable pack, a high-salt buffer is introduced to remove background materials, especially non-specifically-bound probes. In the processing station of the diagnostics instrument, pneumatically operated magnets 606 of the clamp assembly 604 pull the metal beads to the test pack backplate 204, removing them from solution along with the captured target-probes complex. Three washes are introduced into a reaction area, one wash at a time. Each wash blister is permanently heat sealed by the sealer assembly 624 after the wash is expressed into the reaction area. After each wash is introduced, one or more rollers 614 and 616 mix the liquid in the reaction area and then pushes it up into the waste pouch. Then, the next wash is introduced. After the final wash is pushed into the waste pouch, the waste pouch is permanently heat sealed by the sealer assembly 624.

During the second stage elution of the closed disposable pack, a volume of low-salt elution buffer is introduced to drop salt concentration and thereby break the tail hybrids apart. In the processing station of the diagnostics instrument, eluant is expressed into the reaction area, after which its blister is permanently heat sealed by the sealer assembly. One or more rollers 614 and 616 mix the contents of the second reaction area. The test pack can be moved by the processing tram 302 to the carousel 400 for incubation. The capture probe separates from the magnetic bead. Both the capture probe and the detector probe remain attached to the target.

The following processes occur during the third stage RTC cycle: (a) capture—target-probes complex are captured on metal beads via a capture probe; (b) wash—the background materials are washed out of solution; and, (c) elution—the target-probes complex are removed from the metal beads. There is no need for an initial hybridization step, since the capture probe remains attached to the target at the end of the second RTC cycle. The same capture, wash and elution chemistries are used in the third RTC cycle as were used in the second RTC cycle. During the third stage, pneumatically operated magnets 606 of the clamp assembly 604 remove beads from solution in a reaction area of the closed disposable pack and then the rollers 614 and 616 wash the liquid down into the third reaction area through the burstable seal that separates the second and third reaction areas. The opening between the second and third reaction areas is then permanently heat sealed by the sealer assembly 624 and the magnets 606 retract. Diluent is then expressed into the third reaction area and the diluent blisters are sealed. Type B metal beads are introduced into the reaction area and its blister is sealed by the sealer assembly 624. The test pack can be moved by the processing tram 302 to the carousel 400 for incubation, during which time the beads bind to the capture probe on the target-probes complex. Three successive washes remove background material. Used wash liquids are moved into the waste blister which is permanently sealed by the sealer assembly 624 after the final wash. Eluant is expressed into the third reaction area, after which its blister is sealed. The test pack can be again moved to the carousel 400 for incubation, during which time the capture probe again separates from the metal beads. Both the capture probe and the detector probe remain attached to the target.

The following processes occur during the fourth stage RTC cycle: (a) capture—the target-probes complex are captured on metal beads via the capture probe: (b) wash—the background material is washed out of solution; and (c) elution—the target-probes complex are removed from magnetic beads. As in the third stage RTC cycle, there is no need for a hybridization step since the capture probe remains attached to the target at the end of the previous RTC cycle. The same capture chemistry is used in the fourth RTC cycle as was used in the second and third stage RTC cycles. However, different wash and elution chemistries are used in the fourth RTC cycle. The wash can be a pre-amplification wash buffer that is chemically compatible with Q-beta amplification. The same solution can be used for all three washes. The eluant can be a pre-amplification release buffer, such as a low-salt buffer in which Q-beta replicase can function. Both the capture probe and the detector probe remain attached to the target (analyte) after incubation. The eluant separate the target-probes complex from the metal beads.

The following processes occur during the fifth processing stage of the disposable test pack: (a) optional amplification, and (b) detection in which the read cell 212 of the test pack is scanned for fluorescence by the read head 504 of the optical reader. To promote amplification, the following solutions can be introduced into the fifth reaction area of the closed disposable pack: (a) a Q-beta replicase enzyme which replicates the detector probe; and, (b) a nucleotides mix such as a combination of nucleotides, propidium iodide (PI) and buffer. Propidium iodide is a dye that intercalates between base pairs in a nucleic acid structure and becomes fluorescent. In this case, it binds into the replicating detector probe sequences. During amplification in the processing station of the diagnostics instrument, Q-beta replicase enzyme and nucleotides mix can be introduced into the fifth reaction area of the disposable closed pack, and then their blisters are sealed by the sealer assembly 624. Pneumatically operated magnets 606 of the clamp assembly 604 pull beads in the fourth reaction area of the closed disposable pack out of suspension. One or more rollers 614 and 616 push the liquid down to the fifth reaction area of the closed disposable pack through the burstable seal that separates the fourth and fifth reaction areas. The opening between the fourth and fifth reaction areas can be permanently heat sealed by the sealer assembly 610 and the magnet 606 retracts. One or more rollers 614 and 616 can push the solution into the read cell 212. A permanent heat seal can be produced by the sealer assembly 610 to close off the area surrounding the read cell area to ensure a closed and fixed-volume environment for amplification of the sample. The test pack can be moved by the processing tram 302 to the carousel 400 for incubation. The test pack incubates briefly prior to the first reading at the read head 504, during which time amplification begins. A sample without the target nucleic acid sequence does not deliver the detector probe into the fifth reaction area.

The test pack's read cell 212 is scanned multiple times for fluorescence during the reading cycle by the read head 504 of the optical reader. During each reading, the automatic diagnostics instrument 100 senses the fluorescence present in the sample and records the amount of sensed/detected fluorescence in the computer. If the target-probes complex is not present, the propidium iodide dye will not fluoresce sufficiently for detection by the read head 504 of the optical reader. After the final reading, the diagnostics instrument evaluates all of the readings to determine whether the level of fluorescence establishes the presence of the target in the sample. Based on its evaluation, the diagnostics instrument 100 indicates one of the following results for the sample: (a) positive read out is indicated by a fluorescent analyte to indicate that the target is present in the sample; (b) negative readout occurs if there is no fluorescence which indicates that the target is not present in the sample. The result is displayed on the results database screen on the monitor 116 and can be printed by a printer attached to the automated diagnostics instrument.

In use, the test packs 200 to be analyzed are inserted and loaded in the load door 110 of the loading station where they are scanned, read and identified by the bar code readers 304 and 306. The load tram 300 transports the test packs from the loading station to the carousel 400. The carousel holds, carries, rotates and arcuately moves the test packs in a circumferential direction. The processing tram 302 transports the test packs from the carousel 400 to the processing station 602 and assembly where the tests are conducted on the samples in the test packs. The diagnostics instrument automatically diagnoses and analyzes samples in the test packs for analytes. Testing of the samples in the test packs occur in the processor 600 at the processing station 602. During testing, optically detectable analytes are formed as a result of the processing assembly (processor) 600 sequentially expressing, rolling and mixing reagents with the samples in the reaction areas of the test packs. In order to conduct the tests, blisters of reagents are compressed and burst in the test packs by the reciprocating impact shoe members 620 and 622 of the mixer assembly 618. During captures and washes, the targets (analytes) are attached (via capture probes) to the magnetic particles, which can be separated from the bulk of the solution. The waste remains in solution, and can be squeezed away from the particles. During elution, the targets are released from the particles, while some residual waste may remain attached to the particles. The targets, now free in solution, can the be squeezed away from the particles and moved to the next reaction area (chamber). The background material and waste portions are rolled into the test pack waste pouches by the rollers 614 and 616 of the roller assembly 612 and the waste pouches are thereafter heat sealed by the sealer assembly 610. The test packs are returned to the carousel 400 by the processing tram 302. The carousel 400 repeatedly moves and rotates the test packs in an upright position past the scanning station so that the read head 504 can optically scan and sense the optically detectable analytes in the closed disposable test packs over a period of time to confirm the diagnosis and test results and detect transitory optical changes in the analytes. The optically scanned and diagnosed test packs are withdrawn from the carousel 400 and transported out of the load station by the load tram 300.

Generally

The automated diagnostics instrument preferably conducts tests on the test packs based on the detection of nucleic acids unique to a specific microorganism. Tests performed by the automated diagnostics instrument are more sensitive than culture methods and may be more sensitive than antibody methods. Significantly, tests can be rapidly, accurately, and automatically performed, completed and analyzed by the automated diagnostics instrument in about four (4) hours in contrast to conventional common bacteria techniques which take 24-48 hours or conventional tuberculosis (TB) tests which take 4-6 weeks. Testing time by the automated diagnostics instrument is comparable to antibody techniques, but antibody detection test are not reliable until the patient develops an antibody which generally varies with the individual, and generally occurs 2-6 weeks post infection. In patients that are immuno-compromised, such as AIDS patients, antibody tests are not reliable.

Advantageously, tests are automatically conducted and analyzed on closed disposable packs entirely by the diagnostics instrument. This is in contrast to conventional culture techniques which are labor intensive, cumbersome, require manual interpretation of test results, and openly expose the test sample to the surrounding environment. Among the many advantages of the novel automated diagnostics instrument and process are:

1. Outstanding automatic performance.
2. Superior sensitivity.
3. Less sample contamination.
4. Ease of handling.
5. Fewer errors and interferences.
6. Uniform sample preparation.
7. Automated test pack handling.
8. Precision testing.
9. Accurate diagnosis.
10. Excellent repeatability and reproducibility of results.
11. Remote optical detection and bar code scanning.
12. Great quality control.
13. Good throughput.
14. Superb turnaround.
15. Low cycle and testing time.
16. Less contamination risk to operators, technicians and physicians.
17. Simple to use.
18. Safe.
19. Economical.
20. Efficient.
21. Effective.

Although embodiments of this invention have been shown and described, it is to be understood that various modifications and substitutions, as well as rearrangement of parts, components and process steps, can be made by those skilled in the art without departing from the novel spirit and scope of this invention.

What is claimed is:

1. An automated diagnostics instrument for analyzing samples in test packs for analytes, said instrument comprising;

processing station means for expressing and mixing reagents with samples in test packs to form optically detectable analytes and for separating and sealing waste portions of said samples from said analytes in waste pouches of said test packs;

sensing means for optically detecting said analytes;

carousel means for holding an array of test packs in an upright position and for intermittently and arcuately moving said test packs past said sensing means so that said sensing means can optically detect changing transitory optical characteristics of and confirm detection of said analytes at selected periodic intervals;

temperature control means for controlling the temperature of said samples including incubating means for heating the array of upright test packs in said carousel means and heating means for heating said test packs in said processing stations means;

processing tram means for moving said test packs from said carousel means to said processing station means and vice versa;

load door station means for ingress and egress of test packs;

load tram means for transporting said test packs from said load door station means to said carousel means and vice versa;

at least one of said tram means comprising a belt conveyor and a shuttle secured to said belt conveyor for detachably holding said test packs in an upright position; and said test packs comprising:

closed disposable packs having burstable blisters containing reagents for desired tests, said closed disposable packs comprising flexible light transmissible plastic having portions for viewing said reagents and samples;

impact resistant trays comprising backing plates for matingly engaging and rigidly securing said closed disposable packs, said trays defining a window-receiving opening in alignment with read cells and having horizontally slotted upper carrier portions and lower carrier portions, and said trays having posts secured to said closed disposable packs; and thermally conductive plates secured to said posts of said trays and engaging said closed disposable packs about said read cells.

2. An automated diagnostics instrument in accordance with claim 1 wherein:

each of said trays are encoded with indicia corresponding to a desired test and identification of the sample and patient;

said automated diagnostics instrument includes indicia reader means positioned in proximity to said load door station means for optically reading said indicia and identification of said trays; and a central processing unit for receiving signals from said indicia reader means and operatively connected to said processing station means for controlling sequences of operations of said processing station means.

3. An automated diagnostics instrument in accordance with claim 1 wherein:

said processing station means includes assaying means for nucleic acid assaying of samples in test packs by reversible target capture including hybridizing probes to nucleic acid sequence targets comprising said analytes in the samples, capturing the hybridized probes and targets on beads, magnetically removing the beads from suspension in the test packs, washing background material from the samples, and releasing targets from the beads with an eluant; and said sensing means includes read head means for detecting hybridized fluorescenced analytes.

4. An automated diagnostics instrument in accordance with claim 1 wherein said processing station means includes moveable saddle means for engaging test packs, said saddle means comprising:

roller means for mixing reagents and samples in reaction areas of the test packs and for moving background material comprising waste portions of the samples to waste pouches in the test packs;

shoe means operatively connected to the roller means for manipulating and mixing reagents in blisters in the test packs and for breaking the blisters to express reagents from the blisters to the reaction areas of the test packs; and sealer means operatively connected to the shoe means for sealing emptied reagent blisters, vacated reaction areas, and filled waste pouches in the test packs.

5. An automated diagnostics instrument in accordance with claim 1 wherein said processing station means includes:

clamp plate means for holding and supporting the test packs in an erect position; and pneumatically operated magnet means operatively associated with said clamp plate means for engaging said test packs and magnetically attracting metallic beads in said test packs carrying said optically detectable analytes.

6. An automated diagnostics instrument in accordance with claim 1 wherein said processing station means includes wastegate means for opening and closing the waste pouches in the test packs.

7. An automated diagnostics instrument for analyzing samples in test packs for analytes, said instrument comprising:

a loading station having a loading door for sequentially loading and unloading a series of test packs;

said test packs comprising closed disposable packs having burstable blisters containing reagents for selected tests, reaction areas and waste pouches, said closed disposable packs comprising flexible transparent plastic for viewing the reagents and samples contained in the packs, and said closed disposal packs having read cells for containing and displaying optically detectable analytes;

impact resistant trays comprising plastic back plates having closed disposable pack-receiving surfaces complementary in shape to portions of said disposable packs for matingly engaging and rigidly supporting said closed disposable packs, said trays defining window-receiving openings in alignment with said read cells and having horizontally slotted upper carrier portions and lower carrier portions, and said trays having posts secured to said closed disposable packs;

thermally conductive plates secured to said posts of said trays and engaging said closed disposable packs about said read cells for conducting heat to enhance amplification;

labels attached to said trays, said labels having bar codes corresponding to a desired test and identification of the samples and patient;

at least one bar code reader adjacent said loading station for scanning and reading the bar codes on said test packs to identify the samples and tests;

a carousel having slotted upper and lower platters comprising an eccentrically slotted upper disk and an eccentrically slotted spring-loaded lower disk, said upper and lower disk defining eccentric slots aligned in substantial vertical registration with each other for receiving and engaging said upper and lower carrier portions of said trays to hold said test packs in upright positions, a driven gear and a base positioned below and secured to said lower disk, a substantially vertical central shaft extending between and connecting said upper and lower disk and secured to said driven gear to rotate the carousel and platters holding said test packs;

an optical detector comprising a movable optical read head position in proximity to the base of said carousel for contacting said read windows to read and sense optically-detectable analytes in the read cells of the test packs;

a processing station for automatically expressing and mixing reagents with samples in said test packs, said processing station comprising pneumatically operated magnets for engaging said trays and magnetically attracting metallic beads in said test packs carrying said optically detectable analytes;

an upright wastegate assembly for opening and closing waste pouches in the disposable closed packs;

a substantially vertically moveable saddle assembly comprising a roller assembly having substantially horizontally reciprocating cam-driven rollers for mixing reagents and samples in reaction areas of the closed disposable packs and for moving background material comprising waste portions of the samples to waste pouches in the closed disposable packs;

a mixer assembly having substantially horizontally reciprocating cam-driven impact members comprising shoes for manipulating and mixing reagents in blisters in said closed disposable closed packs and for breaking the blisters to express reagents from the blisters to the reaction areas of said closed disposable packs;

a sealer assembly having substantially horizontally reciprocating cam-driven sealers including a side sealer for heat sealing substantially emptied reagent blisters and a reaction area sealer for heat sealing used substantially emptied vacated reaction areas and waste pouches containing the waste portions; and an upright belt conveyor assembly operatively connected to said saddle assembly for moving said saddle assembly substantially vertically so that said rollers shoes, and sealers can contact different areas of said closed disposable packs;

a load tram for transporting said test trays from said loading station to said carousel; and a processing tram for transporting said test trays from said carousel to said processing station; and each of said trams having a pair of conveyor belts moveable in substantially horizontal planes, said belts including an upper conveyor belt and a lower conveyor belt, said belts being aligned in substantial vertical registration with each other, a set of pulleys including substantially horizontally positioned pulleys for driving and rotating said conveyor belts in substantially horizontally directions, and a shuttle having an upper bracket attached to said upper conveyor belt with a guide rail for securely engaging said slotted upper carrier portions of said trays and a lower bracket attached to said lower conveyor belt with portions for securely engaging said lower carrier portions of said trays, and said shuttle and said conveyor belts cooperating with each other for conveying and carrying said test packs in a substantial vertical position.

8. An automated diagnostics instrument in accordance with claim 7 including a locking pin assembly for releasably securing said test packs on the carousel.

9. An automated diagnostics instrument in accordance with claim 7 wherein said read head comprises fluorescent detector for detecting fluorescent analytes 10. An automated diagnostics instrument in accordance with claim 7 wherein said read cells are keyhole shaped and said trays have inclined vanes about said read windows for providing part of docketing mechanisms to facilitate alignment and coupling of said optical detector and said windows.

* * * * *